US006258793B1

(12) United States Patent
Palle et al.

(10) Patent No.: US 6,258,793 B1
(45) Date of Patent: Jul. 10, 2001

(54) N6 HETEROCYCLIC 5' MODIFIED ADENOSINE DERIVATIVES

(75) Inventors: Venkata P. Palle; Jeff A. Zablocki; Prabha N. Ibrahim, all of Mountain View; Vaibhav Varkhedkar, Sunnyvale; Luiz Belardenelli, Menlo Park, all of CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 09/454,436

(22) Filed: Dec. 3, 1999

(51) Int. Cl.$^7$ .......................... A61K 31/70; C07H 19/167
(52) U.S. Cl. ..................... 514/46; 536/27.3; 536/27.63
(58) Field of Search ............................. 514/46; 536/27.3, 536/27.63

(56) References Cited

U.S. PATENT DOCUMENTS 5,789,416   8/1998   Lum et al. ............................. 514/46

OTHER PUBLICATIONS

B. Lerman et al, "Cardiac Electrophysiology of Adenosine", *Circulation*, vol. 83 (1991) p. 1499–1509 (May, 1991).
J.C. Shryock, "Adenosine and Adenosine Receptors in the Cardiovascular System: Biochemistry, Physiology, and Pharmacology", *The Am. Cardiology*, vol. 79 (1997) p. 2–10 (Jun. 19, 1997).
J.D. Thornton, "Intravenous Pretreatment with $A_1$–Selective Adenosine Analogues Protects the Heart Against Infarction". *Circulation*, vol. 85 (1992), p. 659–665 (2/92).
E. A. van Schaick et al., J., "Physiological Indirect Effect Modeling of the Antilipolytic Effects of Adenosine $A_1$–Receptor Agonists", *Pharmacokinetics and Biopharmaceutics*, vol. 25 (1997) p. 673–694.
P. Strong, "Suppression of non–esterified fatty acids and triacylglycerol in experimental animals by the adenosine analogue GR79236", *Clinical Science*, vol. 84 (1993), p. 663–669.
D. Thiebaud et al, "Effect of Long Chain Triglyceride Infusion on Glucose Metabolism in Man", *Metab. Clin. Exp.*, vol. 31 (1982), p. 1128–1136 (Nov., 1982).

G. Boden et al., "Mechanism of Fatty–Acid–Induced Inhibition of Glucose Uptake", *J. Clin. Invest.*, vol. 93, (1994) p. 2438–2446 (Jun., 1994).
P.J. Randle et al., "The Glucose Fatty–Acid Cycle Its Role in Insulin Sensitivity and the Metabolic Disturbances of Diabetes Mellitus", *Lancet* (1963) p. 785–789 (Apr. 13, 1963).
Klitgaard, et al., "Contrasting Effects of Adenosine $A_1$ and $A_2$ Receptor Ligands in Different Chemoconvulsive Rodent Models," *Eur. J. Pharmacol* (1993), vol. 224 pp. 221–228.
G. Zhang, "Activation of adenosine A1 receptors underlies anticonvulsant effect of CGS21680", *Eur. J. Pharmacol*, vol. 255 (1994), p. 239–243.
Knutsen, "N–Substituted Adenosines as Novel Neuroprotective A1 Agonists with Diminished Hypotensive Effects", *J. Med. Chem.*, vol. 42 (1999) p. 3463–3477.
Vergauwen, et al., "Adenosine Receptors Mediate Synergistic Stimulation of Glucose Uptake and Transport by Insulin and by Contractions in Rat Skeletal Muscle", *J. Clin. Invest*, (1994) 93, 974–81 (Mar. 1994).
Gellai, et al., "CVT–124, a Novel Adenosine A1 Receptor Antagonist with Unique Diuretic Activity", *JPET*, (1998) 286, p. 1191–1196.
Wilcox. et al., "Natriuretic and Diuretic Actions of a Highly Selective Adenosine $A_1$ Receptor Anagonist," *J. Am. Soc. Nephrol*, (1999) 10, p. 714–720.
R.B. Clark, et al., "Partial agonists and G protein–coupled receptor desensitization", *Tips*, vol. 20 (1999), p. 279–286 (Jul., 1999).
D. M. Dennis et al., "Homologous Desensitization of the A1–Adenosine Receptor System in the Guinea Pig Atrioventricular Node," *JPET*, vol. 272 (1995), p. 1024–1035.
Parsons, J., "Heterologus Desensitization of the Inhbitory A1 Adenosine Receptor–Adenylate Cyclase System in Rat Adipocytes", *Biol. Chem.* vol. 262 (1987) p. 841–847.

*Primary Examiner*—Gary Geist
*Assistant Examiner*—L. E. Crane
(74) *Attorney, Agent, or Firm*—McDonnell Boehnen Hulbert & Berghoff

(57) ABSTRACT

$N^6$ heterocyclic 5' modified adenosine derivatives that are adenosine $A_1$ receptor partial or full agonists, and as such, are useful for modifying cardiac activity, modifying adipocyte function, treating central nervous system disorders, and treating diabetic disorders and obesity in mammals, and especially in humans.

43 Claims, 2 Drawing Sheets

N6 HETEROCYCLIC 5' MODIFIED ADENOSINE DERIVATIVES

BACKGROUND OF THE INVENTION (1) Field of the Invention

There is provided useful drugs and pro-drugs that are $N^6$ heterocyclic 5' modified adenosine derivatives. The compositions of this invention are selective, partial or full adenosine $A_1$ receptor agonists, and as such, are useful for modifying cardiac activity, modifying adipocyte function, treating central nervous system disorders, and treating diabetic disorders and obesity in mammals, and especially in humans.

(2) Description of the Art

There are at least two subtypes of adenosine receptors in the heart: $A_1$ and $A_{2A}$. Each subtype affects different physiological functions. The $A_1$ adenosine receptor mediates two distinct physiological responses. Inhibition of the cardiostimulatory effects of catecholamine are mediated via the inhibition of adenylate cyclase, whereas the direct effects to slow the heart rate (HR) and to prolong impulse propagation through the AV node are due in great part to activation of $I_{KAdo}$. (B. Lerman and L. Belardinelli Circulation, Vol. 83 (1991), P 1499–1509 and J. C. Shryock and L. Belardinelli The Am. J. Cardiology, Vol. 79 (1997) P 2–10). Both, the anti-β-adrenergic action and direct depressant effects on SA and AV nodal function are mediated by the $A_1$ receptor; there is no role for the $A_{2A}$ receptor in this response to adenosine. $A_{2A}$ receptors mediate the coronary vasodilatation caused by adenosine. Stimulation of the $A_1$ adenosine receptor accordingly shortens the duration and decreases the amplitude of the action potential of AV nodal cells, and hence prolongs the refractory period of the AV nodal cell. The consequence of these effects is to limit the number of impulses conducted from the atria to the ventricles. This forms the basis of the clinical utility of $A_1$ receptor agonists for the treatment of supraventricular tachycardias, including termination of nodal re-entrant tachycardias, and control of ventricular rate during atrial fibrillation and flutter.

A clinical utility of $A_1$ agonists therefore is in the treatment of acute and chronic disorders of heart rhythm, especially those diseases characterized by rapid heart rate where the rate is driven by abnormalities in the sinoatrial, atria, and AV nodal tissues. Such disorders include but are not limited to atrial fibrillation, supraventricular tachycardia and atrial flutter. Exposure to $A_1$ agonists causes a reduction in the heart rate and a regularization of the abnormal rhythm thereby improving cardiovascular function.

$A_1$ agonists, through their ability to inhibit the effects of catecholamines, decrease cellular cAMP, and thus, should have beneficial effects in the failing heart where increased sympathetic tone increases cellular cAMP levels. The latter has been shown to be associated with increased likelihood of ventricular arrhythmias and sudden death. All of the above concepts are discussed in reviews regarding the effects of adenosine on cardiac electrophysiology (see B. Lerman and L. Belardinelli Circulation, Vol. 83 (1991), P 1499–1509 and J. C. Shryock and L. Belardinelli, Am. J. Cardiology, Vol. 79 (1997) P 2–10).

A controversial area in the field of $A_1$ adenosine agonism is that the benefit of preconditioning of the heart prior to ischemia may be due to binding of adenosine to the $A_1$ receptor. Evidence for this hypothesis comes from a rabbit ischemia model wherein 2-chloro-N6-cyclopentyladenosine (CCPA) and R-PIA were administered prior to ischemia providing protection with respect to infarct size (J. D. Thornton et al. Circulation Vol. 85 (1992) 659–665).

$A_1$ agonists, as a result of their inhibitory action on cyclic AMP generation, have antilipolytic effects in adipocytes that leads to a decreased release of nonesterified fatty acids (NEFA) (E. A. van Schaick et al J. Pharmacokinetics and Biopharmaceutics, Vol. 25 (1997) p 673–694 and P. Strong Clinical Science Vol. 84 (1993) p. 663–669). Non-insulin-dependent diabetes mellitus (NIDDM) is characterized by an insulin resistance that results in hyperglycemia. Factors contributing to the observed hyperglycemia are a lack of normal glucose uptake and activation of skeletal muscle glycogen synthase (GS). Elevated levels of NEFA have been shown to inhibit insulin-stimulated glucose uptake and glycogen synthesis (D. Thiebaud et al Metab. Clin. Exp. Vol. 31 (1982) p 1128–1136 and G. Boden et al J. Clin. Invest. Vol. 93 (1994) p 2438–2446). The hypothesis of a glucose fatty acid cycle was proposed by P. J. Randle as early as 1963 (P. J. Randle et al Lancet (1963) p. 785–789). A tenet of this hypothesis would be that limiting the supply of fatty acids to the peripheral tissues should promote carbohydrate utilization (P. Strong et al Clinical Science Vol. 84 (1993) p. 663–669).

The benefit of an $A_1$ agonist in central nervous disorders has been reviewed and the content are included herein by reference (L. J. S. Knutsen and T. F. Murray In Purinergic Approaches in Experimental Therapeutics, Eds. K. A. Jacobson and M. F. Jarvis (1997) Wiley-Liss, N. Y., P 423–470). Briefly, based on experimental models of epilepsy, a mixed $A_{2A}$: $A_1$ agonist, metrifudil, has been shown to be a potent anticonvulsant against seizures induced by the inverse benzodiazepine agonist methyl 6,7-dimethoxy-4-ethyl-beta-carboline-3-carboxylate (DMCM, H. Klitgaard Eur. J. Pharmacol. (1993) Vol. 224 p. 221–228). In other studies using CGS 21680, an $A_{2A}$ agonist, it was concluded that the anticonvulsant activity was attributed to activation of the $A_1$ receptor (G. Zhang et al. Eur. J. Pharmacol. Vol. 255 (1994) p. 239–243). Furthermore, $A_1$ adenosine selective agonists have been shown to have anticonvulsant activity in the DMCM model (L. J. S. Knutsen In Adenosine and Adenne Nucleotides: From Molecular Biology to Integrative Physiology; eds. L. Belardinelli and A. Pelleg, Kluwer: Boston, 1995, pp 479–487). A second area where an $A_1$ adenosine agonist has a benefit is in animal models of forebrain ischemia as demonstrated by Knutsen et al (J. Med. Chem. Vol. 42 (1999) p. 3463–3477). The benefit in neuroprotection is believed to be in part due to the inhibition of the release of excitatory amino acids (ibid).

There are a number of full $A_1$ agonists disclosed in the prior art. However, the agonists disclosed are generally in the forms that are not useful in the mammalian body. Because useful forms of $A_1$ agonists may not always be stable, soluble or they may have other properties that make their incorporation into therapeutic dosage forms difficult, it is often necessary to identify compositions that are more easily incorporated into therapeutic dosage forms in order to provide the desired therapeutic effect. Also, these agonists fail as useful therapeutics due to side effects caused by the non-selective stimulation of the $A_1$ adenosine receptor in all biologically available tissues and the desensitization of the desired response preempting their use as chronic agents. Therefore, there remains a need for specific and selective $A_1$ agonists, precursors and/or pro-drugs that are converted in the body into useful therapeutic compositions.

SUMMARY OF THE INVENTION

In one aspect, this invention includes heterocyclic 5' modified adenosine derivative compositions that are useful partial or full adenosine $A_1$ receptor agonists.

In another aspect, this invention includes pharmaceutical compositions including one or more heterocyclic 5' modified adenosine derivative compositions that are well tolerated with few side effects.

In still another embodiment, this invention includes heterocyclic 5' modified adenosine derivatives having the formula:

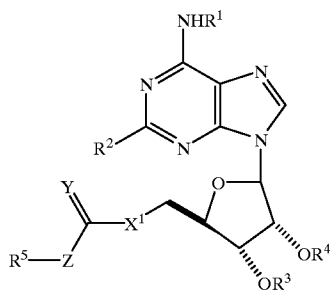

In yet another embodiment, this invention includes methods for administering compositions of this invention to mammals, and especially to humans, to modify cardiac activity, to modify adipocyte function, to treat central nervous system disorders, and to treat diabetic disorders.

In a further embodiment, this invention is pharmaceutical compositions of matter comprising at least one composition of this invention and one or more pharmaceutical excipients.

DESCRIPTION OF THE CURRENT EMBODIMENT

Figure 1A:
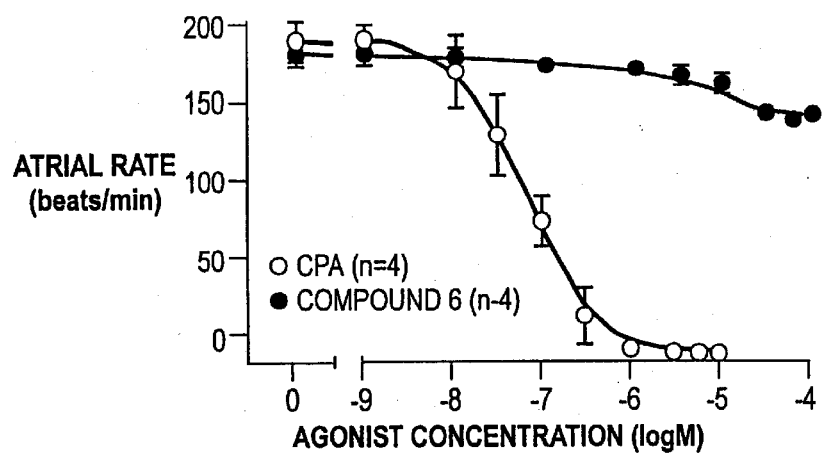
FIGS. 1A, 1B, and 1C are plots of the concentration-response relationships for the negative chronotropic (decrease of atrial rate, panel A), shortening of atrial monophasic action potential (MAP, panel B), and negative dromotropic (increase of stimulus to His-bundle conduction time, panel C) effects of Compound 6, CPA and CCPA. Each point represents the means±SEM of single determination in each of four hearts. Second degree AV block occurred in all hearts in the presence of 30 nM CPA.

This invention includes a class of heterocyclic 5' modified adenosine derivatives havinig the formula:

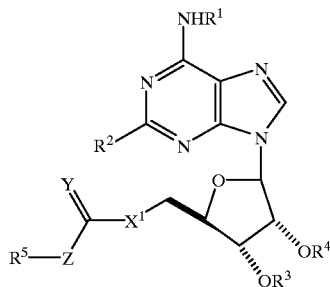

wherein $X^1$=O, S, $NR^6$; Y=O, S, N—CN, N—$OR^7$; Z=O, S, $NR^8$;

$R^1$ is a monocyclic or polycyclic heterocyclic group containing from 3 to 15 carbon atoms, wherein at least one carbon atom is substituted with an atom or molecule selected from the group consisting of N, O, P and S—$(O)_{0-2}$ and wherein $R^1$ does not contain an epoxide group;

$R^2$ is selected from the group consisting of hydrogen, halo, $CF_3$, and cyano;

$R^3$ and $R^4$ are each independently selected from the group consisting of hydrogen, and —(CO)—R' and —(CO)—R" wherein R', and R" are independently selected from the group consisting of $C_{1-15}$ alkyl, $C_{2-15}$ alkenyl, $C_{2-15}$ alkynyl, heterocyclyl, aryl, and heteroaryl, which alkyl, alkenyl, alkynyl, aryl, heterocyclyl, and heteroaryl are optionally substituted with 1 to 3 substituents independently selected from the group of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and each optional heteroaryl, aryl, and heterocyclyl substituent is further optionally substituted with halo, $NO_2$, alkyl, $CF_3$, amino, mono- or di-alkylamino, alkyl or aryl or heteroaryl amide, $NR^{20}COR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$;

$R^5$ is selected from the group consisting of $C_{1-15}$ alkyl, $C_{2-15}$ alkenyl, $C_{2-15}$ alkynyl, heterocyclyl, aryl, and heteroaryl, which alkyl, alkenyl, alkynyl, aryl, heterocyclyl and heteroaryl are optionally substituted with from 1 to 3 substituents independently selected from the group consisting of halo, alkyl, $NO_2$, heterocyclyl, aryl, heteroaryl, $CF_3$, CN, $OR^{20}$, $SR^{20}$, $N(R^{20})_2$, $S(O)R^{20}$, $SO_2R^{22}$, $SO_2N(R^{20})_2$, $S(O)_3R^{20}$, $P(O)(OR^{20})_2$, $SO_2NR^{20}COR^{22}$, $SO_2NR^{20}CO_2R^{22}$, $SO_2NR^{20}CON(R^{20})_2$, $NR^{20}COR^{22}$, $NR^{20}CO_2R^{22}$, $NR^{20}CON(R^{20})_2$, $NR^{20}C(N^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and each optional alkyl, heteroaryl, aryl, and heterocyclyl substituent is further optionally substituted with halo, $NO_2$, alkyl, $CF_3$, amino, mono- or di-alkylamino, alkyl or aryl or heteroaryl amide, $NR^{20}COR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $S(O)_3R^{20}$, $P(O)(OR^{20})_2$, $SR^{20}$, $S(O)R^{22}$, $SO_2R^{22}$, $SO_2N(R^{20})_2$, CN, or $OR^{20}$;

$R^6$ is selected from the group consisting of H, $C_{1-6}$ alkyl and aryl optionally substituted with halo, CN, $CF_3$, $OR^{20}$ and $N(R^{20})_2$, with the proviso that when $Z=NR^8$ then $R^6$ and $R^8$ may bond to form a 5 or 6 membered saturated or unsaturated ring;

$R^7$ and $R^8$ are independently selected from the group consisting of H, and $C_1$–$C_{15}$ alkyl optionally substituted with one aryl substituent that is optionally substituted with halo or $CF_3$;

$R^{20}$ is selected from the group consisting of H, $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl; and $R^{22}$ is selected from the group consisting of hydrogen, $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl, wherein when $Z=NR^8$ or when $X^1=NR^6$ then $R^6$ and $R^8$ may bond to form a 4 or 5 or 6 membered saturated or unsaturated ring and when $X^1=NR^6$ and $Y=O$, then $R^5$ and $R^6$ may bond to form a 5 membered ring wherein $R^5$ and $R^6$ together form C=C.

In one class of preferred compositions, $X^1=O$; $Y=O$ or S; $Z=NR^8$; $R^3$ and $R^4$ are each independently selected from the group consisting of hydrogen, —(CO)—R' and —(CO)—R" wherein R', and R" are each independently selected from the group consisting of hydrogen, and $C_{1-6}$ alkyl such as methyl, isopropyl, or cyclopentyl; $R^5$ is selected from the group consisting of $C_{1-8}$ alkyl, $C_{2-8}$ alkenyl, and aryl, which alkyl, alkenyl, and aryl, are each optionally substituted with from 1 to 2 substituents independently selected from the group of halo, alkyl, aryl, heteroaryl, $CF_3$, CN, $OR^{20}$, $S(O)R^{22}$, $SO_2R^{22}$, $SO_2N(R^{20})_2$, $S(O)_3R^{20}$, $NR^{20}COR^{22}$, $NR^{20}CON(R^{20})_2$, $CO_2R^{20}$, $CON(R^{20})_2$, and each optional alkyl, and aryl substituent is optionally substituted with halo, alkyl, $CF_3$, $CO_2R^{20}$, $S(O)_3R^{20}$, CN, or $OR^{20}$; $R^8$ is selected from the group consisting of H, and $C_1$–$C_3$ alkyl; and $R_{20}$ is a selected from the group consisting of H, $C_{1-6}$ alkyl such as methyl, which alkyl is optionally substituted with aryl wherein when $Z=NR^8$ then $R^5$ and $R^8$ may bond to form a 4 or 5 or 6 membered saturated ring. In the class of compounds above, $R^2$ is more preferably hydrogen, Y is more preferably O or S, $R^8$ is more preferably methyl or hydrogen, $R^5$ is more preferably selected from the group consisting of methyl, ethyl, n-propyl, n-butyl, cyclopentyl, benzyl, (4-fluorophenylmethyl), isopropyl, cyclopropyl, cyclohexyl, allyl, 2-carboethoxyethyl, carbomethoxymethyl, 2-phenylcyclopropyl, cyclobutyl, 2-benzyloxycyclopentyl, 2-hydroxycyclopentyl, 2-carbomethoxycyclopentyl, 2-(3-carboethoxy-norborn-5-enyl), 2-(3-carboxy-norborn-5-enyl), 2-(3-carboethoxy-norbornyl), and 2-carboxycyclopentyl and $R^8$ is more preferably methyl or, when $Z=NR^8$, then $R^5$ and $R^8$ may bond to form a 5 or 6 membered saturated ring.

In another class of preferred compositions, $X^1$ is $NR^6$; $Y=O$ or S; $Z=O$; $R^2$ is H; $R^3$ and $R^4$ are independently selected from the group consisting of hydrogen, —(CO)—R', and —(CO)—R" wherein R', and R" are each methyl; $R^5$ is selected from the group consisting of $C_{1-8}$ alkyl, $C_{2-8}$ alkenyl, and aryl, which alkyl, alkenyl, and aryl, are optionally substituted with from 1 to 2 substituents independently selected from the group of halo, alkyl, aryl, heteroaryl, $CF_3$, CN, $OR^{20}$, $S(O)R^{22}$, $SO_2R^{22}$, $SO_2N(RO^{20})_2$, $S(O)_3R^{20}$, $NR^{20}COR^{22}$, $NR^{20}CON(R^{20})_2$, $CO_2R^{20}$, $CON(R^{20})_2$, and wherein each optional alkyl, and aryl substituent is optionally substituted with halo, alkyl, $CF_3$, $CO_2R^{20}$, $S(O)_3R^{20}$, CN, or $OR^{20}$; $R^6$ is selected from the group consisting of H, and $C_{1-3}$ alkyl wherein when $X=NR^6$ then $R^5$ and $R^6$ may bond to form a 4 or 5 or 6 membered saturated or unsaturated ring. In the preferred class of compounds above, $R^3$ and $R^4$ are more preferably each hydrogen, $R^5$ is a $C_{1-8}$ alkyl such as methyl or cyclopentyl, $R^6$ is hydrogen, or when $X^1=NR^6$, and $Y=O$, then and $R^5$ and $R^6$ may bond to form a 5 membered unsaturated ring wherein $R^5$ and $R^6$ together form CH=CH.

In still another class of preferred compositions, $X^1=S$; $Y=O$ or S; $Z=NR^8$; $R^2$ is H; $R^3$ and $R^4$ are each independently selected from the group consisting of hydrogen, —(CO)—R'and —(CO)—R", wherein R' and R" are each methyl; $R^5$ is selected from the group consisting of $C_{1-8}$ alkyl, $C_{2-8}$ alkenyl, and aryl, which alkyl, alkenyl and aryl, are optionally substituted with from 1 to 2 substituents independently selected from the group consisting of halo, alkyl, aryl, heteroaryl, $CF_3$, CN, $OR^{20}$, $S(O)R^{22}$, $SO_2R^{22}$, $SO_2N(R^{20})_2$, $S(O)_3R^{20}$, $NR^{20}COR^{22}$, $NR^{20}CON(R^{20})_2$, $CO_2R^{20}$, $CON(R^{20})_2$, and wherein each optional alkyl and aryl substituen further optionally substituted with halo, alkyl, $CF_3$, $CO_2R^{20}$, $S(O)_3R^{20}$, CN, or $OR^{20}$; and $R^8$ is selected from the group consisting of H, and $C_1$–$C_3$ alkyl. In the class of compounds above, $R^3$ and $R^4$ are more preferably each hydrogen, $R^5$ is preferably a $C_{1-8}$ alkyl such as methyl or cyclopentyl that is optionally substituted with 1 substituent selected from the group consisting of aryl, $OR^{20}$, $CO_2R^{20}$, $CON(R^{20})_2$, and wherein each optional aryl substituent is optionally substituted with halo, alkyl, $CF_3$, $CO_2R^{20}$, and $R^8$ is preferably hydrogen.

In yet another class of preferred compositions, $X^1=NR^6$; $Y=O$ or S; $Z=NR'$; $R^2$ is H; $R^3$ and $R^4$ are each independently selected from the group consisting of hydrogen, —(CO)—R' and —(CO)—R" wherein R', and R" are each methyl; $R^5$ is selected from the group consisting of $C_{1-8}$ alkyl, $C_{2-8}$ alkenyl, and aryl, which alkyl, alkenyl, and aryl, are optionally substituted with from 1 to 2 substituents independently selected from the group consisting of halo, alkyl, aryl, heteroaryl, $CF_3$, CN, $OR^{20}$, $S(O)R^{22}$, $SO_2R^{22}$, $SO_2N(R^{20})_2$, $S(O)_3R^{20}$, $NR^{20}COR^{22}$, $NR^{20}CON(R^{20})_2$, $CO_2R^{20}$, $CON(R^{20})_2$, and wherein each optional alkyl, and aryl substitue optionally substituted with halo, alkyl, $CF_3$, $CO_2R^{20}$, $S(O)_3R^{20}$, CN, or $OR^{20}$; $R^6$ is selected from the group consisting of H, and $C_1$–$C_3$ alkyl; and $R^8$ is selected from the group consisting of H, and $C_1$–$C_3$ alkyl, wherein $R^6$ and $R^8$ may bond to form a 4 or 5 or 6 membered saturated or unsaturated ring. In the compositions above, $R^3$ and $R^4$ are each more preferably hydrogen, $R^5$ is more preferably $C_{1-8}$ alkyl such and methyl or cyclopentyl, and $R^8$ is more preferably hydrogen.

In the compositions of this invention, $R^1$ is preferably mono or polysubstituted with one or more compounds selected from the group consisting of halogen, oxo, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl, nitro, cyano and mixtures thereof. More preferably, $R^1$ is a monocyclic, bicyclic, or tricyclic cycloalkyl group containing from 3 to 15 carbon atoms wherein at least one carbon atom is substituted with an atom or molecule selected from the group consisting of O or S—(O)$_{0-2}$. Some examples of preferred R$^1$ moieties include

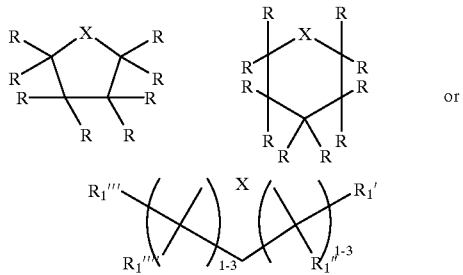

wherein R$_1'$, R$_1''$, R$_1'''$, and R$_1''''$ may each individually be selected from the group halogen, hydroxyl, lower alkyl, substituted lower alkyl, alkoxy, aryl, acyl, aryloxy, carboxyl, substituted aryl, heterocycle, heteroaryl, substituted heteroaryl, cycloalkyl, substituted cycloalkyl, nitro, and cyano, and X is O, or S (—O)$_{0-2}$, alternately, R$_1'''$ and R$_1''''$ may be a single oxygen atom. More preferably, R$_1'$, R$_1''$, R$_1'''$, and R$_1''''$ are each individually selected from the group hydrogen, lower alkyl, and substituted lower alkyl. In the compositions above, each R is individually selected from the group consisting of H, lower alkyl, and substituted lower alkyl and wherein X is O, or S (—O)$_{0-2}$. R$_1$ is more preferably selected from the group consisting of 3-tetrahydrofuranyl, 3-tetrahydrothiofuranyl, 4-pyranyl, and 4 thiopyranyl. R$_1$ is most preferably 3-tetrahydrofuranyl.

Most preferred compounds of this invention include, (5-{6-[((3R)oxolan-3-yl)amino]purin-9-yl}(3S,2R,4R,5R)-3,4-dihydroxyoxolan-2-yl)methoxy]-N-methylcarboxamide; [(5-{6-[((3R)oxolan-3-yl)amino]purin-9-yl}(3S,2R,4R,5R)-3,4-dihydroxyoxolan-2-yl)methoxy]-N-ethylcarboxamide; [(5-{6-[((3R)oxolan-3-yl)amino]purin-9-yl}(3S,2R,4R,5R)-3,4-dihydroxyoxolan-2-yl)methoxy]-N-propylcarboxamide; [(5-{6-[((3R)oxolan-3-yl)amino]purin-9-yl}(3S,2R,4R,5R)-3,4-dihydroxyoxolan-2-yl)methoxy]-N-butylcarboxamide; [(5-{6-[((3R)oxolan-3-yl)amino]purin-9-yl}(3S,2R,4R,5R)-3,4-dihydroxyoxolan-2-yl)methoxy]-N-cyclopentylcarboxamide; [(5-{6-[((3R)oxolan-3-yl)amino]purin-9-yl}(3S,2R,4R,5R)-3,4-dihydroxyoxolan-2-yl)methoxy]-N-benzylcarboxamide; [(5-{6-[((3R)oxolan-3-yl)amino]purin-9-yl}(3S,2R,4R,5R)-3,4-dihydroxyoxolan-2-yl)methoxy]-N-[(4-fluorophenyl)methyl]carboxamide; {(5-{6-[((3R)oxolan-3-yl)amino]purin-9-yl}(3S,2R,4R,5R)-3,4-dihydroxyoxolan-2-yl)methoxy]-N-cyclohexylcarboxamide; {(5-{6-[((3R)oxolan-3-yl)amino]purin-9-yl}(3S,2R,4R,5R)-3,4-dihydroxyoxolan-2-yl)methoxy]-N-(methylethyl)carboxamide; {(5-{6-[((3R)oxolan-3-yl)amino]purin-9-yl}(3S,2R,4R,5R)-3,4-dihydroxyoxolan-2-yl)methoxy]-N-cyclopropylcarboxamide; Methyl 2-{[5-{6-[(3R)oxolan-3-yl)amino]purin-9-yl}(3S,2R,4R,5R)-3,4-dihydroxyoxolan-2-yl)methoxy]carbonylamino}cyclopentanecarboxylate; Ethyl 3-{[5-{6-[(3R)oxolan-3-yl)amino]purin-9-yl}(3S,2R,4R,5R)-3,4-dihydroxyoxolan-2-yl)methoxy]carbonylamino}(2S,3R)bicylo[2.2.1]hept-5-ene-2-carboxylate; Ethyl 3-{[5-{6-[(3R)oxolan-3-yl)amino]purin-9-yl}(3S,2R,4R,5R)-3,4-dihydroxyoxolan-2-yl)methoxy]carbonylamino}(2S,3R)bicylo[2.2.1]heptane-2-carboxylate; {(5-{6[((3R)oxolan-3-yl)amino]purin-9-yl}(3S,2R,4R,5R)-3,4-dihydroxyoxolan-2-yl)methoxy]-N-[(1R,2R)-2-(phenylmethoxy)cyclopentyl]carboxamide; {(5-{6-[((3R)oxolan-3-yl)amino]purin-9-yl}(3S,2R,4R,5R)-3,4-dihydroxyoxolan-2-yl)methoxy]-N-[(1S,2S)-2-(phenylmethoxy)cyclopentyl]carboxatnide; (5-{6-[((3R)oxolan-3-yl)amino}purin-9-yl}(3S,2R,4R,5R)-3,4-dihydroxyoxolan-2-yl)methoxy]-N-cyclobutylcarboxamide; [(5-{6-[((3R)oxolan-3-yl)amino}purin-9-yl}(3S,2R,4R,5R)-3,4-dihydroxyoxolan-2-yl)methoxy]-N-(2-phenylcyclopropyl)carboxamide; [(5-{6-[((3R)oxolan-3-yl)amino]purin-9-yl}(3S,2R,4R, 5R)-3,4-dihydroxyoxolan-2-yl)methoxy]-N-prop-2-enylcarboxamide; Ethyl 3-{[(5-{6-[((3R)oxolan-3-yl)amino]purin-9-yl}(3S,2R,4R,5R)-3,4-dihydroxyoxolane-2-yl)methoxy}carbonylamino}propanoate; Methyl 2-{[(5-{6-[((3R)oxolan-3-yl)amino]purin-9-yl}(3S,2R,4R,5R)-3,4-dihydroxyoxolane-2-yl)methoxy}carbonylamino}acetate; {(5-{6-[((3R)oxolan-3-yl)amino]purin-9-yl}(3S,2R,4R,5R)-3,4-dihydroxyoxolan-2-yl)methoxy]-N,N-dimethylcarboxamide; 2-{6-[((3R)oxolan-3-yl)amino]purin-9-yl}(4S,2R,3R,5R)- 5-{[(methylamino)thioxomethoxy]methyl}oxolane-3,4-diol; 2-{6-[((3R)oxolan-3-yl)amino]purin-9-yl}(4S,2R,3R,5R)-5-{[(ethylamino)thioxomethoxy]methyl}oxolane-3,4-diol; 2-{6-[((3R)oxolan-3-yl)amino]purin-9-yl}(4S,2R,3R,5R)-5-({[(methylethyl)amino]thioxomethoxy}methyl)oxolane-3,4-diol; 2-{6-[((3R)oxolan-3-yl)amino]purin-9-yl}(4S,2R,3R,5R)-5-{[(butylamino)thioxomethoxy]methyl}oxolane-3,4-diol; 2-{6-[((3R)oxolan-3-yl)amino]purin-9-yl}(4S,2R,3R,5R)-5-{[(propylamino)thioxomethoxy]methyl}oxolane-3,4-diol; 2-{6-[((3R)oxolan-3-yl)amino]purin-9-yl}(4S,2R,3R,5R)-5-[(piperidylthioxomethoxy)methyl]oxolane-3,4-diol; 2-{6-[((3R)oxolan-3-yl)amino]purin-9-yl}(4S,2R,3R,5R)-5-{[(cyclopentylamino)thioxomethoxy]methyl}oxolane-3,4-diol; 2-{6-[((3R)oxolan-3-yl)amino]purin-9-yl}(4S,2R,3R,5R)-5-[(pyrrolidinylthioxomethoxy)methyl]oxolane-3,4-diol; 2-{6-[((3R)oxolan-3-yl)amino]purin-9-yl}(4S,2R,3R,5R)-5-{[(dimethylamino)thioxomethoxy]methyl}oxolane-3,4-diol; 2-{6-[((3R)oxolan-3-yl)amino]purin-9-yl}(4S,2R,3R,5R)-5-({[benzylamino]thioxomethoxy}methyl)oxolan-3-diol; 2-{6-[((3R)oxolan-3-yl)amino]purin-9-yl}(4S,2R,3R,5R)-5-({[cyclohexylamino]thioxomethoxy}methyl)oxolane-3,4-diol; 2-{6-[((3R)oxolan-3-yl)amino]purin-9-yl}(4S,2R,3R,5R)-5-[({[(1S,2S)-2-(phenylmethoxy)cyclopentyl]amino}thioxomethoxy)methyl]oxolane-3,4-diol; 2-{6-[((3R)oxolan-3-yl)amino]purin-9-yl}(4S,2R,3R,5R)-5-[({[(1R,2R)-2-(phenylmethoxy)cyclopentyl]amino}thioxomethoxy)methyl]oxolane-3,4-diol; 2-{6-[((3)oxolan-3-yl)amino]purin-9-yl}(4S,2R,3R,5R)-5-{[(cyclobutylamino)thioxomethoxy]methyl}oxolane-3,4-diol; 2-{6-[((3R)oxolan-3-yl)amino]purin-9-yl}(4S,2R,3R,5R)-5-{[(cyclopropylamino)thioxomethoxy]methyl}oxolane-3,4-diol; 2-{6-[((3R)oxolan-3-yl)amino]purin-9-yl}(4S,2R,3R,5R)-5-}[(prop-2-enylamino)thioxomethoxy]methyl}oxolane-3,4-diol; {(5-{6[((3R)oxolan-3-yl)amino]purin-9-yl}(3S,2R,4R,5R)-3,4-dihydroxyoxolan-2-yl)methoxy]-N-((1S,2S)-2-hydroxycyclopentyl)carboxamide; {(5-{6[((3R)oxolan-3-yl)amino]purin-9-yl}(3S,2R,4R,5R)-3,4-dihydroxyoxolan-2-yl)methoxy]-N-((1R,2R)-2-hydroxycyclopentyl)carboxamide; 2-{6-[((3R)oxolan-3-yl)amino]purin-9-yl}(4S,2R,3R,5R)-5-({[((1R,2R)-2-hydroxycyclopentyl)amino]thioxomethoxy}methyl)oxolane- 3,4-diol; 2-{6-[((3R)oxolan-3-yl)amino]purin-9-yl}(4S,2R,3R,5R)-5-({[((1S,2S)-2-hydroxycyclopentyl)amino]thioxomethoxy}methyl)oxolane-3,4-diol; 2-{[5-{6-[(3R)

oxolan-3-yl)amino]purin-9-yl}(3S,2R,4R,5R)-3,4-dihydroyoxolan-2-yl)methoxy]carbonylamino}cyclopentanecarboxylic acid; 3-{[(5-{6-[((3R)oxolan-3-yl)amino]purin-9-yl}(3S,2R,4R,5R)-3,4-dihydroxyoxolan-2-yl)methoxy]carbonylamino}(2S,3R) bicyclo[2.2.1]hept-5-ene-2-carboxylic acid; 3-{[(5-{6-[((3R)oxolan-3-yl)amino]purin-9-yl}(3S,2R,4R,5R)-3,4-dihydroxyoxolan-2-yl)methoxy]carbonylamino}propanoic acid; 2-{[(5-{6-[((3R)oxolan-3-yl)amino]purin-9-yl}(3S,2R,4R,5R)-3,4-dihydroxyoxolan-2-yl)methoxy]carbonylamino}acetic acid, 5-{6-[((3R)oxolan-3-yl)amino]purin-9-yl}(2R,3R,4R,5R)-4-acetyloxy-2-[(N-methylcarbamoyloxy)methyl]oxolan-3-yl acetate; [(5-(6-[((3R)oxolan-3-yl)amino]-2-chloropurin-9-yl}(3S,2R,4R,5R)-3,4-dihydroxyoxolan-2-yl)methoxy]-N-methylcarboxamide, [(5-{6-[((3R)oxolan-3-yl)amino]-2-chloropurin-9-yl}(3S,2R,4R,5R)-3,4-dihydroxyoxolan-2-yl)methoxy]-N-cyclopentylcarboxamide; N-[(5-{6-[((3R)oxolan-3-yl)amino]purin-9-yl}(3S,2R,4R,5R)-3,4-dihydroxyoxolan-2-yl)methyl]methoxycarboxamide; N-[(5-{6-[((3R)oxolan-3-yl)amino]purin-9-yl}(3S,2R,4R,5R)-3,4-dihydroxyoxolan-2-yl)methy] cyclopentyloxycarboxamide; 2-{6-[((3R)oxolan-3-yl)amino]purin-9-yl}(4S,2R,3R,5R)-5-{[methoxythioxomethyl)amino]methyl}oxolane-3,4-diol; 2-{6-[((3R)oxolan-3-yl)amino]purin-9-yl}(4S,2R,3R,5R)-5-{[cyclopentyloxythioxomethyl)amino]methyl}oxolane-3,4-diol; [(5-{6-[((3R)oxolan-3-yl)amino]purin-9-yl}(2S,3S,4R,5R)-3,4-dihydroxyoxolan-2-yl)methythio]-N-methylcarboxamide; [(5-{6-[((3R)oxolan-3-yl)amino]purin-9-yl}(2S,3S,4R,5R)-3,4-dihydroxyoxolan-2-yl)methythio]-N-cyclopentylcarboxamide; 2-{6-[((3R)oxolan-3-yl)amino]purin-9-yl}(4S,5S,2R,3R)-5-{[(methylamino)thioxomethylthio]methyl}oxolane-3,4-diol; 2-{6l-[((3R)oxolan-3-yl)amino]purin-9-yl}(4S,5S,2R,3R)-5-{[(cyclopentylamino)thioxomethylthio]methyl}oxolane-3,4-diol; N-[(5-{6-[((3R)oxolan-3-yl)amino]purin-9-yl}(3S,2R,4R,5R)-3,4-dihydroxyoxolan-2-yl)methyl](methylamino)carboxamide; N-[(5-{6-[((3R)oxolan-3-yl)amino]purin-9-yl}(3S,2R,4R,5R)-3,4-dihydroxyoxolan-2-yl)methyl](cyclopentylamino)carboxamide; 2-{6-[((3R)oxolan-3-yl)amino]purin-9-yl}(4S,2R,3R,5R)-5-({[(methylamino)thioxomethyl]amino}methyl)oxolane-3,4-diol; 2-{6-[((3R)oxolan- 3-yl)amino]purin-9-yl}(4S ,2R,3R,5R)-5-({[(cyclopentylamino)thioxomethyl]aminol methyl)oxolane-3,4-diol; N-[(5-{6-[((3R)oxolan-3-yl)amino]purin-9-yl}(3S,2R,4R,5R)-3,4-dihydroxyoxolan-2-yl)methyl](ethylamino)carboxamide; and 3-[(5-{6-[((3R)oxolan-3-yl)amino]purin-9-yl}(3S,2R,4R)-3,4-dihydroxyoxolan-2-yl)methyl]-1,3-oxazolin-2-one.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15 carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 2–4, carbon atoms and at least one, preferably 1–3, more preferably 1–2, most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR''' R'''', where R is lower alkyl, or substituted lower alkyl, R', R''', R'''' may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1–4, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R—Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R—HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

"Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, hetaryl, substituted hetaryl, nitro, cyano, thiol, sulfamido and the like.

The compounds of this invention can be prepared as outlined in the schemes 1–10, below. The primary amino compound, $R_1NH_2$, is either commercially available or can be prepared as previously described (U.S. Pat. No. 5,789, 416). Compound I can be prepared, following the procedures reported earlier (U.S. Pat. No. 5,789,416, the specification of which is incorporated herein by reference), by reacting 6-chloropurine riboside 1 with a primary amine $R^1NH_2$. To facilitate carbamate formation at the 5' position, 2', 3' hydroxy groups can be protected as acetonide by reating I with 2,2'-dimethoxypropane in the presence of catalytic amount of TsOH [Evans, Parrish and Long Carbohydrat. Res., 3, 453 (1967)] to give II. Reaction of II with CDI or thio-CDI followed by treatment with an amine with the general formula $R^5R^8NH$ can give carbamates with general formula III. Treatment of III with an acid can free the 2', 3' positions to give carbamates with general formula IV. Esterification at the 2', 3' positions can afford 2', 3' diesters with the general formula V.

Scheme 1

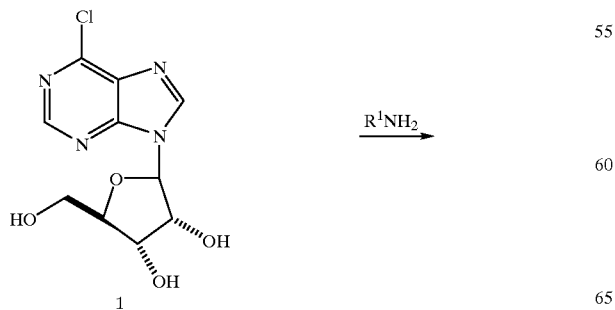

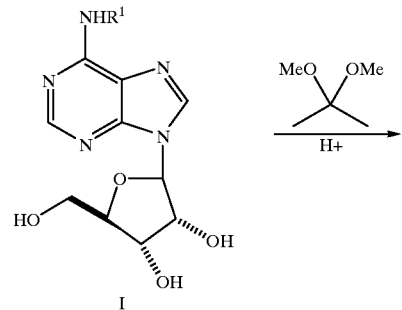

I

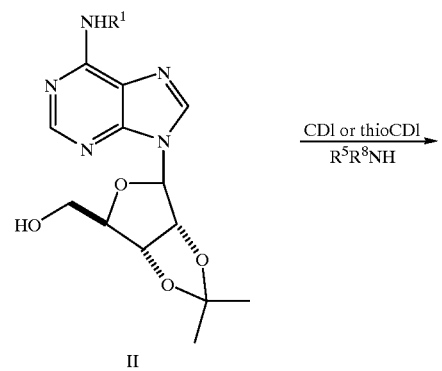

II

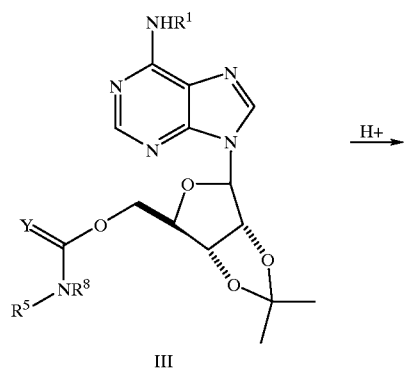

III

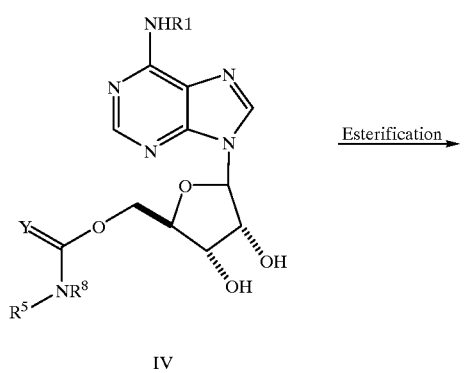

IV

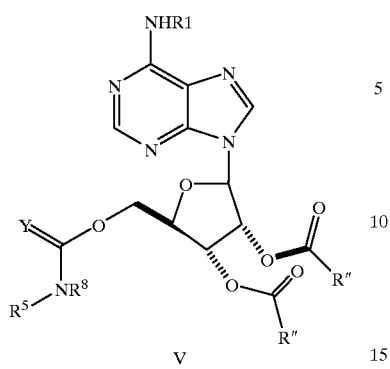

V

The 2-substituted derivatives with the general formula XIII can be prepared as shown in scheme 2. Condensation of 1,2,3,5-tetraacetylribofuranoside 2 with 2-substituted 6-chloropurine VI can give 2-substituted-6-chloropurineriboside triacetate VII which on reaction with a primary amine $R^1NH_2$ can give 2-substituted-6-alkylamino derivatives VIII. Hydrolysis of the acetates followed by protection of the 2', 3' hydroxy groups as an acetonide can give X. Reaction of X with either CDI or thio CDI followed by reaction with an amine $R^5R^8NH_2$ can give carbamate or thionocarbamate with the general Scheme 2

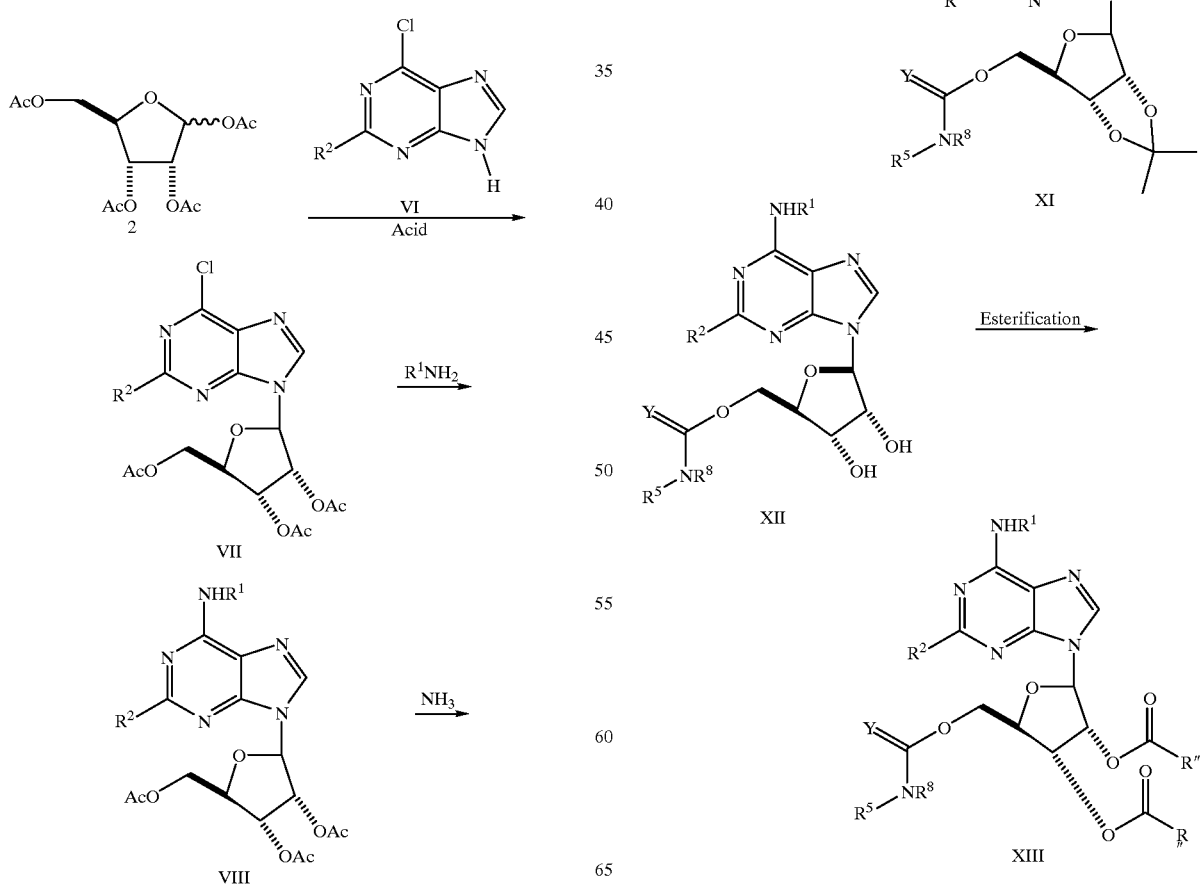

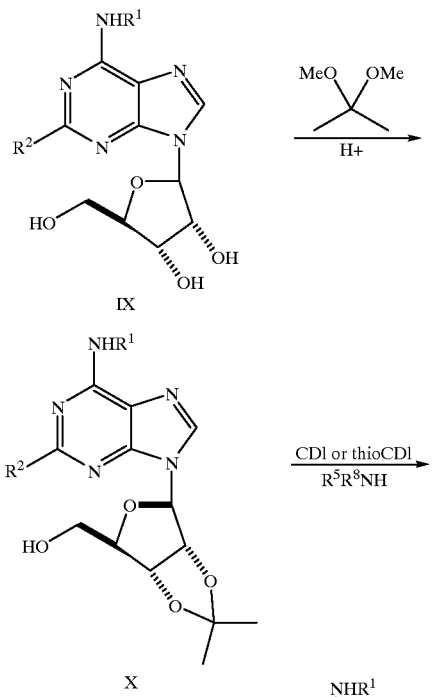

formula XI. Deprotection of the 2', 3'-positions can give carbamates with the general formula XII. Esterification of the 2', 3' hydroxyls can give diesters with the general formula XIII.

Preparation of compounds 6 and 7 starting from compound 3 is shown in Scheme 3. Compound 3 was prepared from 6-chloropurineriboside 1 and 3 (R)-aminotetrahydrofuran following the procedure reported earlier (U.S. Pat. No. 5,789,416). Protection of the 2' and 3' hydroxy groups as an acetonide with 2,2-dimethoxypropane in the presence of TsOH(cat.) gave 4. Reaction of 4 with CDI in THF followed by treatment with 40% aq.methylamine gave carbamate 5. Deprotection of the 2',3' acetonide with 80% AcOH/water at 80–90 C gave carbamate 6. Esterification of 6 with acetic anhydride in pyridine gave diester 7.

Preparation of compound 13 starting from compound 2 is shown in scheme 4. Compound 8 was prepared following the previously described procedure (John A. Montgomery et.al. J. Heterocycl. Chem. 1964, 213.). Selective displacement of the 6-chloro with 3 (R)-aminotetrahydrofuran following the procedure reported earlier (U.S. Pat. No. 5,789, 416, the specification of which is incorporated herein by reference) gave 9. Hydrolysis of the acetates at the 2',3', 5' positions with aq. ammonia gave trihydroxy compound 10. Protection of the 2' and 3' hydroxy groups as an acetonide with 2,2-dimethoxypropane in the presence of TsOH(cat.) gave 11. Reaction of 11

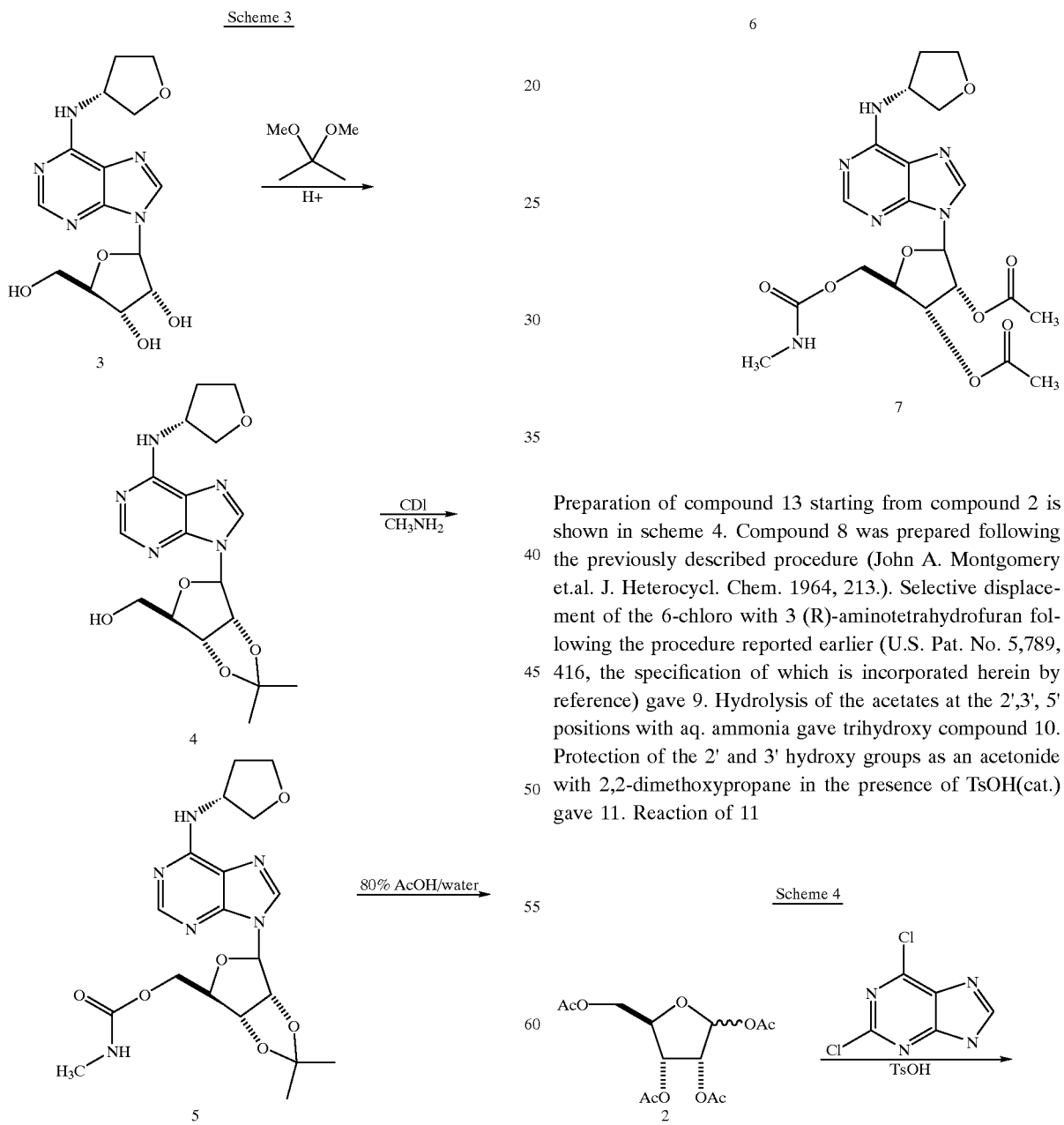

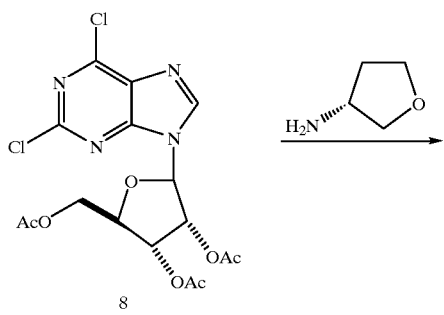

8

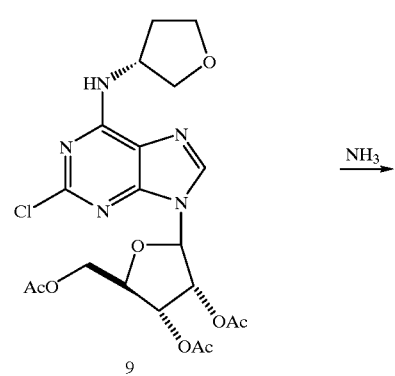

9

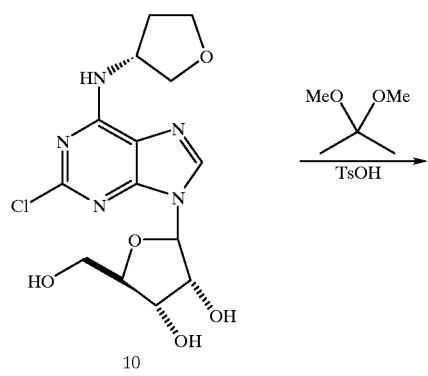

10

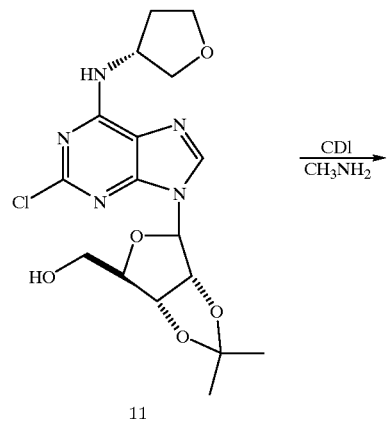

11

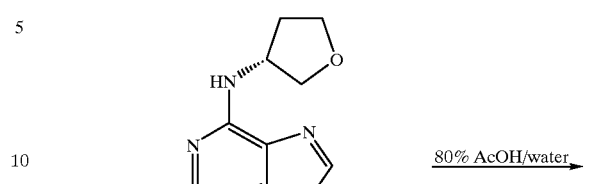

12

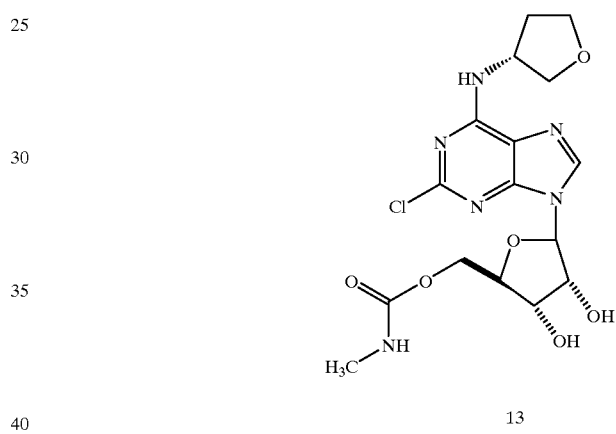

13 with CDI in THF followed by treatment with 40% aq.m-ethylamine gave carbamate 12. Deprotection of 12 with 80% AcOH/water at 80–90° C. gave carbamate 13.

Carbamates with general structure XVIII can be prepared from the key intermediate compound XVI as shown in Scheme 5.

Compound XVI can be prepared by the reduction of compound XV using 10% Pd-C and hydrogen (J. March, Advanced Organic Chemistry, $4^{th}$ edition, p 1220). Compound XV can be prepared by the nucleophilic displacement of the corresponding mesylate (XIV) with sodium azide (J. March, Advanced Organic Chemistry, $4^{th}$ edition, p 428) which can be prepared from the alcohol by treating compound II with methanesulfonyl chloride in pyridine.

Scheme 5

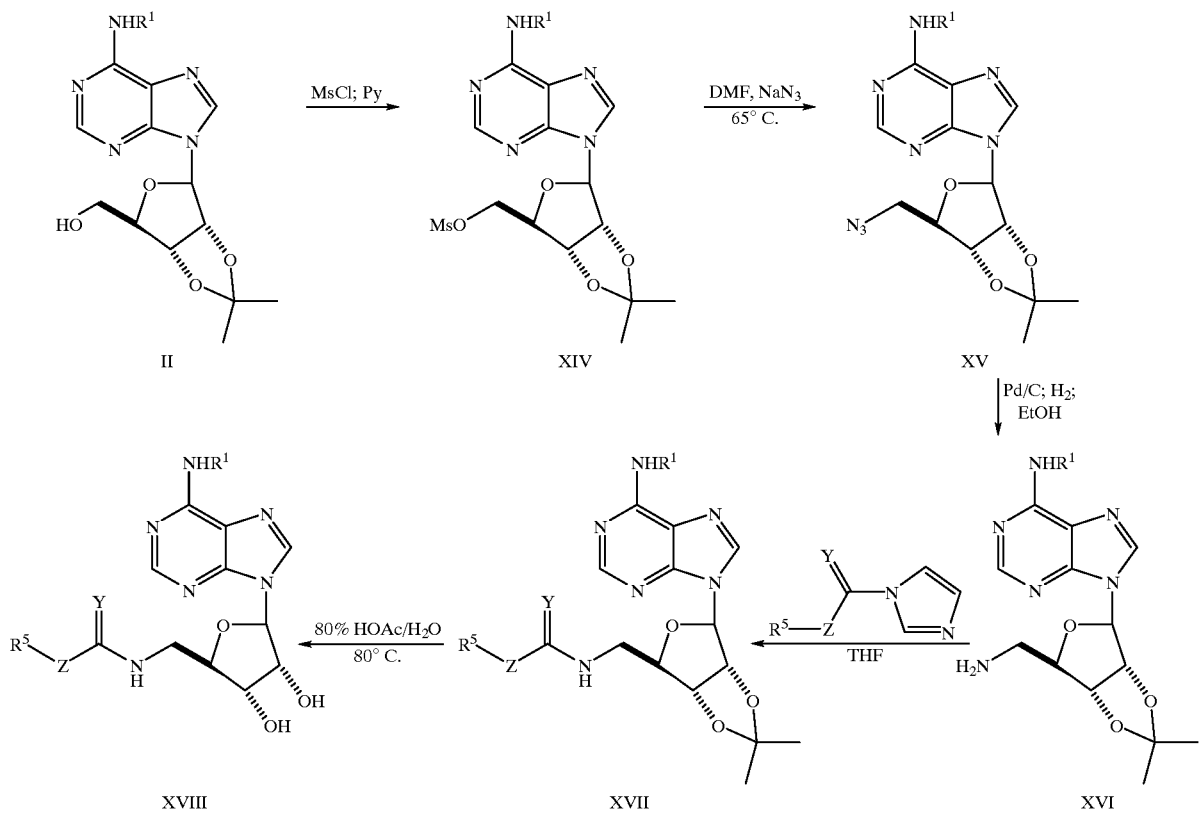

5'-Thiocarbamates represented by the general structure XXII can be prepared as shown in Scheme 6.

The key intermediate XX can be prepared by the deacylation of compound XIX that can be prepared by the nucleophilic displacement of the mesylate (XIV) by potassium thioacetate. Compound XXII can be obtained by the reaction of XX with isocyanates or isothiocyanates in acetonitrile, DMAP, followed by deprotection of the acetonide using aqueous acetic acid.

Scheme 6

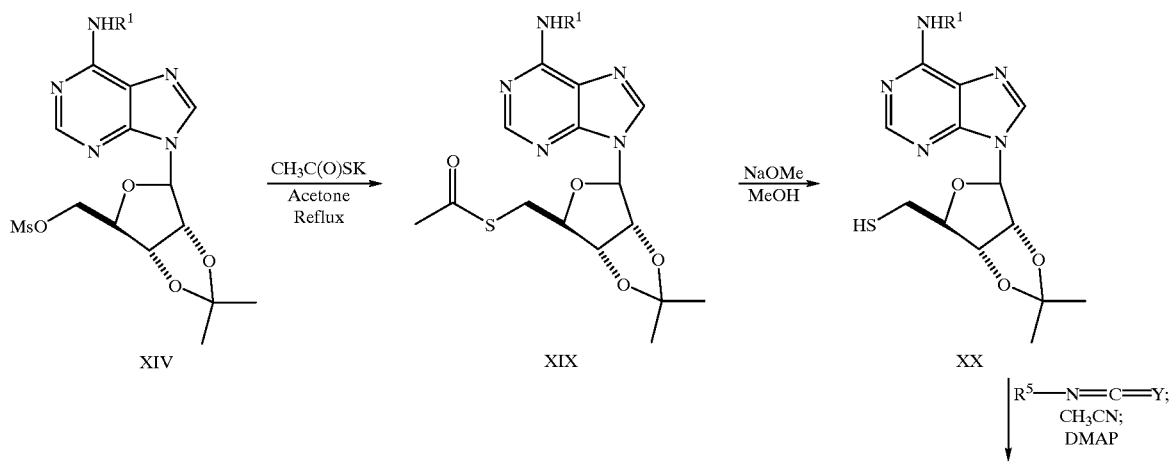

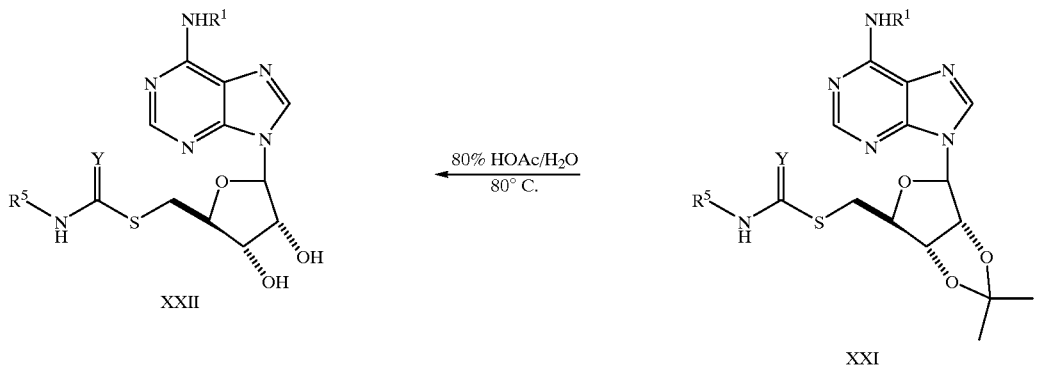

The ureas and thioureas represented by the general formula XXIV can be prepared from compound XVI, as shown in Scheme 7, by reacting with an isocyanate or isothiocyanate in acetonitrile, DMAP, followed by deprotection using aqueous acetic acid. Compound XVI can be prepared as described before (Scheme 5).

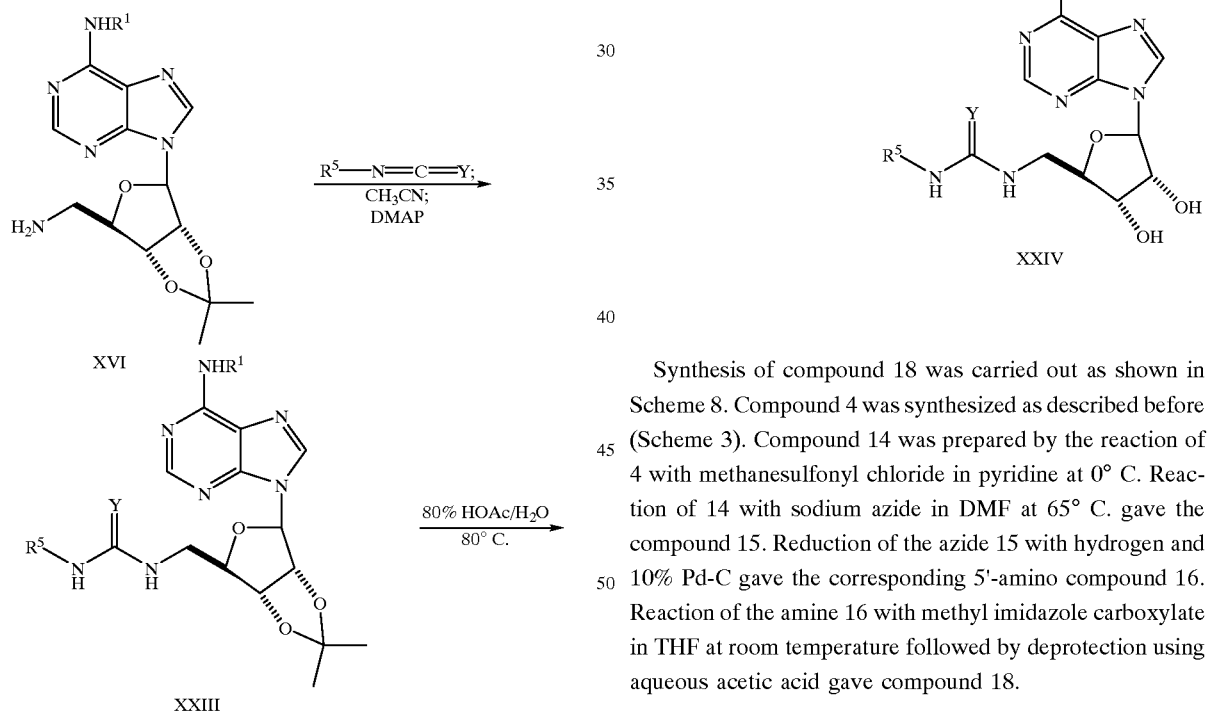

Synthesis of compound 18 was carried out as shown in Scheme 8. Compound 4 was synthesized as described before (Scheme 3). Compound 14 was prepared by the reaction of 4 with methanesulfonyl chloride in pyridine at 0° C. Reaction of 14 with sodium azide in DMF at 65° C. gave the compound 15. Reduction of the azide 15 with hydrogen and 10% Pd-C gave the corresponding 5'-amino compound 16. Reaction of the amine 16 with methyl imidazole carboxylate in THF at room temperature followed by deprotection using aqueous acetic acid gave compound 18.

Scheme 8

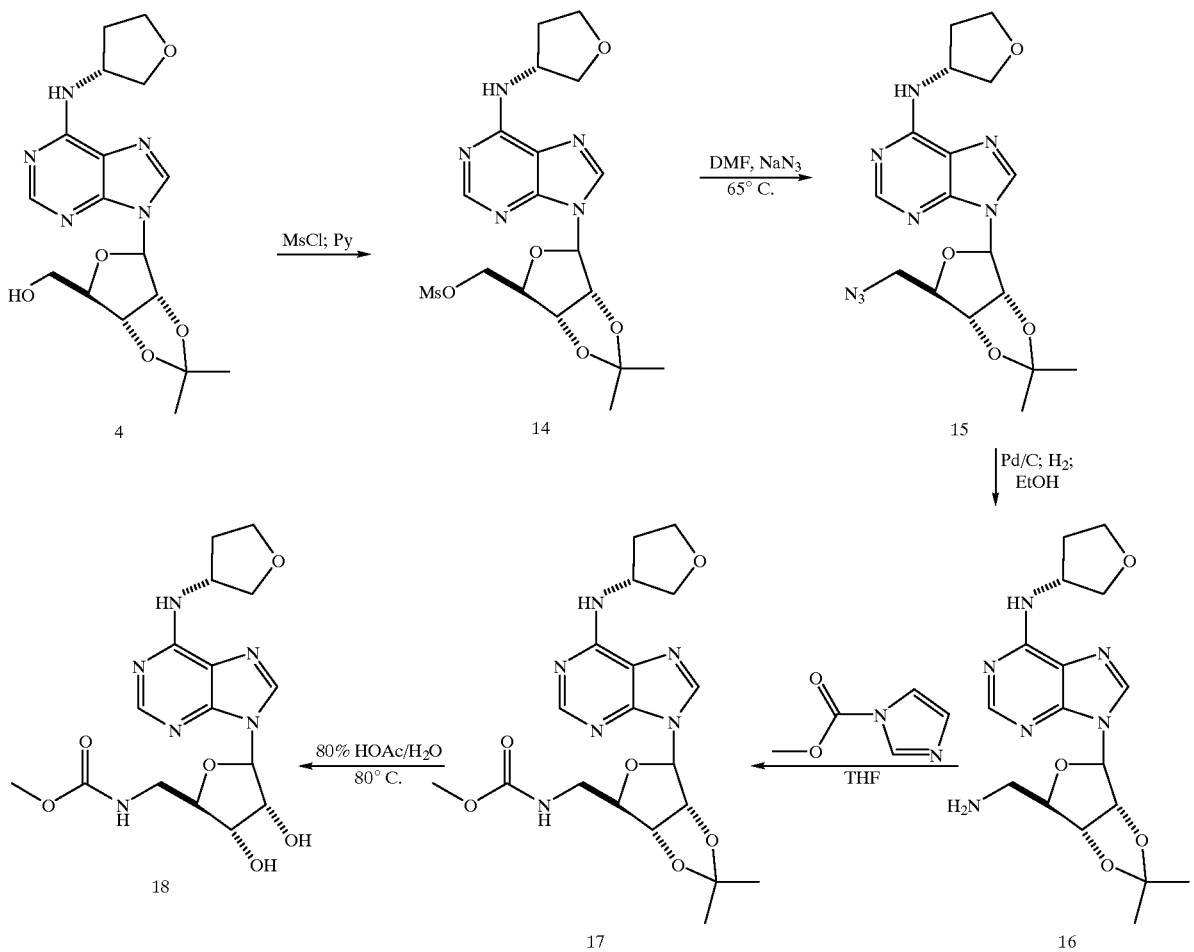

Compound 22 was synthesized as shown in Scheme 9. The mesylate 15 was prepared as described before (Scheme 8). Reaction of 15 with potassium thioacetate in THF at room temperature gave compound 19. Hydrolysis of compound 19 with sodium methoxide in methanol gave the thiol 20. Reaction of 20 with methyl isocyanate in acetonitrile and DMAP followed by deprotection gave compound 22.

Scheme 9

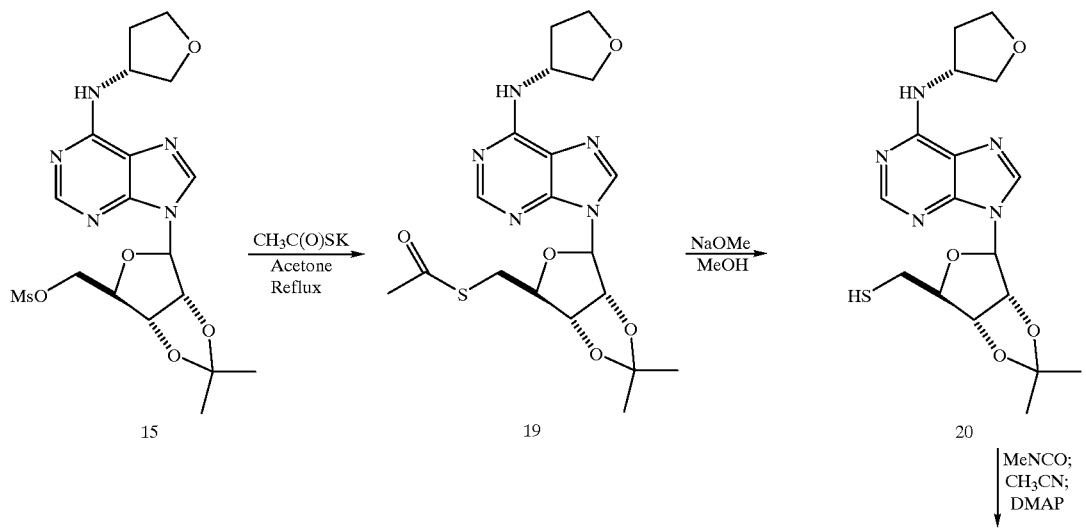

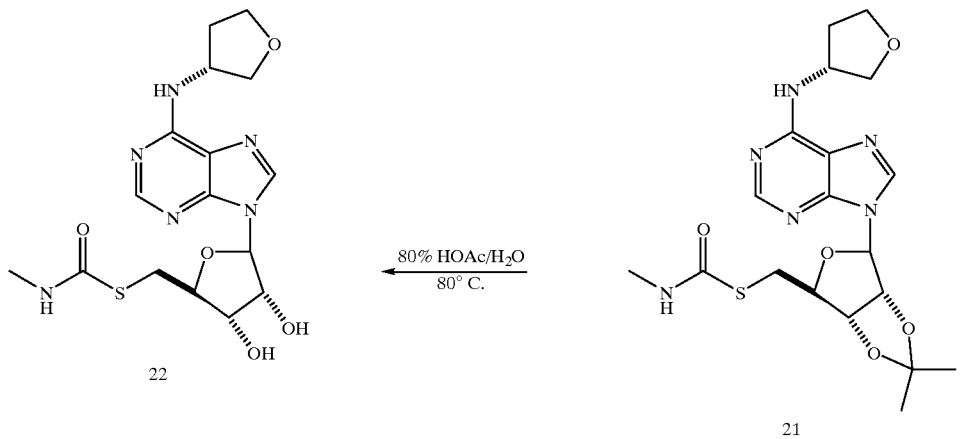

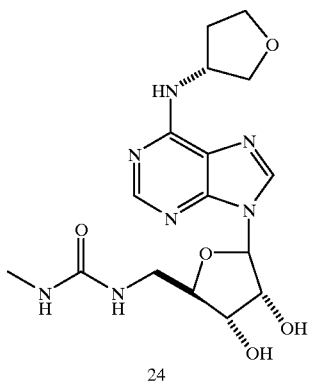

Compound 24 was prepared (Scheme 10) by the reaction of compound 16 with methyl isocyanate in acetonitrile, DMAP at room temperature followed by deprotection with aqueous acetic acid. Compound 16 was synthesized as described before (Scheme 8).

Scheme 10

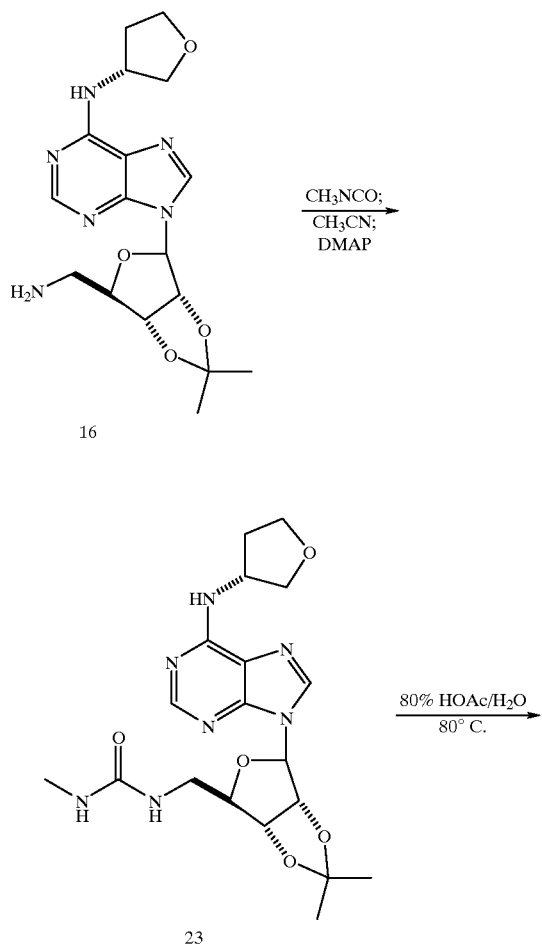

This invention also includes pro-drugs of the $A_1$ agonist compositions of this invention. A pro-drug is a drug which has been chemically modified and may be biologically inactive at its site of action, but which will be degraded or modified by one or more enzymatic or in vivo processes to the bioactive form. The pro-drugs of this invention should have a different pharmacokinetic profile to the parent enabling improved absorption across the mucosal epithelium, better salt formulation and/or solubility and improved systemic stability. The compounds of this invention may be preferably modified at one or more of the hydroxyl groups to form pro-drugs. The modifications may be (1) ester derivatives which may be cleaved by esterases or lipases, for example. The pro-drug esters of this invention can be prepared using all of the known methods for ester formation which are included by reference (see Jerry March Organic synthesis and Richard Larock—Methods of Organic Synthesis), and more preferably by those outlined in this application; (2) peptides which may be recognized by specific or non specific proteinase; or (3) derivatives that accumulate at a site of action through membrane selection or a pro-drug form or modified pro-drug form, or any combination of (1) to (3) above.

If a compound of this invention contains a basic group, then corresponding acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methanesulfonic. The hydrochloric salt form is especially useful. If a compound of this invention contains an acidic group, then corresponding cationic salts may be prepared. Typically the parent compound is treated with an excess of an alkaline reagent, such as hydroxide, carbonate or alkoxide, containing the appropriate cation. Cations such as $Na^+$, $K^+$, $Ca^{+2}$ and $NH_4^+$ are examples of cations present in pharmaceutically acceptable salts. Certain of the compounds form inner salts or zwitterions which may also be acceptable.

The compositions of this invention are useful for treating a variety of mammalian disorders and preferably human disorders that are mediated by an $A_1$ adenosine receptor. For example, the compositions of this invention are useful for modifying cardiac activity in mammals experiencing a coronary electrical disorder that can be treated by stimulating an $A_1$ adenosine receptor. Examples of coronary electrical disorders that can be treated by the compositions of this invention include supraventricular tachycardias, atrial fibrillation, atrial flutter, and AV nodal re-entrant tachycardia. Furthermore, orally active $A_1$ agonists of this invention that demonstrate an excellent safety profile in treating supraventricular arrhythmias may also be used as a prophylactic for those at high risk of a myocardial ischemia.

The compositions of this invention are also useful for modifying adipocyte function by stimulating an $A_1$ adenosine receptor that leads to diminished release of NEFA and increased release of leptin. Disease states related to adipocyte function that can be modified using compositions of this invention include diabetes, and obesity.

In skeletal muscle cells, $A_1$ AdoR agonists mediate a synergistic stimulation of glucose uptake and transport by insulin (Vergauwen, L. et al, *J. Clin. Invest.* 1994, 93, 974–81; Challiss, R. A. et al, *EurJ.Pharacol.*, 1992, 226, 121–8). Another therapeutic utility of compositions of this invention is more efficient regulation of glucose decrease in insulin in patients afflicted with diabetes.

The $A_1$ receptor agonist, R-PIA, has been shown to increase the leptin released from white adipocytes and augment insulin-stimulated leptin production (M. Ozeck Master's Thesis Univ. of Florida 1999 with L. Belardinelli). Evidence suggests that catecholamines inhibit the production of leptin from adipocytes through activation of β-adrenergic receptors. The anti-β-adrenergic effects of $A_1$ agonists on the adipocytes are believed to play a role in the increased release of leptin. The functional role of leptin is multifaceted including decreased appetite, stimulated energy utilization, and increased fertility.

The compositions of this invention may also be used to provide central nervous system neuroprotection by stimulating an $A_1$ adenosine receptor. Central nervous system disorders that may be treated using the compositions of this invention include epilepsy, and stroke.

In the kidney, there is evidence that stimulation of the $A_1$ AdoR promotes sodium retention, promotes exchange of sodium in urine for potassium, and reduces glomerular filtration rate as sodium excretion increases (Gellai, M. et al, *JPET*, 1998, 286, 1191–6; Wilcox, C. S. et al, *J.Am.Soc.Nephrol.*, 1999, 10, 714–720). It is believed that these responses are elicited by chronic local production of adenosine. That is, in the kidney there is a tonic effect of adenosine to stimulate the $A_1$ AdoR. Another clinical utility of compositions of this invention, therefore, is the selective antagonism of the $A_1$ AdoR in the kidney to inhibit sodium retention, inhibit the exchange of sodium for potassium, and preserve kidney glomerular filtration rate when sodium excretion rises to yield a potassium sparring diuretic that preserves renal function.

The compositions of this invention are further useful for providing cardiomyocyte protection from ischemic events by stimulating an $A_1$ adenosine receptor. Ischemic events treatable using the compositions of this invention include stable angina, unstable angina, cardiac transplant, and myocardial infarction.

An important aspect of compounds of this invention is that each compound has an intrinsic efficacy associated with it (for a discussion see T. P. Kenakin Stimulus Response Mechanisms. In Pharmacological Analysis of Drug-Receptor Interaction, Ed. Kenakin, T. P. New York: Raven Press, p 39–68). This intrinsic efficacy is not defined by it's affinity for the receptor, but it is defined as the quantitative effect of the compound to activate a given effector system (eg. cAMP production) in a given cell type. The intrinsic efficacy of a given compound may vary from cell type to cell type and/or from effector system to effector system. When a compound has an intrinsic efficacy lower than a full agonist (i.e. submaximal) than the agonist is called a partial agonist. Thus, a partial agonist is a molecule that binds to a receptor and elicits a response that is smaller than that of a full agonist (submaximal), but also competitively antagonizes the response(s) elicited by a full agonist (e.g., adenosine). The tonic action of adenosine with respect to kidney function is a prime example wherein a partial $A_1$ agonist could be expected to act as an antagonist. The compounds of this invention are believed to have therapeutically useful affinities for the adenosine A1 receptor, and they will have a range of intrinsic efficacies from full agonist to partial agonist. That is, some compounds may have no effect with respect to a given effector system in a given cell type, but be a full agonist in another cell type and/or effector system. The reason for such variable pharmacological behavior relates to the magnitude of the receptor reserve for the $A_1$ adenosine receptor in any given cell type (eg. AV nodal cells vs. adipocytes) and for a given response. The receptor reserve (spare receptor capacity) is the total number of receptors minus the fraction of receptors that is required to induce the maximal response using a full agonist (L. E. Limbird, Cell Surface Receptors: A Short Course on Theory and Methods, Kluwer Acad. Pub. 1996, Boston, Mass.). Therefore, the agonist could be a full agonist at eliciting a response, and a partial agonist for eliciting another response in other tissue or cells and still be an antagonist or lack activity for a third response in another tissue or cell. Consequently, a partial agonist targeted to a selected target is likely to cause fewer side effects than a full agonist. As a corollary, a full agonist elicits all the effects mediated by the respective receptor, whereas this is not necessarily the case of a partial agonist. The compounds of this invention based on their affinity for the $A_1$ receptor and their potency and selectivity to elicit $A_1$ receptor mediated responses have the potential for therapeutic intervention in the multiple disease states described above.

Partial $A_1$ agonists may have an added benefit for chronic therapy because they will be less likely to induce desensitization of the $A_1$ receptor (R. B. Clark, B. J. Knoll, R. Barber TiPS, Vol. 20 (1999) p. 279–286) and to cause side effects. Chronic administration of a full agonist (R-N6-phenylisopropyladenosine, R-PIA) for 7 days led to a desensitization of the $A_1$ receptor in terms of the dromotropic response in guinea pigs (note: a decrease in receptor number was observed—D. M. Dennis, J. C. Shryock, L. Belardinelli JPET, Vol. 272 (1995) p. 1024–1035). The $A_1$ agonist induced inhibitory effect on the production of cAMP by adenylate cyclase in adipocytes has been shown to desensitize upon chronic treatment with an $A_1$ agonist as well (W. J. Parsons and G. L. Stiles J. Biol. Chem. Vol. 262 (1987) p. 841–847).

The compositions of this invention may be administered orally, intravenously, through the epidermis, bolus, nasally, by inhalation or by any other means known in the art for administering a therapeutic agents. The method of treatment comprises the administration of an effective quantity of the chosen compound, preferably dispersed in a pharmaceutical carrier. Dosage units of the active ingredient are generally selected from the range of 0.01 to 100 mg/kg, but will be readily determined by one skilled in the art depending upon the route of administration, age and condition of the patient.

Pharmaceutical compositions including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxycellulose, acacia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glycerol monostearate or glycerol distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

The Examples which follow serve to illustrate this invention. The Examples are intended to in no way limit the scope of this invention, but are provided to show how to make and use the compounds of this invention.

EXAMPLE 1

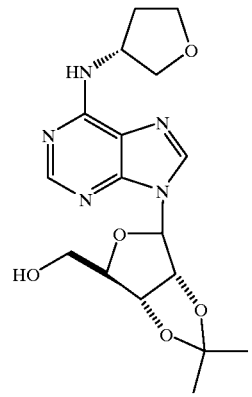

4

Intermediate—(4-{6-[((3R)oxolan-3-yl)amino]purin-9-yl}(1R,2R,5R)-7,7-dimethyl-3,6,8-trioxabicyclo[3.3.0]oct-2-yl)methan-1-ol(15A)

To a solution of compound 1 (2.0 g, 6.0 mmol) and 2,2-dimethoxypropane (1.2 g, 11.8 mmol) in dimethylformamide (20 mL) was added p-toluenesulfonic acid (50 mg, 0.26 mmol) at 70° C. After 48 h at 70° C., the reaction was concentrated in vacuo to afford a solid. The solid was dissolved in methanol (3 mL), then triturated with ethyl ether (50 mL). The resultant crystals were collected by vacuum filtration to afford the intermediate 4.

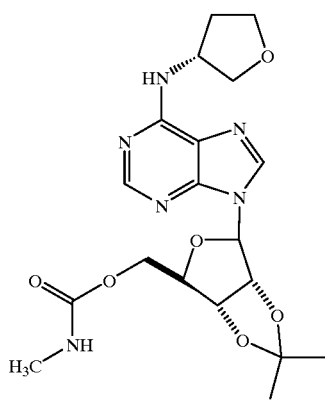

5

Intermediate-[(4-{6-[((3R)oxolan-3-yl)amino]purin-9-yl}(1R,2R,4R,5R)-7,7-dimethyl-3,6,8-trioxabicyclo[3.3.0]oct-2-yl)methoxy]-N-methylcarboxamide(5)

To a solution of compound 4 (190 mg, 0.5 mmol) in THF (1 mL) was added carbonyldiimidazole (324 mg, 2 mmol) at rt. After stirring for 2 h , excess reagent was quenched by adding a drop of water. Methylamine (40% aq. Solution, 1 mL) was added and stirring was continued for another 16 h. The reaction mixture was concentrated in vacuo to afford a gum. It was purified by prep.TLC [(silica gel, 10% MeOH-dichloromethane)] to afford compound 5 (100 mg).

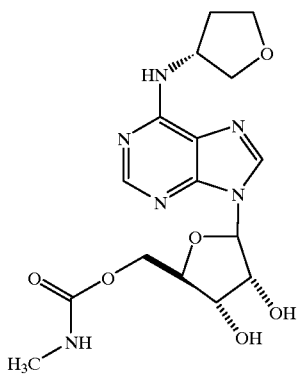

6

(5-{6-[((3R)oxolan-3-yl)amino]purin-9-yl}(3S,2R,4R,5R)-3,4-dihydroxyoxolan-2-yl)methoxy]-N-methylcarboxamide.(6) or (5'-O-(N-methylcarbamoyl)-6-((3R)-tetrahydrofuranyl)adenosine)

Compound 5 (100 mg) was taken in a mixture of acetic acid (16 mL) and water (4 mL) and heated at 90 C for 16 h. Solvents were removed under reduced pressure and the residue was purified by preparative TLC [methanol-dichloromethane (1:9)] to afford compound 6. $^1$H NMR (CD$_3$OD) 1.95–2.05 (m, 1H), 2.30–2.40 (m, 1H), 2.70 (s, 3H), 3.75–3.80 (m, 1H), 3.82–3.90 (m, 1H), 3.95–4.10 (m, 2H), 4.20–4.45 (m, 4H), 4.65 (t, 1H), 4.70–4.90 (m, 1H), 6.00 (d, 1H), 8.20 (s, 1H), 8.25 (s, 1H).

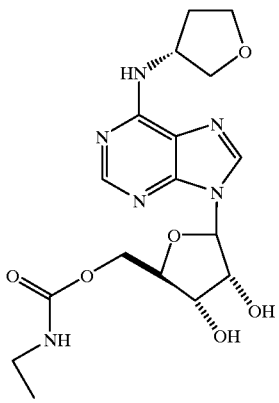

25

[(5-{6-[((3R)oxolan-3-yl)amino]purin-9-yl}(3S,2R,4R,5R)-3,4-dihydroxyoxolan-2-yl)methoxy]-N-ethylcarboxamide(25) or (5'-O-(N-ethylcarbamoyl) 6-((3R)-tetrahydrofuranyl)

This compound was prepared in a manner similar to that of 6, substituting ethyl amine for methyl amine: (M+1)= 409.35

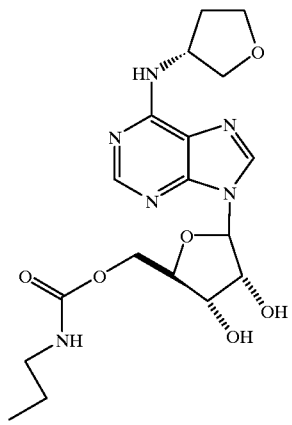

26

[(5-{6-[((3R)oxolan-3-yl)amino]purin-9-yl}(3S,2R,4R,5R)-3,4-dihydroxyoxolan-2-yl)methoxy]-N-propylcarboxamide(26) or (5'-O-(N-propylcarbamoyl)-6-((3R)-tetrahydrofuranyl)adenosine)

This compound was prepared in a manner similar to that of 6, substituting propyl amine for methyl amine: (M+1)= 423.35

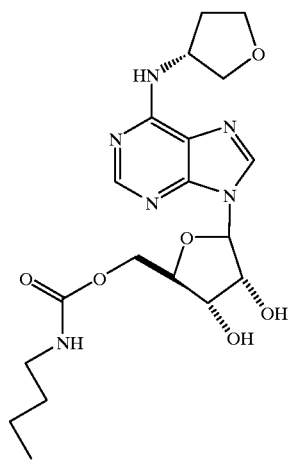

27

[(5-{6-[((3R)oxolan-3-yl)amino]purin-9-yl}(3S,2R,4R,5R)-3,4-dihydroxyoxolan-2-yl)methoxy]-N-butylcarboxamide(27) or (5'-O-(N-butylcarbamoyl)-6-((3R)-tetrahydrofuranyl)adenosine)

This compound was prepared in a manner similar to that of 6, substituting n-butyl amine for methyl amine: (M+1)= 437.39

28

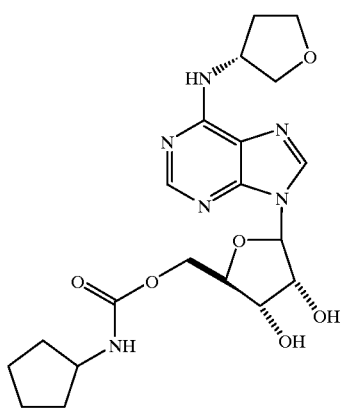

[(5-{6-[((3R)oxolan-3-yl)amino]purin-9-yl}(3S,2R, 4R,5R)-3,4-dihaydroxyoxolan-2-yl)methoxy]-N-cyclopentylcarboxamide(28) or (5'-O-(N-cyclopentylcarbamoyl)-6-((3R)-tetrahydrofuranyl) adenosine)

This compound was prepared in a manner similar to that of 6, substituting cyclopentyl amine for methyl amine: (M+1)=449.38

29

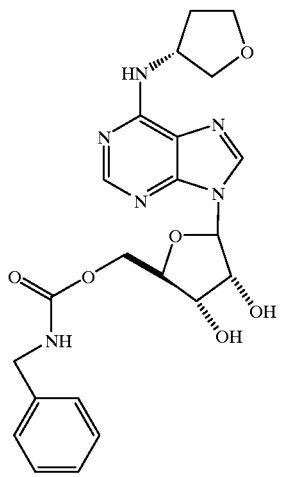

[(5-{6-[((3R)oxolan-3-yl)amino]purin-9-yl}(3S,2R, 4R,5R)-3,4-dihydroxyoxolan-2-yl)methoxy]-N-benzylcarboxamide(29) or (5'—O-(N-benzylcarbamoyl)-6-((3R)-tetrahydrofuranyl) adenosine)

This compound was prepared in a manner similar to that of 6, substituting benzyl amine for methyl amine: (M+1)= 471.37

30

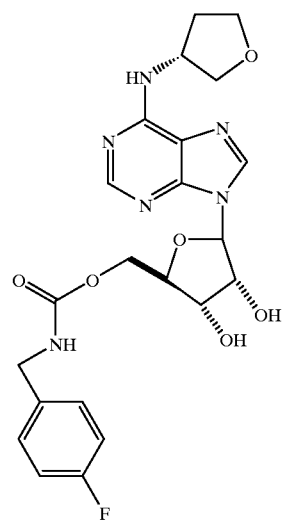

[(5-{6-[((3R)oxolan-3-yl)amino]purin-9-yl}(3S,2R, 4R,5R)-3,4-dihydroxyoxolan-2-yl)methoxy]-N-[(4-fluorophenyl)methyl]carboxamide(30) or (5'-O-(N-(4-fluorophenylmethylcarbamoyl)-6-((3R)-tetrahydrofuranyl)adenosine)

This compound was prepared in a manner similar to that of 6, substituting 4-fluorobenzyl amine for methyl amine: (M+1)=489.3

31

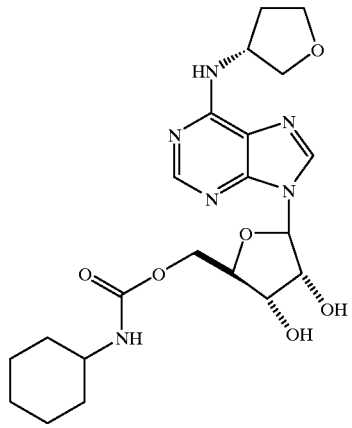

{(5-{6-[((3R)oxolan-3-yl)amino purin-9-yl}(3S,2R, 4R,5R)-3,4-dihydroxyoxolan-2-yl)methoxy]-N-cyclohexylcarboxamide(31) or (5'-O-[N-cyclohexylcarbamoyl]-6-((3R)-tetrahydrofuranyl) adenosine)

This compound was prepared in a manner similar to that of 6, substituting cyclohexyl amine for methyl amine: $^1$H NMR (CD$_3$OD) 1.1–1.95 (m, 11H), 2.35 (m, 1H), 3.75–4.55 (m, 11H), 5.98 (d, 1H), 8.12 (s, 1H), 8.25 (s, 1H).

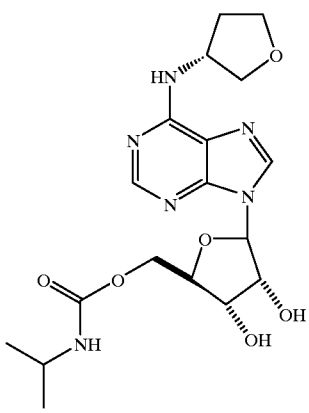

32

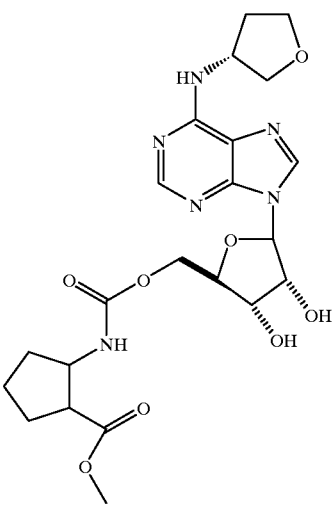

34

{(5-{6-[((3R)oxolan-3-yl)amino]purin-9-yl}(3S,2R,4R,5R)-3,4-dihydroxyoxolan-2-yl)methoxy]-N-(methylethyl)carboxamide(32) or (5'-O-[N-isopropylcarbamoyl]-6-[((3R)-tetrahydrofuranyl)] adenosine)

Methyl 2-{[5-{6-[(3R)oxolan-3-yl)amino]purin-9-yl}(3S,2R,4R,5R)-3,4-dihydroxyoxolan-2-yl) methoxy]carbonylamino}cyclopentanecarboxylate (34) or (5'-O-[N-2-(methoxycarbonyl) cyclopenthylcarbamoyl]-6-[((3R)-tetrahydrofuranyl)]adenosine)

This compound was prepared in a manner similar to that of 6, substituting i-propyl amine for methyl amine: (M+1)= 423.3

This compound was prepared in a manner similar to that of 6, substituting 2-carbomethoxy cyclopentyl amine for methyl amine: (m+1)=507.31

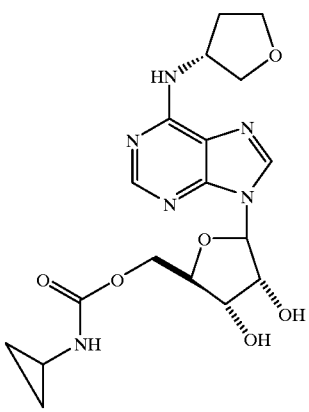

33

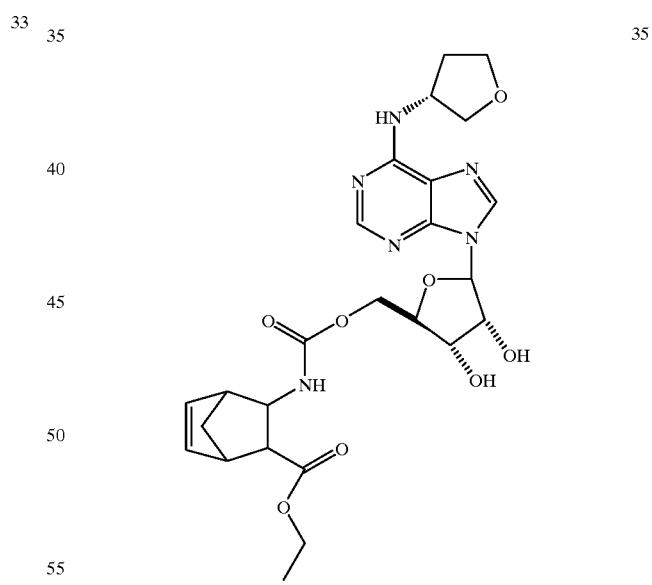

35

{(5-{6-[((3R)oxolan-3-yl)amino]purin-9-yl}(3S,2R,4R,5R)-3,4-dihydroxyoxolan-2-yl)methoxy]-N-cyclopropylcarboxamide(33) or ( 5'-O-[N-cyclopropylcarbamoyl]-6-[((3R)-tetrahydrofuranyl)] adenosine)

Ethyl 3-{[5-{6-[(3R)oxolan-3-yl)amino]purin-9-yl} (3S,2R,4R,5R)-3,4-dihydroxyoxolan-2-yl)methoxy] carbonylamino}(2S,3R)bicylo[2.2.1 hept-5-ene-2-carboxylate(35) or (5'-O-[N-2-(ethoxycarbonyl)(2S, 3R)bicyclo[2.2.1]hept-5-enylcarbamoyl]-6-[(3R)-tetrahydrofuranyl]adenosine)

This compound was prepared in a manner similar to that of 6, substituting cyclopropyl amine for methyl amine: 1H NMR (CDCl₃) 0.45 (m, 2H), 0.69 (m, 2H), 1.95 (m, 1H), 2.38 (m, 1H), 2.51 (m, 1H), 3.82–4.85 (m, 10H), 5.94 (d, 1H), 7.95 (s, 1H), 8.25 (s, 1H)].

This compound was prepared in a manner similar to that of 6, substituting 2-carboethoxy norbornm-5-enyl-2-amine for methyl amine: (M+1)=545.32

36

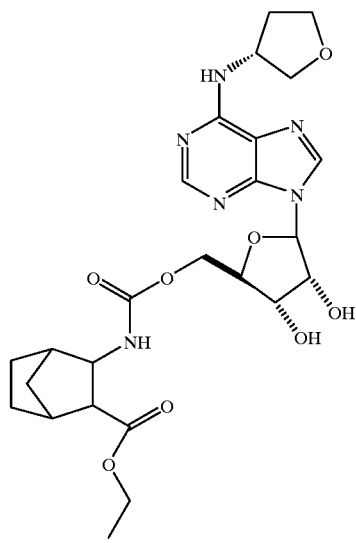

Ethyl 3-{[5-{6-[(3R)oxolan-3-yl)amino]purin-9-yl}
(3S,2R,4R,5R)-3,4-dihaydroxyoxolan-2-yl)
methoxyl]carbonylamino}(2S,3R)bicylo[2.2.1]
heptane-2-carboxylate(36) or (5'-O-[N-2-
(ethoxycarbonyl)(2S,3R)bicyclo[2.2.1]
heptylcarbamoyl]-6-[(3R)-tetrahydrofuranyl]
adenosine)

This compound was prepared in a manner similar to that of 6, substituting 3-carboethoxy norborn-5-yl-2-amine for methyl amine: (M+1)=547.38

37

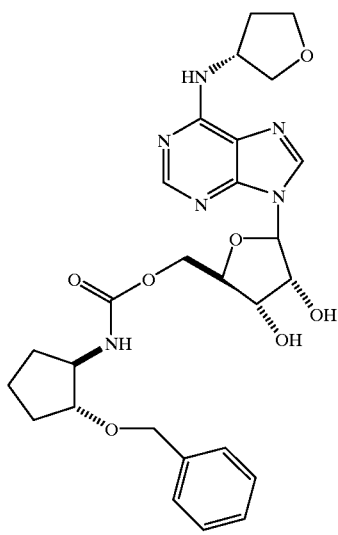

{(5-{6[((3R)oxolan-3-yl)amino]purin-9-yl}(3S,2R,
4R,5R)-3,4-dihydroxyoxolan-2-yl)methoxy]-N-[(1R,
2R)-2-(phenylmethoxy)cyclopentyl]carboxamide
(37) or (5'-O-[N-(2R)-benzyloxy-(1R)-
cyclopentylcarbamoyl]-6-[((3R)-tetrahydrofuranyl)]
adenosine)

This compound was prepared in a manner similar to that of 6, substituting (1R,2R)-2-benzyloxycyclopentyl amine for methyl amine: (M+1)=555.50

38

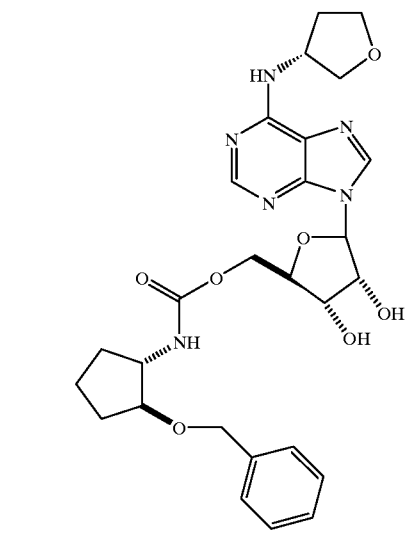

{(5-{6[((3R)oxolan-3-yl)amino]purin-9-yl}(3S,2R,
4R,5R)-3,4-dihydroxyoxolan-2-yl)methoxy]-N-[(1S,
2S)-2-(phenylmethoxy)cyclopentyl]carboxamide(38)
or ( 5'-O-[N-(2S)-benzyloxy-(1S)-
cyclopentylcarbamoyl]-6-[((3R)tetrahydrofuranyl)]
adenosine)

This compound was prepared in a manner similar to that of 6, substituting (1S,2S)-2-benzyloxycyclopentyl amine for methyl amine: (M+1)=555.50

39

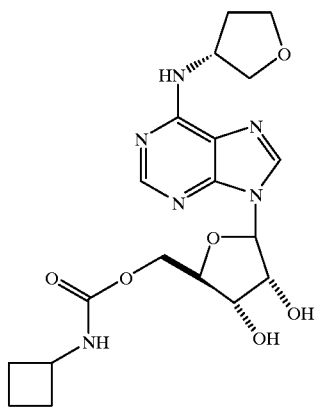

[(5-{6-[((3R)oxolan-3-yl)amino}purin-9-yl}(3S,2R,
4R,5R)-3,4-dihydroxyoxolan-2-yl)methoxy]-N-
cyclobutylcarboxamide(39) or (5'-O-[N-
cyclobutylcarbamoyl]-6-[((3R)-tetrahydrofuranyl)]
adenosine)

This compound was prepared in a manner similar to that of 6, substituting cyclobutyl amine for methyl amine: (M+1)=435.46.

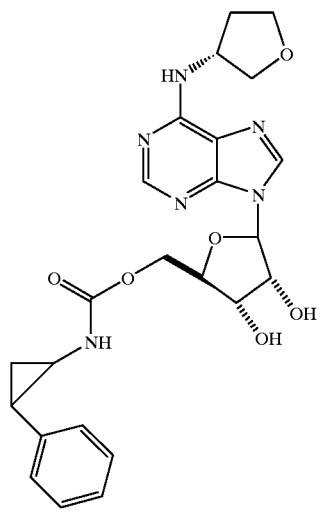

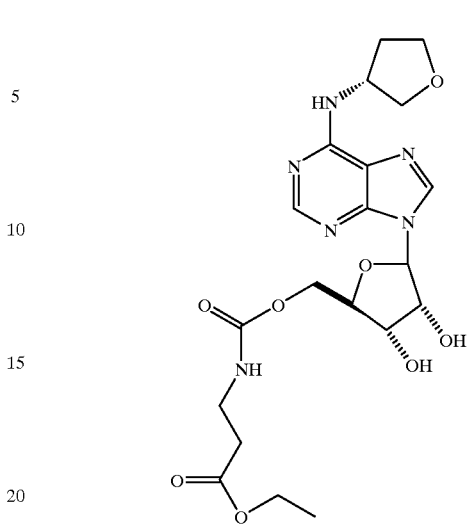

[(5-{6-[((3R)oxolan-3-yl)amino}purin-9-yl}(3S,2R, 4R,5R)-3,4-dihydroxyoxolan-1-yl)methoxy]-N-(2-phenylcyclopropyl)carboxamide(40) or (5'-O-[N-2-phenyl-1-cyclopropylcarbamoyl]-6-[((3R) tetrahydrofuranyl)]adenosine)

This compound was prepared in a manner similar to that of 6, substituting 2-phenylcyclopropyl amine for methyl amine: (M+1)=497.50

Ethyl 3-{[(5-16-[((3R)oxolan-3-yl)amino]purin-9-yl}(3S,2R,4R,5R)-3,4-dihydroxyoxolane-2-yl) methoxy}carbonylamino}propanoate(42) or (5'-O-[N-2-(ethoxycarbonyl)ethylcarbamoyl]-6-[((3R) tetrahydrofuranyl)]adenosine)

This compound was prepared in a manner similar to that of 6, substituting ethyl 3-aminopropionate for methyl amine: (M+1)=481.37

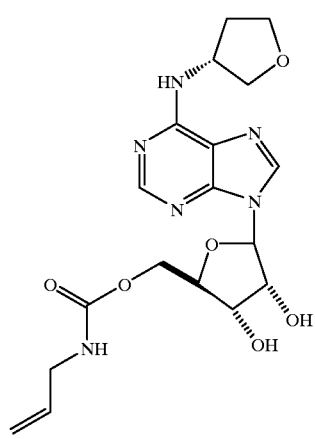

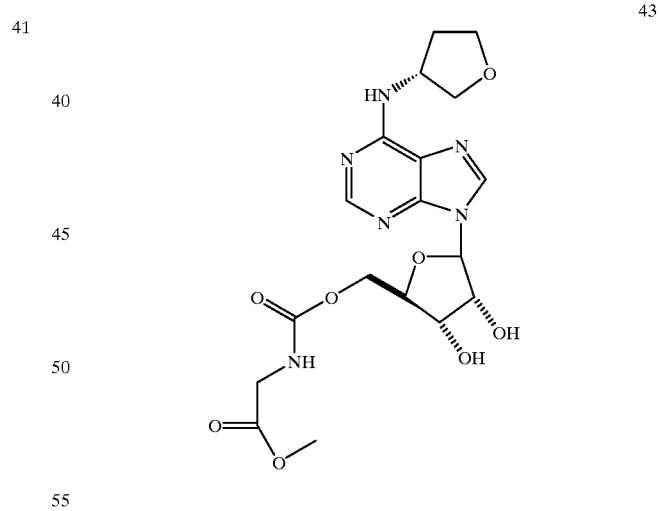

[(5-{6-[((3R)oxolan-3-yl)amino]purin-9-yl}(3S,2R, 4R,5R)-3,4-dihydroxyoxolan-2-yl)methoxy]-N-prop-2-enylcarboxamide(41) or (5'-O-[N-alkylcarbamoyl]-6-[((3R)tetrahydrofuranyl)] adenosine)

This compound was prepared in a manner similar to that of 6, substituting allyl amine for methyl amine: (M+1)= 421.39

Methyl 2-{[(5-{6-[((3R)oxolan-3-yl)amino]purin-9-yl}(3S,2R,4R,5R)-3,4-dihydroxyoxolane-2-yl) methoxy}carbonylamino}acetate(43) or (5'-O-[N-1-(methoxycarbonyl)methylcarbamoyl]-6-[((3R) tetrahydrofuranyl)]adenosine)

This compound was prepared in a manner similar to that of 6, substituting methyl 2-aminoacetate for methyl amine: (M+1)=453.39

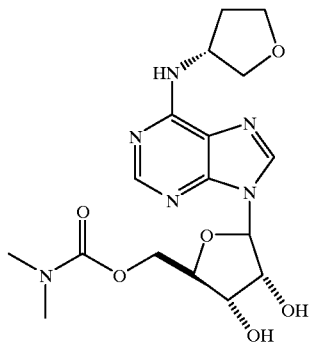

{(5-{6-[((3R)oxolan-3-yl)amino]purin-9-yl}(3S,2R, 4R,5R)-3,4-dihydroxyoxolan-2-yl)methoxy]-N,N-dimethylcarboxamide(44) or (5'-O-[N,N-dimethylcarbamoyl]-6-[((3R)tetrahydrofuranyl)] adenosine)

Compound 44 was prepared in a manner similar to compound 6 substituting N,N-dimethyl amine for methyl amine $^1$H NMR (CDCl$_3$): 1.95 (m, 1H), 2.36 (m, 1H), 2.75 (s, 3H), 2.85 (s, 3H), 3.85–4.84 (m, 10H), 5.95 (d, 1H), 7.95 (1H), 8.25 (s, 1H).

EXAMPLE 2

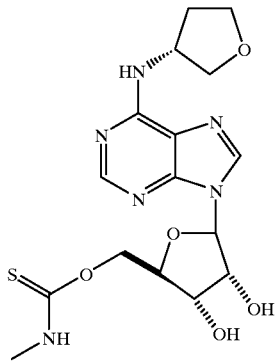

2-{6-[((3R)oxolan-3-yl)amino]purin-9-yl}(4S,2R, 3R,5R)-5-{1(methylamino)thioxomethoxy] methyl}oxolane-3,4-diol(45) or (5'-O-[N-methylthionocarbamoyl]-6-[((3R)tetrahydrofuranyl)] adenosine)

This compound was prepared in a manner similar to that of 6, substituting thiocarbonyl diimidazole(thioCDI) for carbonyl diimidazole(CDI): (M+1)=411.30

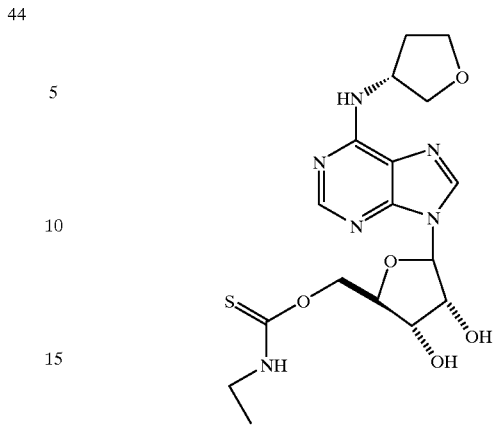

2-{6-[((3R)oxolan-3-yl)amino]purin-9-yl}(4S,2R, 3R,5R)-5-{[(ethylamino)thioxomethoxy] methyl}oxolane-3,4-diol(46) or (5'-O-[N-ethylthiomocarbamoyl]-6-[((3R)tetrahydrofuranyl)] adenosine)

This compound was prepared in a manner similar to that of 6, substituting thiocarbonyl diimidazole(thioCDI) for carbonyl diimidazole(CDI) and ethyl amine for methyl amine: (M+1)=425.30

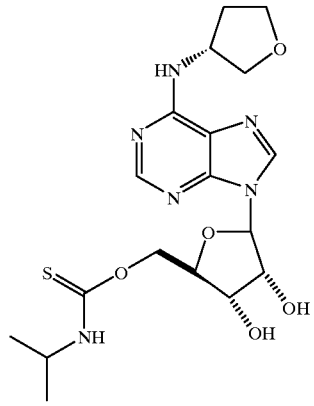

2-{6-[((3R)oxolan-3-yl)amino]purin-9-yl}(4S,2R, 3R,5R)-5-({[(methylethyl)amino] thioxomethoxy}methyl)oxolane-3,4-diol(47) or (5'-O-[N-Isopropylthionocarbamoyl]-6-[((3R) tetrahydrofuranyl)]adenosine)

This compound was prepared in a manner similar to that of 6, substituting thiocarbonyl diimidazole(thioCDI) for carbonyl diimidazole(CDI) and i-propyl amine for methyl amine: (M+1)=439.30

48

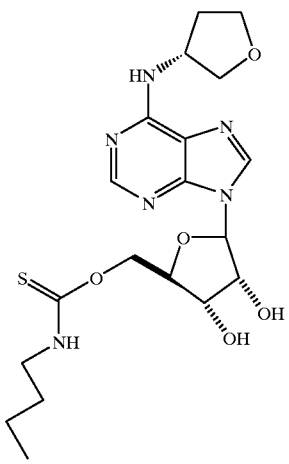

2-{6-[((3R)oxolan-3-yl)amino]purin-9-yl}(4S,2R, 3R,5R)-5-{[(butylamino)thioxomethoxy] methyl}oxolane-3,4-diol(48) or (5'-O-[N-butylthionocarbamoyl]-6-((3R)tetrahydrofuranyl) adenosine)

This compound was prepared in a manner similar to that of 6, substituting thiocarbonyl diimidazole(thioCDI) for carbonyl diimidazole(CDI) and n-butyl amine for methyl amine: (M+1)=453.30

49

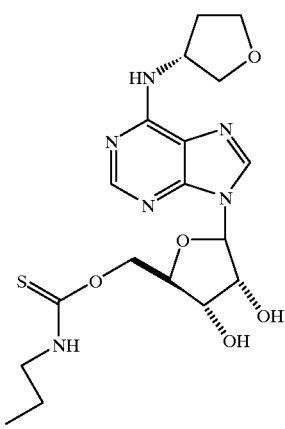

2-{6-[((3R)oxolan-3-yl)amino]purin-9-yl}(4S,2R, 3R,5R)-5-{[(propylamino)thioxomethoxy] methyl}oxolane-3,4-diol(49) or (5'-O-[N-propylthionocarbamoyl]-6-((3R)-tetrahydrofuranyl) adenosine)

This compound was prepared in a manner similar to that of 6, substituting thiocarbonyl diimidazole(thioCDI) for carbonyl diimidazole(CDI) and n-propyl amine for methyl amine: (M+1)=439.30

50

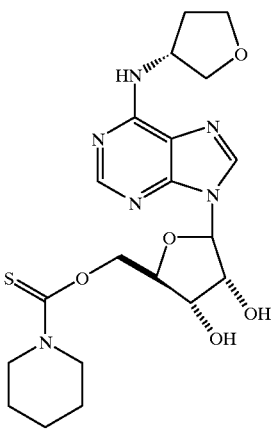

2-{6-[(3R)oxolan-3-yl)amino]purin-9-yl}(4S,2R,3R, 5R)-5-[(piperidylthioxomethoxy)methyl]oxolane-3, 4-diol(50) or (5'-O-[N-piperidinothionocarbamoyl]-6-((3R)tetrahydrofuranyl)adenosine)

This compound was prepared in a manner similar to that of 6, substituting thiocarbonyl diimidazole(thioCDI) for carbonyl diimidazole(CDI) and piperidine for methyl amine: (M+1)=46 5.30

51

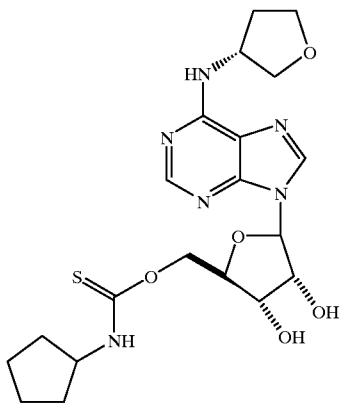

2-{6-[((3R)oxolan-3-yl)amino]purin-9-yl}(4S,2R, 3R,5R)-5-{[(cyclopentylamino)thioxomethoxy] methyl}oxolane-3,4-diol(51) or (5'-O-[N-cyclopentylthionocarbamoyl]-6-((3R) tetrahydrofuranyl)adenosine)

This compound was prepared in a manner similar to that of 6, substituting thiocarbonyl diimidazole(thioCDI) for carbonyl diimidazole(CDI) and cyclopentyl amine for methyl amine: (M+1)=465.30

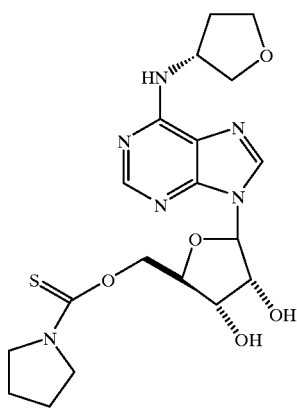

2-{6-[((3R)oxolan-3-yl)amino]purin-9-yl}(4S,2R, 3R,5R)-5-[(pyrrolidinylthioxomethoxy)methyl] oxolane-3,4-diol(52) or (5'-O-[N-pyrrolidinothionocarbamoyl]-6-((3R) tetrahydrofuranyl)adenosine)

This compound was prepared in a manner similar to that of 6, substituting thiocarbonyl diimidazole(thioCDI) for carbonyl diimidazole(CDI) and pyrrolidine for methyl amine: (M+1)=451.30

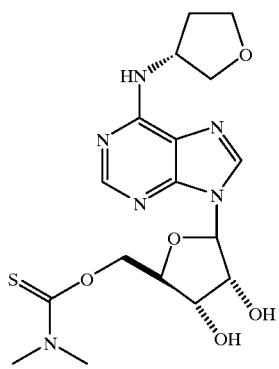

2-{6-[((3R)oxolan-3-yl)amino]purin-9-yl}(4S,2R, 3R,5R)-5-{[(dimethylamino)thioxomethoxy] methyl}oxolane-3,4-diol(53) or (5'-O-[N,N-dimethylthionocarbamoyl]-6-((3R)tetrahydrofuranyl) adenosine)

This compound was prepared in a manner similar to that of 6, substituting thiocarbonyl diimidazole(thioCDI) for carbonyl diimidazole(CDI) and N,N-dimethyl amine for methyl amine: (M+1)=425.30

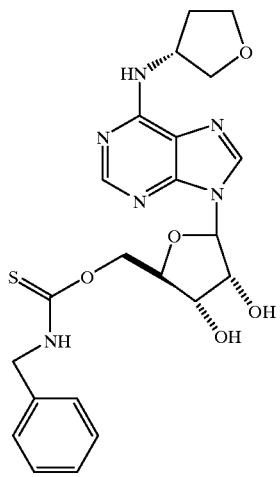

2-{6-[((3R)oxolan-3-yl)amino]purin-9-yl}(4S,2R, 3R,5R)-5-({[benzylamino]thioxomethoxy}methyl) oxolane-3,4-diol(54) or (5'-O-[N-benzylthionocarbamoyl]-6-((3R)tetrahydrofuranyl) adenosine)

This compound was prepared in a manner similar to that of 6, substituting thiocarbonyl diimidazole(thioCDI) for carbonyl diimidazole(CDI) and benzyl amine for methyl amine: (M+1)=487.30

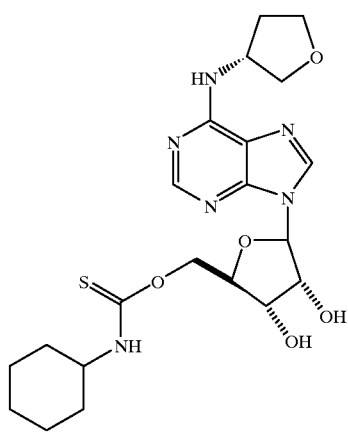

2-{6-[((3R)oxolan-3-yl)amino]purin-9-yl}(4S,2R, 3R,5R)-5-({[cyclohexylamino] thioxomethoxy}methyl)oxolane-3,4-diol(55) or (5'-O-[N-cyclohexylthionocarbamoyl]-6-((3R) tetrahydrofuranyl)adenosine)

This compound was prepared in a manner similar to that of 6, substituting thiocarbonyl diimidazole(thioCDI) for carbonyl diimidazole(CDI) and cyclohexyl amine for methyl amine: (M+1)=479.30

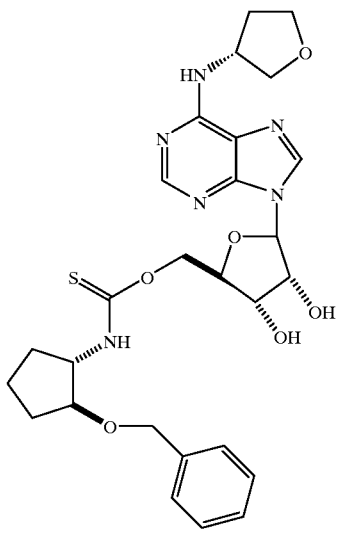

2-{6-[((3R)oxolan-3-yl)amino]purin-9-yl}(4S,2R, 3R,5R)-5-[({[(1S,2S)-2-(phenylmethoxy) cyclopentyl]amino}thioxomethoxy)methyl]oxolane-3,4-diol(56) or (5'-O-[N-(2S)benzyloxy-(1S) cyclopentylthionocarbamoyl]-6-[(3R)-tetrahydrofuranyl]adenosine)

This compound was prepared in a manner similar to that of 6, substituting thiocarbonyl diimidazole(thioCDI) for carbonyl diimidazole(CDI) and (1S,2S)-2-benzyloxycyclopentyl amine for methyl amine: (M+1)= 571.47

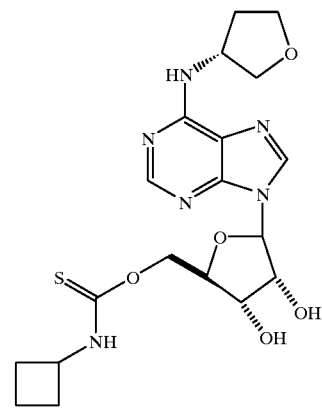

2-{6-[((3)oxolan-3-yl)amino]purin-9-yl}(4S,2R,3R, 5R)-5-{[(cyclobutylamino)thioxomethoxy] methyl}oxolane-3,4-diol(58) or (5'-O-[N-cyclobutylthionocarbamoyl]-6-((3R) tetrahydrofuranyl)adenosine)

This compound was prepared in a manner similar to that of 6, substituting thiocarbonyl diimidazole(thioCDI) for carbonyl diimidazole(CDI) and cyclobutyl amine for methyl amine: (M+1)=451.44

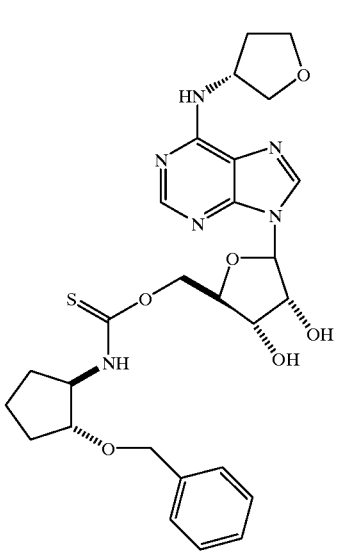

2-{6-[((3R)oxolan-3-yl)amino]purin-9-yl}(4S,2R, 3R,5R)-5-[({[(1R,2R)-2-(phenylmethoxy) cyclopentyl]amino}thioxomethoxy)methyl]oxolane-3,4-diol(57) or (5'-O-[N-(2R)benyzloxy-(1S)]-6-[(3R)-tetrahydrofuranyl]adenosine)

This compound was prepared in a manner similar to that of 6, substituting thiocarbonyl diimidazole(thioCDI) for carbonyl diimidazole(CDI) and (1R,2R)-2-benzyloxycyclopentyl amine for methyl amine: (M+1)= 571.47

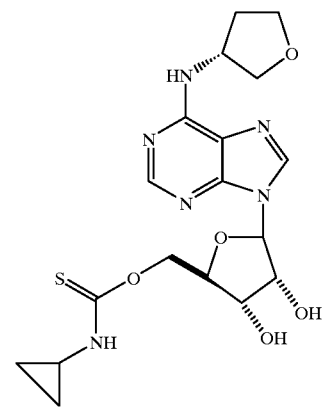

2-{6-[((3R)oxolan-3-yl)amino]purin-9-yl}(4S,2R, 3R,5R)-5-{[(cyclopropylamino)thioxomethoxy] methyl}oxolane-3,4-diol(59) or (5'-O-[N-cyclopropylthionocarbamoyl]-6-((3R) tetrahydrofuranyl)adenosine)

This compound was prepared in a manner similar to that of 6, substituting thiocarbonyl diimidazole(thioCDI) for carbonyl diimidazole(CDI) and cyclopropyl amine for methyl amine: (M+1)=437.43.

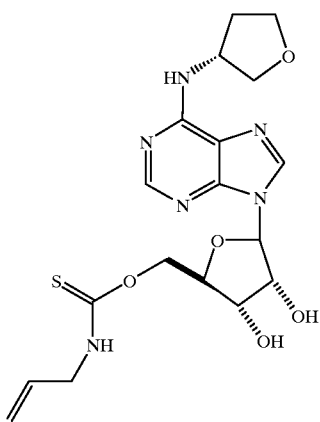

60

2-(6-[((3R)oxolan-3-yl)amino]purin-9-yl}(4S,2R,3R,
5R)-5-{[(prop-2-enylamino)thioxomethoxyl]
methyl}oxolane-3,4-diol(60) or (5'-O-[N-
alkylthionocarbamoyl]-6-((3R)tetrahydrofuranyl)
adenosine)

This compound was prepared in a manner similar to that of 6, substituting thiocarbonyl diimidazole(thioCDI) for carbonyl diimidazole(CDI) and allyl amine for methyl amine: (M+1) 437.43.

EXAMPLE 3

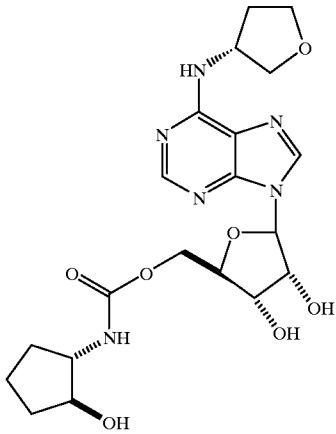

61

((5-(6[((3R)oxolan-3-yl)amino]purin-9-yl}(3S,2R,
4R,5R)-3,4-dihydroxyoxolan-2-yl)methoxy]-N-((1S,
2S)-2-hydroxycyclopentyl)carboxamide(61) or (5'-
O-[N-(2S)-hydroxy-(1S)-cyclopentylcarbamoyl]-6-
[((3R)-tetrahydrofuranyl)]adenosine)

Compound 38 (25 mg), ethanol (5 mL), cyclohexene (5 mL), and palladium hydroxide on carbon (50 mg) were mixed and refluxed for 48 h. The catalyst was filtered through celite by gravity filtration and the solvent was removed under reduced pressure to give 61: (M+1)=465.29

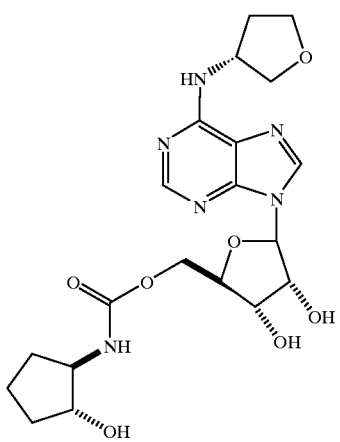

62

{(5-{6[((3R)oxolan-3-yl)amino]purin-9-yl}(3S,2R,
4R,5R)-3,4-dihydroxyoxolan-2-yl)methoxy]-N-((1R,
2R)-2-hydroxycyclopentyl)carboxamide(62) or (5'-
O-[N-(2R)-hydroxy-(1R)-cyclopentylcarbamoyl]-6-
((3R)-tetrahydrofuranyl)adenosine)

This compound was prepared from 37 using the procedure similar to that used for 61: (M+1)=465.29

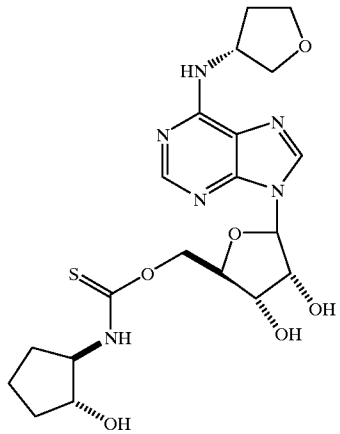

63

2-{6-[((3R)oxolan-3-yl)amino]purin-9-yl}(4S,2R,
3R,5R)-5-({[((1R,2R)-2-hydroxycyclopentyl)amino]
thioxomethoxy}methyl)oxolane-3,4-diol(63) or (5'-
O-[N-(2R)-hydroxy-(1R)-
cyclopentylthionocarbamoyl]-6-((3R)-
tetrahydrofuranyl)adenosine)

This compound was prepared from 57 using the procedure similar to that used for 61: (M+1) 465.29.

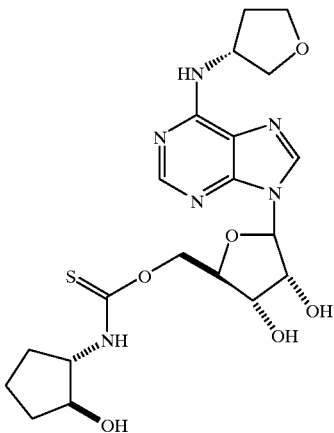

64

2-{6-[((3R)oxolan-3-yl)amino]purin-9-yl}(4S,2R,
3R,5R)-5-({[((1R,2R)-2-hydroxycyclopentyl)amino]
thioxomethoxy}methyl)oxolane-3,4-diol(64) or (5'-
O-[N-(2S)-hydroxy-(1S)-
cyclopentylthionocarbamoyl]-6-((3R)
tetrahydrofuranyl)adenosine)

This compound was prepared from 56 using the procedure similar to that used for 61: (M+1)=465.29.

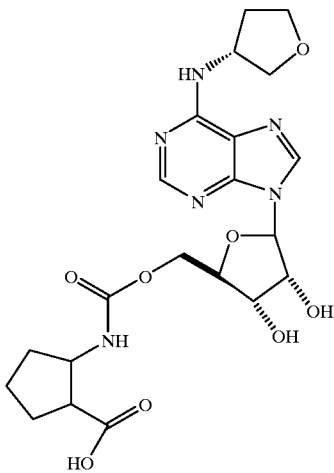

65

EXAMPLE 4

2-{[5-{6-[(3R)oxolan-3-yl)amino]purin-9-yl}(3S,
2R,4R,5R)-3,4-dihydroxyoxolan-2-yl)methoxy]
carbonylamino}cyclopentanecarboxylic acid (65) or
(5'-O-[N-2-(hydroxycarbamoyl)
cyclopentylcarbamoyl]-6-[((3R)-tetrahydrofuranyl)]
adenosine)

To a cooled (0° C.) solution of ester 34 (12 mg) in 2:1 THF:H2O (2 mL) was added 3eq. of lithium hydroxide monohydrate (2M solution in water). The reaction was allowed to stir at 0° C. for 2 hours, then allowed to warm to room temperature for 30 minutes. After all the ester was consumed as judged by TLC, amberlite resin (approximately 4 mg) was added and the solution was filtered through a cotton plug. Evaporation of solvent gave the pure acid 65: (M+1) 493.33

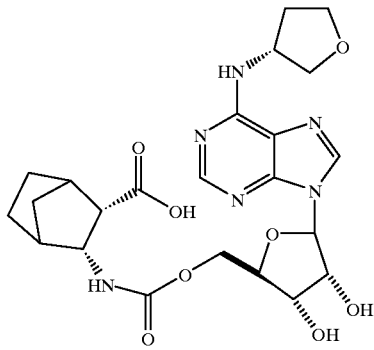

66

3-{[(5-{6-[((3R)oxolan-3-yl)amino]purin-9-yl}(3S,
2R,4R,5R)-3,4-dihydroxyoxolan-2-yl)methoxy]
carbonylamino}(2S,3R)bicyclo[2.2.1]hept-5-ene-2-
carboxylic acid (66) or (5'-O-[N-2-
hydroxycarbamoyl](2S,3R)bicyclo[2.2.1]hept-5-
enylcarbamoyl]-6-[((3R)-tetrahydrofuranyl)]
adenosine)

This compound was prepared from compound 35 using the procedure similar to that used for 65: (m+1)=517.35

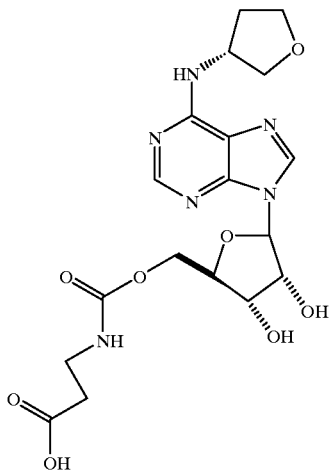

67

3-{[(5-{6-[((3R)oxolan-3-yl)amino]purin-9-yl}(3S,
2R,4R,5R)-3,4-dihydroxyoxolan-2-yl)methoxy]
carbonylamino}propanoic acid(67) or (5'-O-[N-2-
(hydroxycarbonyl)ethylcarbamoyl]-6-[((3R)-
tetrahydrofuranyl)]adenosine)

This compound was prepared from compound 42 using the procedure similar to that used for 65: (m+1)=453.32

68

2-{[(5-{6-[((3R)oxolan-3-yl)amino]purin-9-yl}(3S, 2R,4R,5R)-3,4-dihydroxyoxolan-2-yl)methoxyl] carbonylamino}acetic acid(68) or (5'-O-[N-1-(hydroxycarbonyl)methylcarbamoyl]-6-[((3R)-tetrahydrofuranyl]adenosine This compound was prepared from compound 43 using the procedure similar to that used for 65: (m+1)=439.30

EXAMPLE 5

7

5-{6-[((3R)oxolan-3-yl)amino]purin-9-yl}(2R,3R, 4R,5R)-4-acetyloxy-2-[(N-methylcarbamoyloxy) methyl]oxolan-3-ylacetate(7) or (2',3'-O-diocetoxy-5'-O-[N-methylcarbamoyl]-6-[((3R)-tetrahydrofuranyl)]adenosine)

To a solution of compound 6 (70 mg) and dimethylaminopyridine (50 mg) in pyridine (2 mL) at 23° C. was added acetic anhydride (0.1 mL). After 3 h at 23° C., the reaction was concentrated in vacuo. The residue was dissolved in methylene chloride (50 mL), washed with water (3×10 mL), and dried (Na$_2$SO$_4$). After concentration in vacuo, the residue was purified by flash chromatography (methylene chloride: methanol 20:1 followed by 9:1) to afford compound 7 (70 mg): $^1$H NMR (CDCl$_3$) 1.95–2.00 (m, 1H), 2.02 (s, 3H), 2.05 (s, 3H), 2.15–2.25 (m, 1H), 2.40 (s, 3H), 3.75–3.85 (m, 1H), (m, 2H), 4.30–4.45 (m, 3H), 4.80–4.95 (m, 1H), 5.40 (bs, 1H), 5.60–5.62(m, 1H), 5.80–5.82(m, 1H), 6.206.02 (m, 1H), 6.80–6.90 (bs, 1H), 8.00 (s, 1H), 8.35 (s, 1H).

EXAMPLE 6

10

2-{6-[((3R)oxolan-3-yl)amino]-2-chloropurin-9-yl} (4S,2R,3R,5R)-5-(hydroxymethyl)oxolane-3,4-diol (10) or (2-chloro-6-[((3R)-tetrahydrofuranyl)] adenosine)

Compound 8 was prepared from 1,2,3,4-tetra-O-acetylribofuranoside 2 and 2,6-dichloropurine following the procedure reported in the literature (John A. Montgomery et.al. J. Heterocycl. Chem. 1964, 213.) A mixture of compound 8 (1.g, 2.24 mmol) and (R)-3-amino tetrahydrofuran (tosylate salt) (0.75 g, 3 mmol) in methanol were stirred for 16 h. Methanol was evaporated under reduced pressure and the residue was filtered through a plug of silica gel to give a gom. An NMR spectrum of this gum showed peaks corresponding to compound 9. This material was used without further purification in the next reaction.

To the material from the previous reaction, methanolic ammonia (0.5 M, 20 mL) was added and stirred for 16 h at room temperature. The solvent was removed under reduced pressure and the residue was purified by silica gel column chromatography (10% methanol-ethyl acetate) to give compund 10 as a white solid: $^1$H NMR (CD$_3$OD) 1.95–2.5 (m, 1H), 2.30–2.40 (m, 1H), 3.70–3.80 (m, 2H), 3.80–3.90 (m, 2H), 3.95–4.05 (m, 2H), 4.15–4.17 (m, 1H), 4.28–4.30 (m, 1H), 4.65 (t, 1H), 4.70–4.80 (m, 1H), 5.90 (d, 1H), 8.25 (s, 1H).

11

(4-{6-[((3R)oxolan-3-yl)amino]-2-chloropurin-9-yl} (1R,2R,4R,5R)-7,7-dimethyl-3,6,8-trioxabicyclo [3.3.0]oct-2-yl)methan-1-ol(11) or (2-Chloro-6 [(3R)-tetrahydrofuranyl]-2',3'-isopropylidino-adenosine)

To a solution of compound 1 (0.36, 1 mmol)) and 2,2-dimethoxypropane (0.2 g, 2 mmol) in dimethylformamide (5 mL) was added p-toluenesulfonic acid (10 mg) at 70° C. After 48 h at 70° C., the reaction was concentrated in vacuo to afford a solid. The solid was dissolved in methanol (1 mL), then triturated with ethyl ether (50 mL). The resultant crystals were collected by vacuum filtration to afford the intermediate 11.

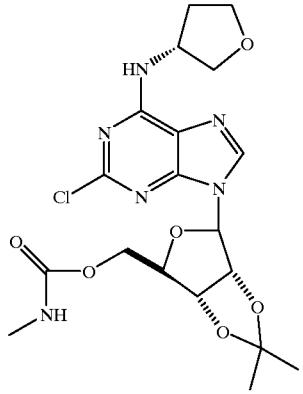

[(4-{6-[((3R)oxolan-3-yl)amino]-2-chloropurin-9-yl}(1R,2R,4R,5R)-7,7-diamethyl-3,6,8-trioxabicyclo[3.3.0]oct-2-yl)methoxy]-N-methylcarboxamide(12) or (2-Chloro-5'[N-methylcarboxamido]-6[(3R)-tetrahydrofuranyl]-2',3'-isopropylidino-adenosine)

To a solution of compound 11 (90 mg, 0.25 mmol) in THF (1 mL) was added carbonyldiimidazole (162 mg, 1 mmol) at rt. After stirring for 2 h , excess reagent was quenched by adding a drop of water. Methylamine (40% aq. Solution, 0.5 mL) was added and stirring was continued for another 16 h. The reaction mixture was concentrated in vacuo to afford a gum. It was purified by prep.TLC [(silica gel, 10% MeOH-dichloromethane)] to afford compound 12.

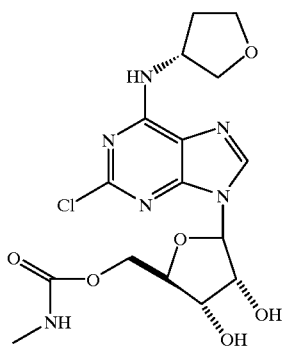

[(5-{6-[((3R)oxolan-3-yl)amino]-2-chloropurin-9-yl}(3S,2R,4R,5R)-3,4-dihydroxyoxolan-2-yl) methoxy]-N-methylcarboxamide (13) or 2-chloro-5'-O-[N-methylcarbamoyl]-6-[((3R)-tetrahydrofuranyl)]adenosine Compound 12 (50 mg) was taken in a mixture of acetic acid (8 mL) and water (2 mL) and heated at 90° C. for 16 h. Solvents were removed under reduced pressure and the residue was purified by preparative TLC [methanol-dichloromethane (1:9)] to afford compound 13. $^1$H NMR (CD$_3$OD) 1.95–2.05 (m, 1H), 2.30–2.40 (m, 1H), 2.70 (s, 3H), 3.70–3.80 (m, 1H), 3.80–3.90 (m, 1H), 3.95–4.05 (m, 2H), 4.20–4.40 (m, 4H), 4.65 (t, 1H), 4.70–4.80 (m, 1H), 5.95 (d, 1H), 6.90 (bs, exchangeable, 1H), 8.20 (s, 1H).

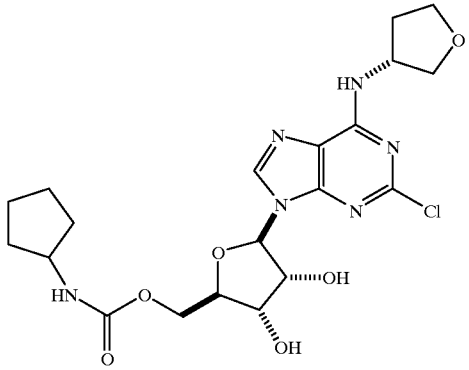

[(5-{6-[((3R)oxolan-3-yl)amino]-2-chloropurin-9-yl}(3S,2R,4R,5R)-3,4-dihydroxyoxolan-2-yl) methoxy]-N-cyclopentylcarboxamide(69) or (2-chloro-5'-O-[N-cyclopentylcarbamoyl]-6-[((3R)-tetrahydrofuranyl)]adenosine)

This compound was prepared in a manner similar to that of 13 substituting cyclopentyl amine for methyl amine: $^1$H NMR (CD$_3$OD) 1.4–1.5 (m, 2H), 1.5–1.6 (m, 2H), 1.6–1.7 (m, 2H), 1.8–1.9 (m, 2H), 1.95–2.05 (m, 1H), 2.30–2.40 (m, 1H), 3.70–3.80 (m, 1H), 3.80–3.90 (m, 2H), 3.95–4.05 (m, 2H), 4.20–4.40 (m, 4H), 4.65 (t, 1H), 4.65–4.80 (m, 1H), 5.95 (d, 1H), 8.15 (s, 11H).

EXAMPLE 7

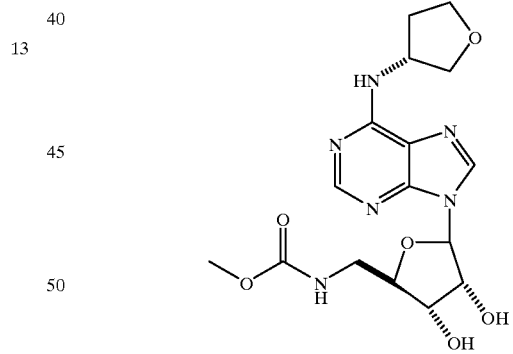

N-[(5-{6-[((3R)oxolan-3-yl)amino]purin-9-yl}(3S, 2R,4R,5R)-3,4-dihydroxyoxolan-2-yl)methy] methoxycarboxamide (18) or (Nor-5'-hydroxy-5'-(methoxycarbonylamino)-6-[(3R)-tetrahydrofuranyl] adenosine)

Compound 14 (1.4 g, 3.07 mmol) was dissolved in dry DMF and sodium azide (3.00 g, 4.6 mmol) was added and heated at 65° C. for 16 h. The solvent was evaporated and the residue was subjected to aqueous work up and purified by flash column (100% ethyl acetate) to get 15.

A solution of 15 (314 mg) in ethanol containing 10% Pd-C (100 mg) in an atmosphere of hydrogen was stirred at room temperature for 16 h. Filtration followed by the evaporation of solvent gave compound 16.

CDI (100 mg) was added to 3 mL of dry methanol and stirred at room temeprature for 15 min. The solvent was evaporated and the residue was dissolved in dry THF (5 mL). Compound 16 (25 mg) was added to the solution and the mixture was stirred at room temperature for 16 h. The solvent on evaporation followed by preparative TLC (5% MeOH: 95% DCM) purification gave the compound 17. Deprotection of 17 with 80% aqueous acetic acid followed by evaporation and purification by preparative TLC (5% MeOH: 95% DCM) gave compound 18 [MS 395.2 (M+1)].

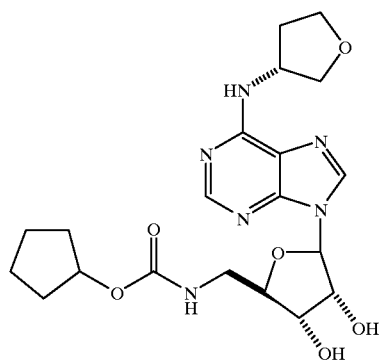

70

N-[(5-{6-[((3R)oxolan-3-yl)amino]purin-9-yl}(3S, 2R,4R,5R)-3,4-dihydroxyoxolan-2-yl)methy] cyclopentyloxycarboxamide(70) or (Nor-5'- hydroxy-5'-(cyclopentyloxycarbonylamino)-6-[(3R)- tetrahydrofuranyl]adenosine)

Compound 70 was prepared as described above in Example 7 substituting cyclopentanol for methanol [MS 489.3 (M+1)].

EXAMPLE 8

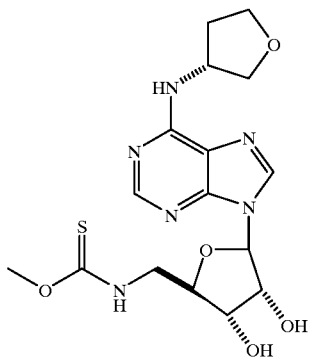

71

2-{6-[((3R)oxolan-3-yl)amino]purin-9-yl}(4S,2R, 3R,5R)-5-{[methoxythioxomethyl)amino] methyl}oxolane-3,4-diol(71) or (Nor-5'-hydroxy- (methoxythionocarbamoylamino)-6-[((3R)- tetrahydrofuranyl)]adenosine)

Compound 71 was prepared as described in Example 7 substituting thioCDI for CDI [MS 411.2 (M+1)].

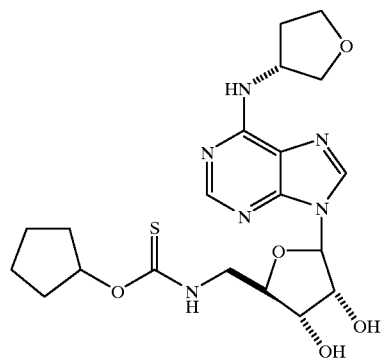

72

2-{6-[((3R)oxolan-3-yl)amino]purin-9-yl}(4S,2R, 3R,5R)-5-{[cyclopentyloxythioxomethyl)amino] methyl}oxolane-3,4-diol (72) or (Nor-5'-hydroxy-5' (cyclopentyloxythionocarbamoyl amino)-6-[((3R)- tetrahydrofuranyl)]adenosine)

Compound 72 was prepared as described in Example 7 substituting thioCDI for CDI and cyclopentanol for methanol [MS 465.7 (M+1)].

EXAMPLE 9

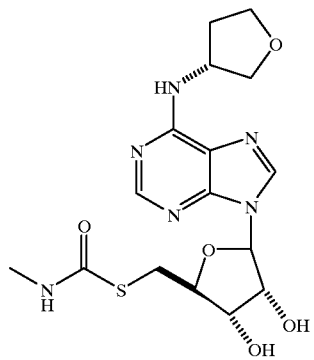

22

[(5-{6-[((3R)oxolan-3-yl)amino]purin-9-yl}(2S,3S, 4R,5R)-3,4-dihydroxyoxolan-2-yl)methythio]-N- methylcarboxamide( 22) or (Nor-5'-hydroxy-5'- (methylaminocarbonylthio)-6-[((3R)- tetrahydrofuranyl))]adenosine)

To a solution of compound 15 (455 mg) in acetone (30 mL) potassium thioacetate was added and refluxed for 16 h. The reaction mixture was cooled and the solvent was evaporated. Purification of the residue by flash column chromatography (100% ethyl acetate) gave compound 19.

Sodium methoxide in methanol (0.5M; 9 mL) was added to 19 (570 mg) and the resulting solution was stirred under nitrogen at room temperature for 4 h. An aliquot of the reaction mixture was worked up and the product was analyzed by NMR to see the disappearance of the acetate peak (2.3 ppm). The reaction mixture was subjected to aqueous work up and the product was extracted with DCM. Care was taken to purge the solvents, that are used for the work up, with nitrogen for at least 30 min to minimize the oxidation of thiol to the disulfide. The organic layer on evaporation gave compound 20.

Nitrogen was bubbled for 30 min through 10 mL of acetonitrile containing about 2 mg of DMAP. Compound 20 was added to the above solution followed by the addition of methyl isocyanate. The mixture was stirred at room temperature for 16 h under nitrogen. The completion of the reaction was checked by TLC (5% MeOH: 95% DCM). Purification of the residue obtained by the evaporation of the reaction mizture gave compound 22 [MS 411.2 (M+1)].

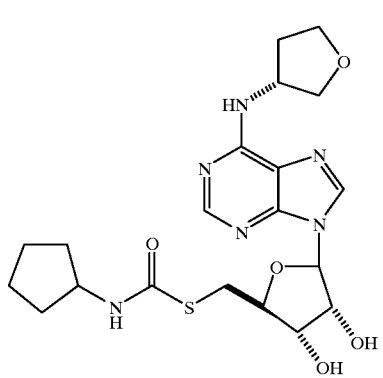

73

[(5-{6-[((3R)oxolan-3-yl)amino]purin-9-yl}(2S,3S, 4R,5R)-3,4-dihydroxyoxolan-2-yl)methythio]-N-cyclopentylcarboxamide(73) or (Nor- 5'-hydroxy-5'-(cyclopentylaminocarbonylthio)-6-[((3R)-tetrahydrofuranyl)]adenosine)

Compound 73 was prepared in the manner of compound 22 by substituting cyclopentyl isocyanate for methyl isocyanate [MS 465.2 (M+1)].

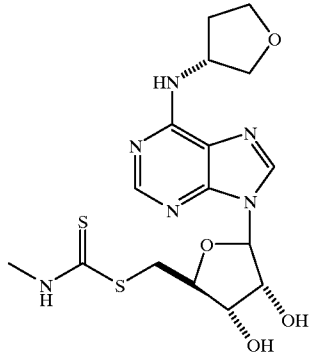

74

2-{6-[((3R)oxolan-3-yl)amino]purin-9-yl}(4S,5S, 2R,3R)-5-{[(methylamino)thioxomethylthio] methyl}oxolane-3,4-diol(74) or (Nor-5'-hydroxy-5' (methylaminothionocarbonylthio)-6-[((3R)-tetrahydrofuranyl)]

Compound 74 was prepared in the manner compound 22 by substituting methyl isothiocyanate for methyl isocyanate [MS 427.2 (M+1)].

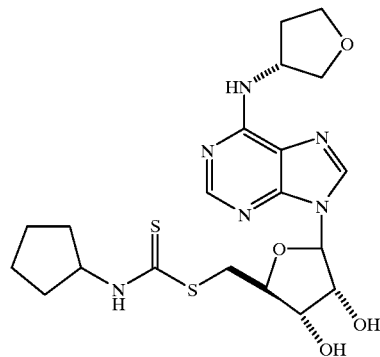

75

2-{6-[((3R)oxolan-3-yl)amino]purin-9-yl}(4S,5S, 2R,3R)-5-{[(cyclopentylamino)thioxomethy] thiolmethyl}oxolane-3,4-diol(75) or (Nor-5'-hydroxy-5'-(cyclopentylaminothionocarbonylthio)-6-[(3R)-tetrahydrofuranyl]adenosine)

Compound 75 was prepared in the manner of compound 22 by substituting cyclopentyl isothiocyanate for methyl isocyanate [MS 481.2 (M+1)].

EXAMPLE 10

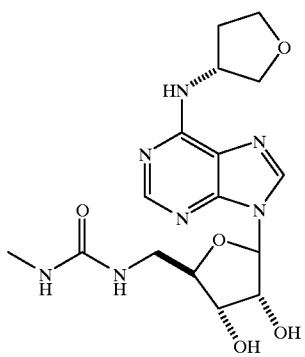

24

N-[(5-{6-[((3R)oxolan-3-yl)amino]purin-9-yl}(3S, 2R,4R,5R)-3,4-dihydroxyoxolan-2-yl)methyl] (methylamino)carboxamide(24) or (Nor-5'-hydroxy-5'-(methylaminocarbonylaza)-6-[((3R)-tetrahydrofuranyl)]adenosine)

To a solution of 16 (30 mg) in acetonitrile a small amount (2 mg) of DMAP followed by methyl isocyanate (250 $\mu$L) was added and stirred at room temperature for 16 h. The solvent was evaporated and the residue was purified by preparative TLC (5% MeOH : 95% DCM) to obtain compound 23. Deprotection of 22 with 80% aqueous acetic acid followed by preparative TLC purification (5% MeOH: 95% DCM) gave compound 24 [MS 394.2 (M+1)].

76

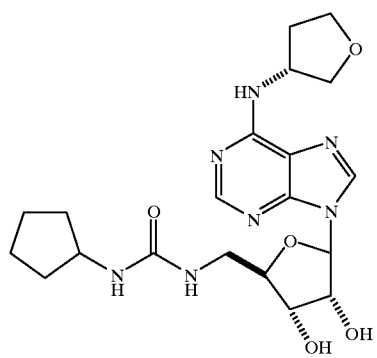

N-[(5-{6-[((3R)oxalan-3-yl)amino]purin-9-yl}(3S, 2R,4R,5R)-3,4-dihydroxyoxolan-2-yl)methyl] (cyclopenthylamino)carboxamide(76) or (Nor-5'-hydroxy-5'-(cyclopenthylaminocarbonylaza)-6-[((3R)-tetrahydrofuranyl)]adenosine)

Compound 76 was prepered in the manner of compound 24 substituting cyclopentyl isocyanate for methyl isocyanate and refluxing for 16 h [MS 448.3 (M+1)].

78

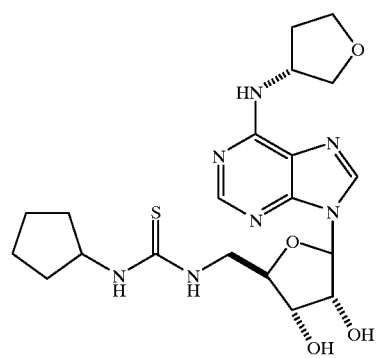

2-{6-[((3R)oxolan-3-yl)amino]purin-9-yl}(4S,2R, 3R,5R)-5-({[(cyclopentylamino)thioxomethyl] amino}methyl)oxolane-3,4-diol (78) or (Nor-5'-hydroxy-5'-(cyclopentylthiocarbonylaza)-6-[((3R)-tetrahydrofuranyl)]adenosine)

Compound 78 was prepared in the manner of compound 24 substituting cyclopentyl isothiocyanate for methyl isocyanate and refluxing for 16 h [MS 464.3 (M+1)].

77

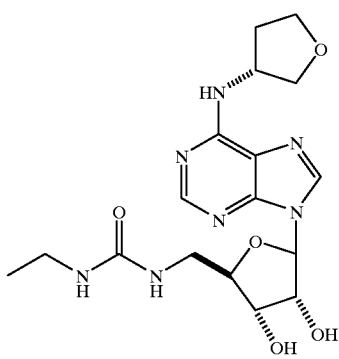

2-{6-[((3R)oxolan-3-yl)amino]purin-9-yl}(4S,2R, 3R,5R)-5-({[(methylamino)thioxomethyl] amino}methyl)oxolane-3,4-diol(77) or (Nor-5'-hydroxy-5'-(methylaminothionocarbonylaza)-6-[((3R)-tetrahydrofuranyl)]adenosine)

Compound 77 was prepared in the manner of compound 24 substituting methyl isothiocyanate for methyl isocyanate and refluxing for 16 h [MS 410.3 (M+1)].

79

N-[(5-{6-[((3R)oxolan-3-yl)amino]purin-9-yl}(3S, 2R,4R,5R)-3,4-dihydroxyoxolan-2-yl)methyl] (ethylamino)carboxamide (79) or (Nor- 5'-hydroxy-5'-(ethylaminocarbonylaza)-6-[((3R)-tetrahydrofuranyl)]adenosine)

Compound 79 was prepared in the manner of compound 24 substituting ethyl isocyanate for methyl isocyanate and refluxing for 16 h [MS 408 (M+1)].

EXAMPLE 11

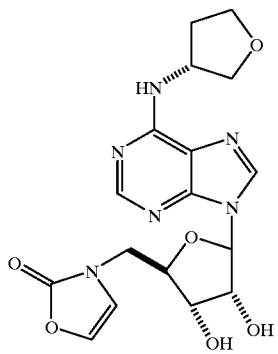

3-[(5-{6-[((3R)oxolan-3-yl)amino]purin-9-yl}(3S, 2R,4R)-3,4-dihydroxyoxolan-2-yl)methyl]-1,3-oxazolin-2-one(80) or (Nor-5'-hydroxy-5'-(N-1,3-oxazolin-2-onyl)-6-[(3R)-tetrahydrofuranyl)] adenosine)

Sodium hydride (40 mg, 60% in mineral oil) was added to a solution of oxazolidinone (85 mg, 1 mmol) in anhydrous DMF (2 mL). To this was added a solution of compound 15 (100 mg) in DMF (2 mL). Reaction mixture was allowed to stir at RT for 3 h. The solvent was removed under reduced pressure, the residue was dissolved in 80% acetic acid/water and heated at 80° C. for 16 h. Solvent was removed under reduced pressure and the residue was purified by preparative TLC (10% methanol-dichloromethane) to give compound 80 as a solid: (M+1)=405.38.

EXAMPLE 12

Binding Assays—$DDT_1$ Cells

Cell Culture

DDT cells (hamster vas deferens smooth muscle cell line) were grown as monolayers in petri dishes using Dulbecco's Modified Eagle's Medium (DMEM) containing 2.5 $\mu$g ml$^{-1}$ amphotericin B, 100 U ml$^{-1}$ penicillin G, 0.1 mg ml$^{-1}$ streptomycin sulfate and 5% fetal bovine serum in a humidified atmosphere of 95% air and 5% $CO_2$. Cells were subcultured twice weekly by dispersion in Hank's Balanced Salt Solution (HBSS) without the divalent cations and containing 1 mM EDTA. The cells were then seeded in growth medium at a density of 1.2×10$^5$ cells per plate and experiments were performed 4 days later at approximately one day preconfluence.

Membrane Preparations

Attached cells were washed twice with HBSS (2×10 ml), scraped free of the plate with the aid of a rubber policeman in 5 ml of 50 mM Tris-HCl buffer pH 7.4 at 4° C. and the suspension homogenized for 10 s. The suspension was then centrifuged at 27,000×g for 10 min. The pellet was resuspended in homogenization buffer by vortexing and centrifuged as described above. The final pellet was resuspended in 1 vol of 50 mM Tris-HCl buffer pH 7.4 containing 5 mM $MgCl_2$ for $A_1$ AdoR assays. For the [$^{35}$S]GTPγS binding assay the final pellet was resuspended in 50 mM Tris-HCl pH 7.4 containing 5 mM $MgCl_2$, 100 mM NaCl and 1 mM dithiothreitol. This membrane suspension was then placed in liquid nitrogen for 10 min, thawed and used for assays. The protein content was determined by the method of Bradford (1976) using bovine serum albumin as standard.

Competitive Binding Assay

Pig striatum were prepared by homogenation in 50 mM Tris buffer (5×volume of tissue mass pH=7.4). After centrifugation at 19,000 rpm for 25 minutes at 4° C., the supernatant was discarded, and the process was repeated twice. Compositions of this invention were assayed to determine their affinity for the $A_1$ receptor in a pig striatum membrane prep or a $DDT_1$ membrane prep. Briefly, 0.2 mg of pig striatal membranes or $DDT_1$ cell membranes were treated with adenosine deaminase and 50 mM Tris buffer (pH=7.4) followed by mixing. To the pig membranes was added 2 $\mu$L of serially diluted DMSO stock solution of the compounds of this invention at concentrations ranging from 100 microM to 10 nM. The control received 2 microL of DMSO alone, then the antagonist [$^3$H] 8-cyclopentylxanthine (CPX) for pig striatum or the agonist [$^3$H] 2-chloro-6-cyclopentyladenosine (CCPA) for DDT, membranes in Tris buffer (50 mM, pH of 7.4) was added to achieve a final concentration of 2 nM. After incubation at 23 C for 2 h, the solutions were filtered using a membrane harvester using multiple washing of the membranes (3×). The filter disks were counted in scintillation cocktail affording the amount of displacement of tritiated CPX or by the competitive binding compositions of this invention. In the case of the $DDT_1$ cell membranes, some of the determinations of binding affinity ($K_i$) were made in the presence of Gpp(NH)p as noted in Table 1 (note: Gpp(NH)p shifts the receptor to a low affinity form). Greater than a 5 point curve was used to generate $K_i$'s and the number of experiments is indicated in the column marked in Table 1 below.

TABLE 1

| Compound # | $K_i$ - $DDT_1$ cell membrane | $K_i$ - $DDT_1$ cell membrane In presence of Gpp (NH)p | $K_i$ - Pig Striatum |
|---|---|---|---|
| 41 | 668 nM | — | — |
| 39 | 447 nM | — | — |
| 39 | 447 nM | — | — |
| 61 | 1571 nM | — | — |
| 43 | 1700 nM | — | — |
| 35 | 1012 nM | — | — |
| 56 | 1236 nM | — | — |
| 69 | 380 nM | — | — |
| 42 | 3145 nM | — | — |
| 62 | 2191 nM | — | — |
| 36 | 1517 nM | — | — |
| 37 | 4236 nM | — | — |
| 34 | 3464 nM | — | — |
| 6 | 178 nM | — | 228 nM |
| 77 | 113 nM | — | — |
| 78 | 357 nM | — | — |
| 76 | 11590 nM | — | — |
| 13 | 129 nM | — | — |
| 73 | 183 nM | — | — |
| 75 | 62 nM | — | — |
| 22 | 36 nM | — | — |
| 67 | 2219 nM | — | — |
| 22 | 36 nM | — | — |
| 75 | 62 nM | — | — |
| 69 | 380 nM | — | — |
| 45 | — | 141 nM | — |
| 46 | — | 135 nM | — |
| 49 | — | 145 nM | — |
| 47 | — | 109 nM | — |
| 48 | — | 926 nM | — |
| 25 | — | 727 nM | — |
| 27 | 1611 nM | 1111 nM | — |
| 26 | — | 513 nM | — |
| 32 | — | 431 nM | — |
| 54 | — | 229 nM | — |
| 60 | — | 239 nM | — |

TABLE 1-continued

| Compound # | $K_i$ - $DDT_1$ cell membrane | $K_i$ - $DDT_1$ cell membrane In presence of Gpp (NH)p | $K_i$ - Pig Striatum |
|---|---|---|---|
| 53 | 245 nM | 2109 nM | — |
| 51 | — | 87 nM | — |
| 55 | 252 nM | 962 nM | — |
| 52 | — | 1120 nM | — |
| 50 | 642 nM | 1946 nM | — |
| 31 | — | 1091 nM | — |
| 44 | — | 1841 nM | — |
| 33 | — | 1713 nM | — |
| 30 | 2212 nM | 1732 nM | — |
| 29 | — | 478 nM | — |
| 79 | — | 1671 nM | — |
| 28 | 321 nM | 808 nM | — |

EXAMPLE 13

[$^{35}$S]GTPγS Binding Assays $A_1$-agonist stimulated [$^{35}$S]GTPγS binding was determined by a modification of the method described by Giersckik et al. (1991) and Lorenzen et al. (1993). Membrane protein (30–50 μg) was incubated in a volume of 0.1 ml containing 50 mM Tris-HCl buffer pH 7.4, 5 mM $MgCl_2$, 100 mM NaCl, 1 mM dithiothreitol, 0.2 units $ml^{-1}$ adenosine deaminase, 0.5% BSA, 1 mM EDTA, 10 mM GDP, 0.3 nM [$^{35}$S]GTPγS and with or without varying concentrations of CPA for 90 min at 30° C. Nonspecific binding was determined by the addition of 10 μM GTPγS. Agonist stimulated binding was determined as the difference between total binding in the presence of CPA and basal binding determined in the absence of CAP. Previous reports have shown that agonist stimulated [$^{35}$S]GTPγS binding was dependent on the presence of GDP (Gierschik et al., 1991; Lorenzen et al., 1993; Traynor & Nahorski, 1995). In preliminary experiments, it was found that 10 μM GDP gave the optimal stimulation of CPA dependent [$^{35}$S]GTPγS binding and this concentration was therefore used in all studies. In saturation experiments, 0.5 nM [$^{35}$S]GTPγS was incubated with 0.5–1000 nM GTPγS. At the end of the incubation, each suspension was filtered and the retained radioactivity determined as described above.

TABLE 2

| Compound # | GTPγS |
|---|---|
| CPA | 100% |
| 41 | 48% |
| 39 | 67% |
| 63 | 100% |
| 64 | 99% |
| 71 | 98% |
| 74 | 95% |
| 72 | 93% |
| 59 | 82% |
| 65 | 81% |
| 80 | 80% |
| 72 | 93% |
| 18 | 77% |
| 70 | 76% |
| 58 | 79% |
| 57 | 67% |
| 39 | 67% |
| 61 | 59% |
| 43 | 53% |
| 35 | 52% |

TABLE 2-continued

| Compound # | GTPγS |
|---|---|
| 56 | 52% |
| 69 | 50% |
| 42 | 47% |
| 62 | 42% |
| 36 | 41% |
| 37 | 30% |
| 34 | 17% |
| 38 | 1% |
| 40 | −6% |
| 6 | 48% |
| 77 | 101% |
| 78 | 95% |
| 13 | 77% |
| 73 | 109% |
| 75 | 91% |
| 22 | 98% |
| 67 | 59% |
| 68 | 76% |
| 22 | 98% |
| 75 | 91% |
| 69 | 50% |
| 45 | 77% |
| 45 | 77% |
| 46 | 77% |
| 49 | 89% |
| 47 | 84% |
| 48 | 70% |
| 25 | 80% |
| 27 | 44% |
| 26 | 73% |
| 32 | 91% |
| 54 | 93% |
| 60 | 77% |
| 53 | 85% |
| 55 | 82% |
| 52 | 77% |
| 50 | 88% |
| 30 | 41% |
| 28 | 69% |

EXAMPLE 14 cAMP Assay

A scintillation proximity assay (SPA) using rabbit antibodies directed at cAMP using an added tracer of adenosine 3',5'-cyclic phosphoric acid 2'-O-succinyl-3-[$^{125}$I] iodotyrosine methyl ester and fluoromicrospheres containing anti-rabbit specific antibodies as described by Amersham Pharmacia Biotech (Biotrak cellular communication assays). Briefly, $DDT_1$ cells were cultured in clear bottomed 96 well microtiter plates with opaque wells at concentrations between $10^4$ to $10^6$ cells per well in 40 μl of HBSS at 37° C. (5% $CO_2$ and 95% humidity). The partial or full $A_1$ agonists (5 μl) of this invention were incubated at various concentrations with the $DDT_1$ cells in the presence of rolipram (50 μM), and 5 μM forskolin for 10 min at 37° C. The cells were immediately lysed by treatment 5 μl of 10% dodecyltrimethylammonium bromide followed by shaking using microplate shaker. After incubation of the plate for 5 minutes, an immunoreagent solution (150 μl containing equal volumes of tracer, antiserum, and SPA fluorospheres) was added to each well followed by sealing the plate. After 15–20 h at 23° C., the amount of bound [125I] cAMP to the fluoromicrospheres was determined by counting in a microtitre plate scintillation counter for 2 minutes. Comparison of counts with standard curves generated for cAMP using a similar protocol afforded the cAMP present after cell lysis. Results are presented normalized to the full agonist N-6-cyclopentyladenosine, CPA. Thus, the full agonist CPA diminished the amount of forskolin induced cAMP generation back to basal levels.

TABLE 3

| Compound # | cAMP |
|---|---|
| CPA | 100% |
| 41 | 17% |
| 39 | 45% |
| 63 | 115% |
| 64 | 110% |
| 71 | 94% |
| 74 | 82% |
| 72 | 103% |
| 58 | 78% |
| 59 | 115% |
| 65 | 95% |
| 80 | 64% |
| 72 | 103% |
| 18 | 86 |
| 70 | 79% |
| 57 | 73% |
| 39 | 45% |
| 61 | 53% |
| 43 | 28% |
| 35 | −4% |
| 56 | 43% |
| 69 | 18% |
| 42 | 16% |
| 62 | 23% |
| 36 | 10% |
| 37 | −6% |
| 34 | −20% |
| 38 | −25% |
| 40 | −14% |
| 6 | See FIG. |
| 69 | 18% |

EXAMPLE 15

Methods

Guinea pigs of either sex weighing 250–300 g were anesthetized with methoxyflurane and killed by cervical dislocation. The hearts were quickly removed and rinsed in ice-cold Krebs-Henseleit solution. The aorta was cannulated and the heart retrogradely perfused at a constant flow of 10 ml min$^{-1}$ with modified Krebs-Henseleit solution containing (mM): NaCL 117.9, KCl 4.8, $CaCl_2$ 2.5, $MgSO_4$ 1.18, $KH_2PO_4$ 1.2, $Na_2EDTA$ 0.5, ascorbic acid 0.14, glucose 5.5, pyruvic acid (sodium salt) 2.0, and $NaHCO_3$ 25. The K—H solution was oxygenated with 95% oxygen and 5% $CO_2$, pH 7.4, and temperature maintained at 36° C.

Hearts were electrically paced at a cycle length of 290–300 ms (unless otherwise indicated) using a bipolar electrode placed on the right atrium or ventricle. The stimulator, an interval generator (Model 1830, WPI, Sarasota, Fla., U.S.A.) delivered stimuli through a stimulus isolation unit (Model 1880, WPI) as square wave pulses of 3 ms in duration and at least twice the threshold intensity. The stimulus-to-His bundle (S-H) interval was used as index of AV nodal conduction time and was measured on-line during constant atrial pacing from microcomputer with a DT-208 1A interface board (Axon Instruments, Burlingame, Calif., U.S.A.) In experiments to study the chronotropic effect (effect on heart rate) of $A_1$ AdoR agonists, the hearts were allowed to beat spontaneously. An atrial electrogram was used to record the electrical activity of the atria and to measure the heart rate.

Coronary perfusion pressure was measured using a pressure transducer that was connected to the aortic cannula via a T-connector. Coronary perfusion pressure (in mmHg) was monitored throughout an experiment and recorded on a 4-channel Gould strip-chart recorder (Gould RS3400, Cleveland, Ohio, U.S.A.). Coronary conductance (in ml min$^{-1}$ mmHg$^{-1}$) was calculated as the ratio of coronary perfusion rate (10 ml min$^{-1}$) and perfusion pressure (mmHg).

Monophasic action potentials (MAP) were recorded using a pressure contact silver-silver chloride electrode (Langendorf Probe, EP Technologies, Inc., Sunnyvale, Calif., U.S.A.) placed on the surface of the left atrium. The signals were amplified and filtered by an isolated biological amplifier (IsoDam, WPI) and displayed in real time on a digital oscilloscope (2201 Tektronix, Inc., Beaverton, Oreg., U.S.A.). Signals were considered adequate if they were stable for at least 5 min and the amplitudes of the MAPs exceeded 10 mV. The data were digitized at 2 kHz by a DT-2801A digitizing board (Data Translation, Marlboro, Mass., U.S.A.) and stored using the Snapshot data acquisition program (Snapshot Storage Scope, HEM Data Corp., Southfield, Mich., U.S.A.) for later analysis. The duration of the atrial monophasic action potential was measured at 90% repolarization ($MAPD_{90}$), using the Snapshot program. After completion of dissection and instrumentation, the hearts were allowed to equilibrate for 30 min before the experiments were begun. Whenever the baseline and post-intervention (washout) values differed by more than 15% the data were discarded. Approximately 60–70% of the experiments conformed with this criteria.

Partial $A_1$ (Results and discussion)

Figure 1B:
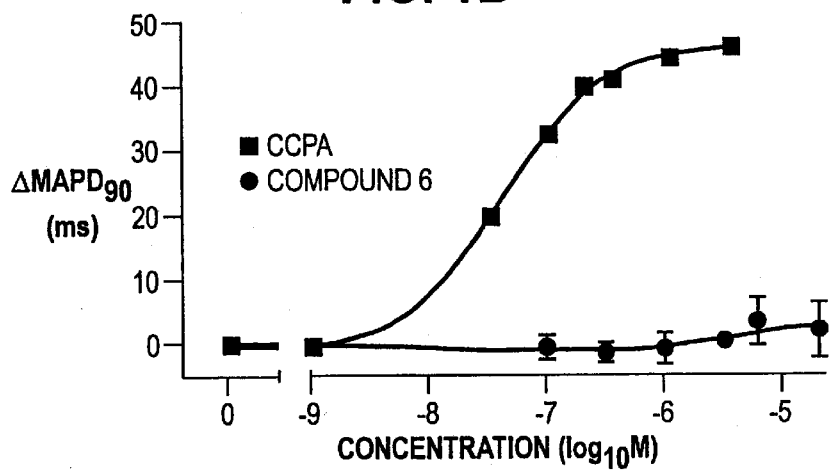
Figure 1C:
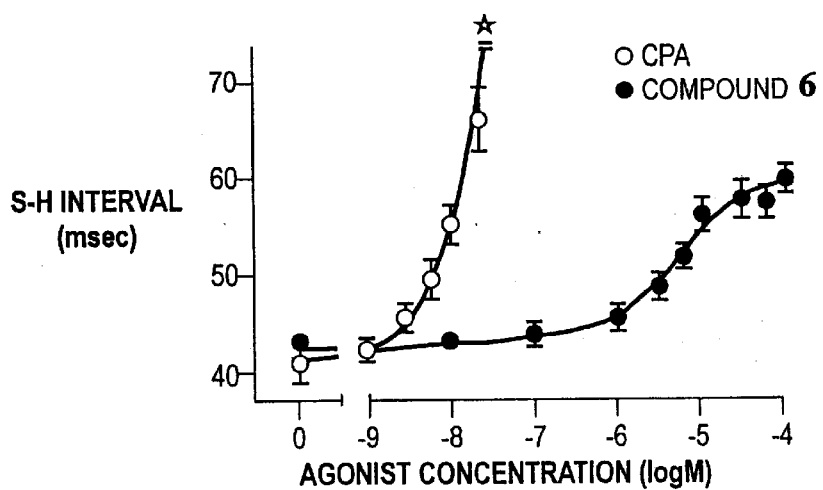
Figure 2:
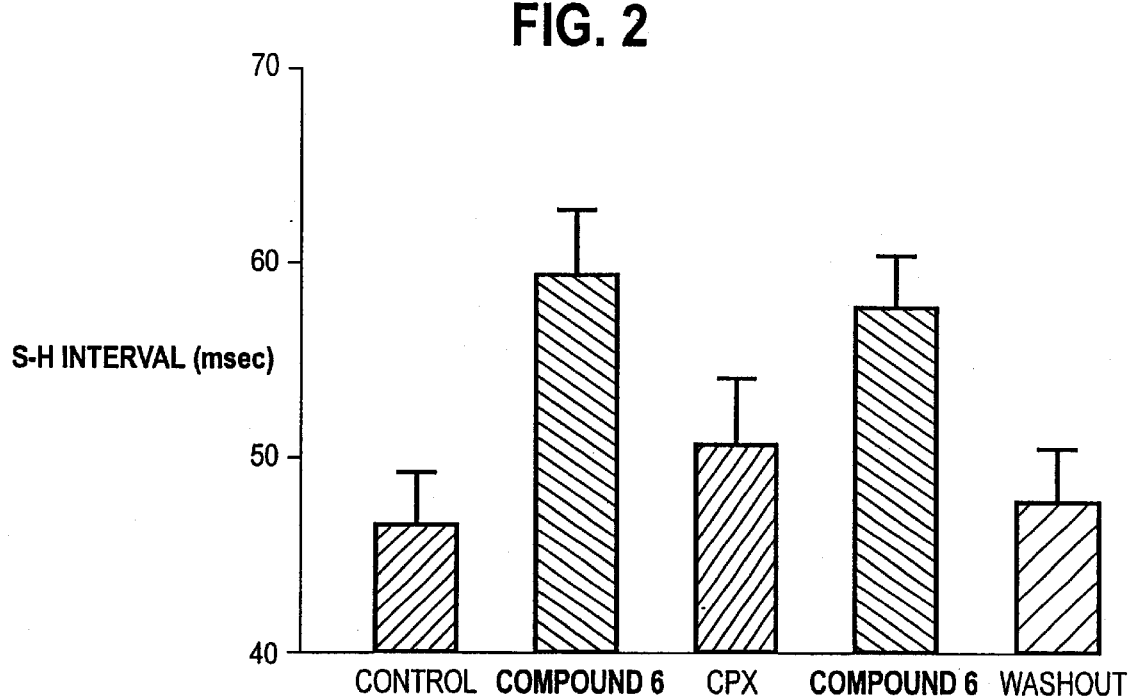
FIG. 2 is chart of antagonism by CPX (50 nM), an $A_1$ antagonist, of the prolongation of the stimulus to His-bundle interval (S-H interval) caused by Compound 6 in guinea pig isolated hearts paced at actual cycle length of 300 msec. Bars represent the means±SEM of single determinations from each of four hearts. The attenuation by CPX of the effect of Compound 6 was significant (P<0.05), indicating that Compound 6 acts by activating $A_1$ receptors in the AV node.
Figure 3:
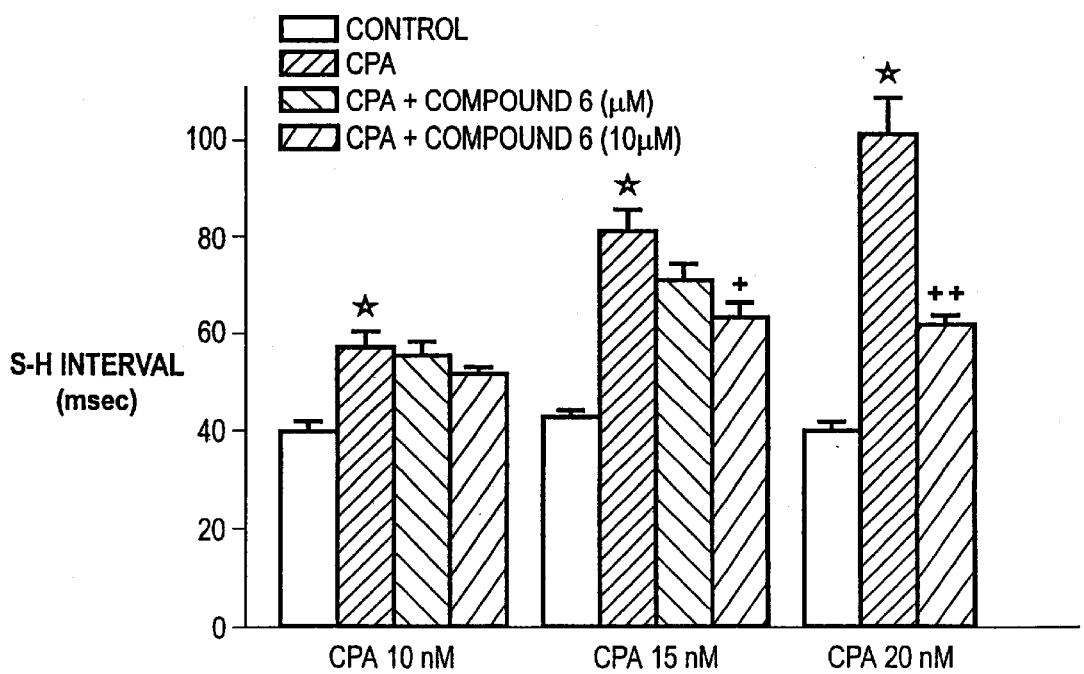
FIG. 3 is a chart representing antagonism by Compound 6 (2 and 10 μm) of the stimulus to His-bundle interval prolongation caused by the full agonist CPA in guinea pig isolated perfused hearts paced at an atrial cycle length of 300 msec. Bars represent the means±SEM of single determinations from each of four hearts.

The effects of compound 6 are illustrated in FIGS. 1–3. As illustrated in FIG. 1 (panel C) in guinea pig isolated perfused hearts, compound 6 causes a concentration-dependent and significant increase in AV nodal conduction time (measured as stimulus-to-His bundle interval) without causing second-degree AV block at any concentration tested. That is, compound 6 has a negative dromotropic effect (FIG. 1, panel C), and its potency ($EC_{50}$ value=concentration that causes half-maximal effect) to prolong S-H interval is 2.8±1.3 $\mu$M. The selective $A_1$ adenosine receptor antagonist CPX (50 nM) antagonizes the prolongation of S-H interval caused by compound 6 indicating that the effect of compound 6 is mediated by the $A_1$ adenosine receptor subtype (FIG. 2). On the other hand, compound 6 had no effect on other cardiac $A_1$ AdoR mediated actions of adenosine and full $A_1$ AdoR agonists (FIG. 1). Specifically, compound 6 did not slow heart rate (i.e, has no negative dromotropic effect; FIG. 1, panel A) or shorten the atrial monophasic action potential (FIG. 1, panel B). In contrast to compound 6 (as shown in FIG. 1), the full $A_1$ AdoR agonists CPA and CCPA slowed heart rate (panel A), shortened the monophasic atrial action potential (panel B), prolonged the S-H interval and caused second-degree AV block (panel C). Compound 6 had a weak potency ($EC_{50}$=31±5.1 $\mu$M) to cause coronary vasodilation, an $A_{2A}$ AdoR-mediated effect. Hence Compound 6 is at least 10-fold more potent (selective) to cause S-H interval prolongation than to increase coronary conductance. Another important pharmacological property of a true partial agonist (s) is to attenuate the effect(s) of a full agonist(s). In this regard, as shown in FIG. 3, compound 6 indeed antagonizes the negative dromotropic effect (S-H interval prolongation) of the full $A_1$ AdoR agonist CPA, a finding that strongly supports the conclusion that compound 6 is a true partial $A_1$ AdoR agonist.

In summary, compound 6 is a partial agonist of the A1 AdoR that causes moderate negative dromotropic effect without causing second- or third-degree AV block, bradycardia or shortening of atrial monophasic action potential.

What is claimed is:
1. A compound having the formula:

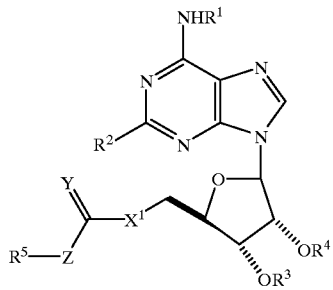

wherein $X^1=O, S, NR^6$; $Y=O, S, N—CN, N—OR^7$; $Z=O, S, NR^8$;

$R^1$ is a monocyclic group containing from 3 to 15 carbon atoms wherein one carbon atom is substituted with an atom or molecule selected from the group consisting of N, O, and S—$(O)_{0-2}$ and wherein $R^1$ does not contain an epoxide group;

$R^2$ is selected from the group consisting of hydrogen, halo, $CF_3$, and cyano;

$R^3$ and $R^4$ are each independently selected from the group consisting of hydrogen, and —(CO)—R' and —(CO)—R" wherein R', and R" are independently selected from the group consisting of $C_{1-15}$ alkyl, $C_{2-15}$ alkenyl, $C_{2-15}$ alkynyl, heterocyclyl, aryl, and heteroaryl, which alkyl, alkenyl, alkynyl, aryl, heterocyclyl, and heteroaryl are optionally substituted with 1 to 3 substituents independently selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and each optional heteroaryl, aryl, and heterocyclyl substituent is further optionally substituted with halo, $NO_2$, alkyl, $CF_3$, amino, mono- or di-alkylamino, alkyl or aryl or heteroaryl amide, $NR^{20}COR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2N(R^{20})_2$, CN, or $OR^{20}$;

$R^5$ is selected from the group consisting of $C_{1-5}$ alkyl, $C_{2-15}$ alkenyl, $C_{2-15}$ alkynyl, heterocyclyl, aryl, and heteroaryl, which alkyl, alkenyl, alkynyl, aryl, heterocyclyl and heteroaryl are optionally substituted with from 1 to 3 substituents independently selected from the group consisting of halo, alkyl, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $S(O)_3R^{20}$, $P(O)(OR^{20})_2$, $SO_2NR^{20}COR^{22}$, $SO_2NR^{20}CO_2R^{22}$, $SO_2NR^{20}CON(R^{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR_{20}SO_2R^{22}$, $OC(O)R^{20}$, $C(O)OCH_2OC(O)R^{20}$, and $OCON(R^{20})_2$ and each optional alkyl, heteroaryl, aryl, and heterocyclyl substituent is further optionally substituted with halo, $NO_2$, alkyl, $CF_3$, amino, mono- or di-alkylamino, alkyl or aryl or heteroaryl amide, $NR^{20}COR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $S(O)_3R^{20}$, $P(O)(OR^{20})_2$, $SR^{20}$, $S(O)R^{22}$, $SO_2R^{22}$, $SO_2N(R^{20})_2$, CN, or $OR^{20}$;

$R^6$ is selected from the group consisting of H, $C_{1-6}$ alkyl and aryl optionally substituted with halo, CN, $CF_3$, $OR^{20}$ and $N(R^{20})_2$;

$R^7$ and $R^8$ are each independently selected from the group consisting of H, and $C_1-C_{15}$ alkyl optionally substituted with one aryl substituent that is optionally substituted with halo or $CF_3$;

$R^{20}$ is selected from the group consisting of H, $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl; and $R^{22}$ is selected from the group consisting of hydrogen, $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from the group consisting of halo, alkyl, mono- or dialkylamino, alkyl or aryl or heteroaryl amide, CN, O—$C_{1-6}$ alkyl, $CF_3$, aryl, and heteroaryl wherein when $Z=NR^8$ then $R^5$ and $R^8$ may bond to form a 4 or 5 or 6 membered saturated or unsaturated ring; wherein when $X^1=NR^6$ and when $Z=NR^8$, then $R^6$ and $R^8$ may bond to form a 4 or 5 or 6 membered saturated or unsaturated ring; and wherein when $X^1=NR^6$ and $Y=O$ or S, then $R^5$ and $R^6$ may bond to form a 5 or a 6 membered saturated or unsaturated ring.

2. The compound of claim 1 wherein $Y=O, S$;

$R^2$ is selected from hydrogen, and halo;

$R^3$ and $R^4$ are independently selected from the group consisting of hydrogen, —(CO)—R' and —(CO)—R" wherein R', and R" are independently selected from the group consisting of $C_{1-15}$ alkyl, heterocyclyl, aryl, and heteroaryl, which alkyl, aryl, heterocyclyl, and heteroaryl are optionally substituted with from 1 to 2 substituents independently selected from the group consisting of halo, $NO_2$, heterocyclyl, aryl, heteroaryl, $CF_3$, CN, $OR^{20}$, $N(R^{20})_2$, $S(O)R^{22}$, $SO_2R^{22}$, $SO_2N(R^{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, and $NR^{20}SO_2R^{22}$ and wherein each optional heteroaryl, aryl, and heterocyclyl substituent is optionally substituted with halo, $NO_2$, alkyl, $CF_3$, amino, mono- or di-alkylamino, CN, or $OR^{20}$;

$R^5$ is selected from the group consisting of $C_{1-15}$ alkyl, $C_{2-15}$ alkenyl, $C_{2-15}$ alkynyl, hetcrocyclyl, aryl, and heteroaryl, which alkyl, alkenyl, alkynyl, aryl, heterocyclyl and heteroaryl are optionally substituted with from 1 to 3 substituents independently selected from the group consisting of halo, alkyl, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2S(O)_3R^{20}$, $P(O)(OR^{20})_2$, $NR^{20}COR^{22}$, $NR^{20}CO_2R^{22}$, $NR^{20}CON(R^{20})_2$, $COR^{20}$, $CO_2R^{20}$, and $CON(R^{20})_2$, and each optional alkyl, heteroaryl, and aryl substituent is optionally substituted with halo, alkyl, $CF_3$, $CO_2R^{20}$, $CON(R^{20})_2$, $NR^{20}CON(R^{20})_2$, $S(O)_3R^{20}$, $P(O)(OR^{20})_2$, $SR^{20}$, $S(O)R^{22}$, $SO_2R^{22}$, $SO_2N(R^{20})_2$, CN, or $OR^{20}$;

$R^{20}$ is selected from the group consisting of H, $C_{1-15}$ alkyl, aryl, and heteroaryl, which alkyl, aryl, and heteroaryl are optionally substituted with 1 to 2 substituents independently selected from the group consisting of halo, alkyl, aryl, mono- or dialkylamino, CN, O—$C_{1-6}$ alkyl, and $CF_3$; and $R^{22}$ is selected from the group consisting of hydrogen, $C_{1-15}$ alkyl, aryl, and heteroaryl, which alkyl, aryl, and heteroaryl are optionally substituted with 1 to 2 substituents independently selected from the group consisting of halo, alkyl, mono- or dialkylamino, CN, O—$C_{1-6}$ alkyl, and $CF_3$ wherein when Z=$NR^8$ then $R^5$ and $R^8$ may bond to form a 4 or 5 or 6 membered saturated or unsaturated ring; wherein when $X^1$=$NR^6$ and when Z=$NR^8$, then $R^6$ and $R^8$ may bond to form a 4 or 5 or 6 membered saturated or unsaturated ring; and wherein when $X^1$=$NR^6$ and Y=O or S, then $R^5$ and $R^6$ may bond to form a 5 or a 6 membered saturated or unsaturated ring.

3. The compound of claim 1 wherein Y=O, S;

$R^2$ is selected from the group consisting of hydrogen, and halo;

$R^3$ and $R^4$ are each independently selected from the group consisting of hydrogen, —(CO)—R' and —(CO)—R" wherein R', and R" are each independently selected from the group consisting of $C_{1-10}$ alkyl, aryl, and heteroaryl, which alkyl, aryl, and heteroaryl are optionally substituted with from 1 to 2 substituents independently selected from the group of halo, $NO_2$, aryl, heteroaryl, $CF_3$, CN, $OR^{20}$, $N(R^{20})_2$, $S(O)R^{22}$, $SO_2R^{22}$, $NR^{20}COR^{22}$, $COR^{20}$, $CO_2R^{20}$, $CON(R^{20})_2$, and $NR^{20}SO_2R^{22}$, and each optional heteroaryl, aryl, and heterocyclyl substituent is optionally substituted with halo, $NO_2$, alkyl, and $CF_3$;

$R^5$ is selected from the group consisting of $C_{1-15}$ alkyl, $C_{2-15}$ alkenyl, heterocyclyl, aryl, and heteroaryl, which alkyl, alkenyl, aryl, heterocyclyl and heteroaryl are optionally substituted with from 1 to 3 substituents independently selected from the group consisting of halo, alkyl, aryl, hcteroaryl, $CF_3$, CN, $OR^{20}$, $SR^{20}$, $N(R^{20})_2$, $S(O)R^{22}$, $SO_2R^{22}$, $SO_2N(R^{20})_2$, $S(O)_3R^{20}$, $P(O)(OR^{20})_2$, $NR^{20}COR^{22}$, $NR^{20}CO_2R^{22}$, $NR^{20}CON(R^{20})_2$, $COR^{20}$, $CO_2R^{20}$, and $CON(R^{20})_2$, and each optional alkyl, heteroaryl, and aryl substituent is optionally substituted with halo, alkyl, $CF_3$, $CO_2R^{20}$, $CON(R^{20})_2$, $NR^{20}CON(R^{20})_2$, $S(O)_3R^{20}$, $P(O)(OR^{20})_2$, $S(O)R^{22}$, $SO_2R^{22}$, $SO_2N(R^{22})_2$, CN, or $OR^{20}$;

$R^6$ is selected from the group consisting of H, and $C_{1-6}$ alkyl optionally substituted with $CF_3$, and $OR^{20}$;

$R^8$ is independently selected from the group consisting of H, and $C_1$–$C_8$ alkyl optionally substituted with one aryl substituent that is optionally substituted with halo or $CF_3$;

$R^{20}$ is selected from the group consisting of H, $C_{1-6}$ alkyl, and aryl, which alkyl, and aryl, are optionally substituted with 1 substituent independently selected from halo, alkyl, aryl, mono- or dialkylamino, CN, O—$C_{1-6}$ alkyl, and $CF_3$; and $R^{22}$ is selected from the group consisting of hydrogen, $Cl_{1-6}$ alkyl and aryl, which alkyl and aryl are optionally substituted with 1 substituent independently selected from the group consisting of halo, alkyl, mono- or dialkylamino, alkyl or CN, O—$C_{1-6}$ alkyl, and $CF_3$ wherein when Z=$NR^8$ then $R^5$ and $R^8$ may bond to form a 4 or 5 or 6 membered saturated or unsaturated ring; wherein when $X^1$=$NR^6$ and when Z=$NR^8$, then $R^6$ and $R^8$ may bond to form a 4 or 5 or 6 membered saturated or unsaturated ring; and wherein when $X^1$=$NR^6$ and Y=O or S, then $R^5$ and $R^6$ may bond to form a 5 or a 6 membered saturated or unsaturated ring.

4. The compound of claim 1 wherein Y=O, S;

$R^2$ is selected from the group consisting of hydrogen, and halo;

$R^3$ and $R^4$ are each independently selected from the group consisting of hydrogen, —(CO)—R' and —(CO)—R" wherein R', and R" are selected from the group consisting of $C_{1-6}$ alkyl, and aryl, which alkyl and aryl are optionally substituted with from 1 to 2 substituents independently selected from the group consisting of halo, $NO_2$, aryl, $CF_3$, CN, $OR^{20}$, $N(R^{20})_2$, $S(O)R^{22}$, $SO_2R^{22}$, $NR^{20}COR^{22}$, and each optional aryl substituent is optionally substituted with halo, $NO_2$, alkyl, and $CF_3$;

$R^5$ is selected from the group consisting of $C_{1-15}$ alkyl, $C_{2-15}$ alkenyl, aryl, and heteroaryl, which alkyl, alkenyl, aryl, and heteroaryl are optionally substituted with from 1 to 3 substituents independently selected from the group consisting of halo, alkyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $S(O)_3R^{20}$, $NR^{20}COR^{22}$, $NR^{20}CO_2R^{22}$, $NR^{20}CON(R^{20})_2$, $CO_2R^{20}$, $CON(R^{20})_2$, and wherein each optional alkyl, heteroaryl, and aryl substituent is optionally substituted with halo, alkyl, $CF_3$, $CO_2R^{20}$, $CON(R^{20})_2$, $S(O)_3R^{20}$, $S(O)R^{22}$, $SO_2R^{22}$, $SO_2N(R^{20})_2$, CN, or $OR^{20}$;

$R^6$ is selected from the group consisting of H, and $C_{1-4}$ alkyl;

$R^8$ is selected from the group consisting of H, and $C_1$–$C_8$ alkyl;

$R^{20}$ is selected from the group consisting of H, $C_{1-6}$ alkyl, and aryl, which alkyl and aryl are optionally substituted with 1 substituent selected from the group consisting of halo, alkyl, aryl, mono- or dialkylamino, CN, O—$C_{1-6}$ alkyl, and $CF_3$; and $R^{22}$ is a member selected from the group consisting of hydrogen, $C_{1-6}$ alkyl and aryl, which alkyl and aryl are optionally substituted with 1 substituent selected from the group consisting of halo, alkyl, CN, O—$C_{1-6}$ alkyl, and $CF_3$ wherein when Z=$NR^8$ then $R^5$ and $R^8$ may bond to form a 4 or 5 or 6 membered saturated or unsaturated ring; wherein when $X^1$=$NR^6$ and when Z=$NR^8$, then $R^6$ and $R^8$ may bond to form a 4 or 5 or 6 membered saturated or unsaturated ring; and wherein when $X^1$=$NR^6$ and Y=O or S, then $R^5$ and $R^6$ may bond to form a 5 or a 6 membered saturated or unsaturated ring.

5. The compound of claim 1 wherein Y=O, S;

$R^2$ is selected from the group consisting of hydrogen, and halo;

$R^3$ and $R^4$ are each independently selected from the group consisting of hydrogen, —(CO)—R' and —(CO)—R" wherein R', and R" are each $C_{1-6}$ alkyl which alkyl is optionally substituted with 1 substituent selected from the group consisting of aryl, $CF_3$, CN, $OR^{20}$, and $N(R^{20})_2$, and wherein each optional aryl substituent is optionally substituted with halo, $NO_2$, alkyl, and $CF_3$;

$R^5$ is selected from the group consisting of $C_{1-8}$ alkyl, $C_{2-8}$ alkenyl, and aryl, which alkyl, alkenyl, and aryl, is optionally substituted with from 1 to 2 substituents independently selected from the group consisting of halo, alkyl aryl, heteroaryl, $CF_3$, CN, $OR^{20}$, $S(O)R^{22}$, $SO_2R^{22}$, $SO_2N(R^{20})_2$, $S(O)_3R^{20}$, $NR^{20}COR^{22}$, $NR^{20}CON(R^{20})_2$, $CO_2R^{20}$, and $CON(R^{20})_2$, and wherein each optional alkyl and aryl substituent is optionally substituted with halo, alkyl, $CF_3$, $CO_2R^{20}$, $S(O)_3R^{20}$, CN, or $OR^{20}$;

$R^6$ is selected from the group consisting of H, and $C_{1-3}$ alkyl;

$R^8$ is selected from the group consisting of H, and $C_{1-3}$ alkyl;

$R_{20}$ is selected from the group consisting of H, and $C_{1-6}$ alkyl, which alkyl is optionally substituted with aryl; and $R_{22}$ is selected from the group consisting of hydrogen and $C_{1-6}$ wherein when $Z=NR^8$ then $R^5$ and $R^8$ may bond to form a 4 or 5 or 6 membered saturated or unsaturated ring; wherein when $X^1=NR^6$ and when $Z=NR^8$, then $R^6$ and $R^8$ may bond to form a 4 or 5 or 6 membered saturated or unsaturated ring; and wherein when $X^1=NR^6$ and $Y=O$ or S, then $R^5$ and $R^6$ may bond to form a 5 or a 6 membered saturated or unsaturated ring.

6. The compound of claims 1 or 2 or 3 or 4 wherein $X^1=O$; $Y=O$, S; $Z=NR^8$; and $R^2$ is selected from the group consisting of hydrogen, and halo.

7. The compound of claims 1 or 2 or 3 or 4 wherein $X^1=NR^6$; $Y=O$, S; $Z=O$; and $R^2$ is selected from the group consisting of hydrogen, and halo.

8. The compound of claims 1 or 2 or 3 or 4 wherein $X^1=S$; $Y=O$ or S; $Z=NR^8$; and $R^2$ is selected from the group consisting of hydrogen, and halo.

9. The compound of claims 1 or 2 or 3 or 4 wherein $X^1=NR^6$; $Y=O$ or S; $Z=NR^8$; and $R^2$ is selected from the group consisting of hydrogen, and halo.

10. The compound of claim 5 wherein $X^1=O$; $Y=O$ or S; and $Z=NR^8$.

11. The compound of claim 10 wherein $R^3$ and $R^4$ are each independently selected from the group consisting of hydrogen, —(CO)—R' and —(CO)—R" wherein R', and R" are each $C_{1-6}$ alkyl;

$R^5$ is selected from the group consisting of $C_{1-8}$ alkyl, $C_{2-8}$ alkenyl, and aryl, which alkyl, alkenyl, and aryl, are each optionally substituted with from 1 to 2 substituents independently selected from the group consisting of halo, alkyl, aryl, heteroaryl, $CF_3$, CN, $OR^{20}$, $S(O)R^{22}$, $SO_2R^{22}$, $SO_2N(R^{20})_2$, $S(O)_3R^{20}$, $NR^{20}COR^{22}$, $NR^{20}CON(R^{20})_2$, $CO_2R^{20}$, and $CON(R^{20})_2$, and each optional alkyl, and aryl substituent is optionally substituted with halo, alkyl, $CF_3$, $CO_2R^{20}$, $S(O)_3R^{20}$, CN, or $OR^{20}$; and $R^8$ is independently selected from the group consisting of H, and $C_{1-3}$ alkyl and wherein $R^5$ and $R^8$ may bond to form a 4 or 5 or 6 membered saturated ring.

12. The compound of claim 11 wherein $R^3$ and $R^4$ are each independently selected from the group consisting of hydrogen, —(CO)—R', and —(CO)—R" wherein R', and R" are each independently selected from the group consisting of methyl, isopropyl, and cyclopentyl;

$R^5$ is selected from the group consisting of $C_{1-8}$ alkyl, and $C_{2-8}$ alkenyl, which alkyl and alkenyl are optionally substituted with from 1 to 2 substituents independently selected from the group consisting of halo, alkyl, aryl, $CF_3$, CN, $OR^{20}$, $S(O)_3R^{20}$, and $CO_2R^{20}$, and wherein each optional alkyl, and aryl substituent is optionally substituted with halo, alkyl, $CF_3$, $CO_2R^{20}$, $S(O)_3R^{20}$, CN, or $OR^{20}$; and $R^8$ is selected from the group consisting of H, and $C_1-C_3$ alkyl and wherein $R^5$ and $R^8$ may bond to form a 4 or 5 or 6 membered saturated ring.

13. The compound of claim 11 wherein $R^3$ and $R^4$ are each independently selected from the group consisting of hydrogen, —(CO)—R', and —(CO)—R" wherein R', and R" are each methyl;

$R^5$ is selected from the group consisting of $C_{1-8}$ alkyl, and $C_{2-8}$ alkenyl, which alkyl, and alkenyl are optionally substituted with from 1 to 2 substituents independently selected from the group consisting of alkyl, aryl, $OR^{20}$, $CO_2R^{20}$, and wherein each optional alkyl and aryl substituent are optionally substituted with halo, alkyl, $CF_3$, $CO_2R^{20}$, or $OR^{20}$;

$R^8$ is selected from the group consisting of H, and $C_1-C_3$ alkyl; and $R_{20}$ is a selected from the group consisting of H, and $C_{1-6}$ alkyl, which alkyl is optionally substituted with aryl, and wherein $R^5$ and $R^8$ may bond to form a 4 or 5 or 6 membered saturated ring.

14. The compound of claim 11 wherein $R^3$ and $R^4$ are each hydrogen;

$R^5$ is selected from the group consisting of $C_{1-8}$ alkyl, and $C_{2-8}$ alkenyl, which alkyl and alkenyl are optionally substituted with from 1 to 2 substituents independently selected from the group consisting of alkyl, aryl, $OR^{20}$, and $CO_2R^{20}$, and wherein each optional alkyl and aryl substituent is optionally substituted with halo, or $CO_2R^{20}$;

$R^8$ is selected from the group consisting of H, and $C_1-C_3$ alkyl; and $R_{20}$ is selected from the group consisting of H, and $C_{1-3}$ alkyl, which alkyl is optionally substituted with aryl and wherein $R^5$ and $R^8$ may bond to form a 4 or 5 or 6 membered saturated ring.

15. The compound of claim 11 wherein $R^3$ and $R^4$ are each hydrogen;

$R^5$ is selected from the group consisting of $C_{1-8}$ alkyl, and $C_{2-8}$ alkenyl, which alkyl, and alkenyl, are optionally substituted with from 1 to 2 substituents independently selected from the group consisting of aryl, $OR^{20}$, and $CO_2R^{20}$, and wherein each optional aryl substituent is optionally substituted with halo;

$R^8$ is selected from the group consisting of H, and $C_1-C_3$ alkyl; and $R_{20}$ is selected from the group consisting of H, and methyl and wherein $R^5$ and $R^8$ may bond to form a 4 or 5 or 6 membered saturated ring.

16. The compound of claim 15 wherein $R^2$=H.

17. The compound of claim 16 wherein $Y=O$; $R^8$ is H; and $R^5$ is selected from the group consisting of methyl, ethyl, n-propyl, n-butyl, cyclopentyl, benzyl, (4-fluorophenylmethyl), isopropyl, cyclopropyl, cyclohexyl, allyl, 2-carboethoxyethyl, carbomethoxymethyl, 2-phenylcyclopropyl, cyclobutyl, 2-benzyloxycyclopentyl, 2-hydroxycyclopentyl, 2-carbomethoxycyclopentyl, 2-(3-carboethoxy-norborn-5-enyl), 2-(3-carboxy-norborn-5-enyl), 2-(3-carboethoxy-norbornyl), and 2-carboxycyclopentyl.

18. The compound of claim 16 wherein $Y=S$; $R^5$ is methyl, and $R^8$ is methyl.

19. The compound of claim 16 wherein $Z=NR^8$ and $R^5$ and $R^8$ bond to form a 5 or 6 membered saturated rings.

20. The compound of claim 16 wherein $Y=S$; $R^8$ is H; and $R^5$ is selected from the group consisting of methyl, ethyl, n-propyl, n-butyl, cyclopentyl, benzyl, isopropyl, cyclopropyl, cyclohexyl, allyl, cyclobutyl, 2-benzyloxycyclopentyl, and 2-hydroxycyclopentyl.

21. The compound of claim 5 wherein $X^1=NR^6$; $Y=O$ or S; $Z=O$; and $R^2$ is H.

22. The compound of claim 21 wherein $R^3$ and $R^4$ are independently selected from the group consisting of hydrogen, —(CO)—R', and —(CO)—R" wherein R', and R" are each methyl;

R$^5$ is selected from the group consisting of C$_{1-8}$ alkyl, C$_{2-8}$ alkenyl, and aryl, which alkyl, alkenyl, and aryl, are optionally substituted with from 1 to 2 substituents independently selected from the group consisting of halo, alkyl, aryl, heteroaryl, CF$_3$, CN, OR$^{20}$, S(O)R$^{22}$, SO$_2$R$^{22}$, SO$_2$N(R$^{20}$)$_2$, S(O)$_3$R$^{20}$, NR$^{20}$COR$^{22}$, NR$^{20}$CON(R$^{20}$)$_2$, CO$_2$R$^{20}$, and CON(R$^{20}$)$_2$, and wherein each optional alkyl, and aryl substituent is optionally substituted with halo, alkyl, CF$_3$, CO$_2$R$^{20}$, S(O)$_3$R$^{20}$, CN, or OR$^{20}$; and R$^6$ is selected from the group consisting of H, and C$_1$–C$_3$ alkyl wherein when X$^1$=NR$^6$ then R$^5$ and R$^6$ may bond to form a 4 or 5 or 6 membered saturated or unsaturated ring.

23. The compound of claim 21 wherein R$^3$ and R$^4$ are hydrogen;

R$^5$ is C$_{1-8}$ alkyl, which alkyl is optionally substituted with 1 substituent selected from the group consisting of aryl, OR$^{20}$, CO$_2$R$^{20}$, and CON(R$^{20}$)$_2$, and wherein each optional aryl substituent is optionally substituted with halo, alkyl CF$_3$, or CO$_2$R$^{20}$; and R$^6$ is independently selected from the group consisting of H, and C$_1$–C$_3$ alkyl wherein when X$^1$=NR$^6$ then R$^5$ and R$^6$ may combine to form a 4 or 5 or 6 membered saturated or unsaturated ring.

24. The compound of claim 21 wherein R$^3$ and R$^4$ are each hydrogen;

R$^5$ is a C$_{1-8}$ alkyl; and

R$^6$ is selected from the group consisting of H, and C$_1$–C$_3$ alkyl wherein when=NR$^6$ then R$^5$ and R$^6$ may form a 4 or 5 or 6 membered saturated or unsaturated ring.

25. The compound of claim 24 wherein R$^5$ is methyl or cyclopentyl and R$^6$=H.

26. The compound of claim 24 wherein X$^1$=N$^6$, =O, and R$^5$ and R$^6$ combine to form a 5 membered unsaturated ring wherein R$^5$ and R$^6$ together form CH=CH.

27. The compound of claim 5 wherein X$^1$=S; Y=O or S; Z=NR$^8$; and R$^2$ is H.

28. The compound of claim 26 wherein R$^3$ and R$^4$ are each independently selected from the group consisting of hydrogen, —(CO)—R' and —(CO)—R", wherein R' and R" are each methyl;

R$^5$ is selected from the group consisting of C$_{1-8}$ alkyl, C$_{2-8}$ alkenyl, and aryl, which alkyl, alkenyl and aryl, are optionally substituted with from 1 to 2 substituents independently selected from the group consisting of halo, alkyl, aryl, heteroaryl, CF$_3$, CN, OR$^{20}$, S(O)R$^{22}$, SO$_2$R$^{22}$, SO$_2$N(R$^{20}$)$_2$, S(O)$_3$R$^{20}$, NR$^{20}$COR$^{22}$, NR$^{20}$CON(R$^{20}$)$_2$, CO$_2$R$^{20}$, and CON(R$^{20}$)$_2$, and wherein each optional alkyl and aryl substituent is further optionally substituted with halo, alkyl, CF$_3$, CO$_2$R$^{20}$, S(O)$_3$R$^{20}$, CN, or OR$^{20}$; and R$^8$ is selected from the group consisting of H, and C$_1$–C$_3$ alkyl.

29. The compound of claim 27 wherein R$^3$ and R$^4$ are each hydrogen;

R$^5$ is C$_{1-8}$ alkyl that is optionally substituted with 1 substituent selected from the group consisting of aryl, OR$^{20}$, CO$_2$R$^{20}$, and CON(R$^{20}$)$_2$, and wherein each optional aryl substituent is optionally substituted with halo, alkyl, CF$_3$, CO$_2$R$^{20}$; and R$^8$ is H.

30. The compound of claim 27 wherein R$^3$ and R$^4$ are each hydrogen; R$^5$ is C$_{1-8}$ alkyl; and R$^8$ is H.

31. The compound of claim 30 wherein R$^5$ is methyl or cyclopentyl.

32. The compound of claim 5 wherein X$^1$=NR$^6$; Y=O or S; Z=NR$^8$; and R$^2$ is H.

33. The compound of claim 32 wherein R$^3$ and R$^4$ are each independently selected from the group consisting of hydrogen, —(CO)—R' and —(CO)—R" wherein R', and R" are each methyl;

R$^5$ is selected from the group consisting of C$_{1-8}$ alkyl, C$_{2-8}$ alkenyl, and aryl, which alkyl, alkenyl, and aryl, are optionally substituted with from 1 to 2 substituents independently selected from the group consisting of halo, alkyl, aryl, heteroaryl, CF$_3$, CN, OR$^{20}$, S(O)R$^{22}$, SO$_2$R$^{22}$, SO$_2$N(R$^{20}$)$_2$, S(O)$_3$R$^{20}$, NR$^{20}$COR$^{22}$, NR$^{20}$CON(R$^{20}$)$_2$, CO$_2$R$^{20}$, and CON(R$^{20}$)$_2$, and wherein each optional alkyl, and aryl substituent is optionally substituted with halo, alkyl, CF$_3$, CO$_2$R$^{20}$, S(O)$_3$R$^{20}$, CN, or OR$^{20}$;

R$^6$ is selected from the group consisting of H, and C$_1$–C$_3$ alkyl; and

R$^8$ is selected from the group consisting of H, and C$_1$–C$_3$ alkyl, wherein R$^6$ and R$^8$ may bond to form a 4 or 5 or 6 membered saturated or unsaturated ring.

34. The compound of clainm 32 wherein R$^3$ and R$^4$ are hydrogen;

R$^5$ is selected from the group consisting of C$_{1-8}$ alkyl, which alkyl is optionally substituted with 1 substituent independently selected from the group consisting of aryl, OR$^{20}$, CO$_2$R$^{20}$, CON(R$^{20}$)$_2$, and each optional aryl substituent is further optionally substituted with halo, alkyl, CF$_3$, and CO$_2$R$^{20}$; and R$^8$ is H.

35. The compound of claim 32 wherein R$^3$ and R$^4$ are each hydrogen; R$^5$ is C$_{1-8}$ alkyl; R$^6$=H; and R$^8$ is H.

36. The compound of claim 35 wherein R$^5$ is methyl or cyclopentyl.

37. The compound any one of claims 1 to 5 or 10–16 or 17–25 26–36 wherein R$_1$ is selected from the group consisting of 3-tetrahydrofuranyl, 3-tetrahydrothiofuranyl, 4-pyranyl, and 4 thiopyranyl.

38. The compound of claim 37 wherein R$_1$ is 3-tetrahydrofuranyl.

39. The compound of claim 1 wherein the compound is selected from the group consisting of 5'-O-(N-methylcarbamoyl)-6-((3R)-tetrahydrofuranyl) adenosine; (5'-O-(N-ethylcarbamoyl)6-((3R)-tetrahydrofuranyl; 5'-O-(N-propylcarbamoyl)-6-((3R)-tetrahydrofuranyl) adenosine; 5'-O-(N-butylcarbamoyl)-6-((3R)-tetrahydrofuranyl) adenosine; 5'-O-(N-cyclopentylcarbamoyl)-6-((3R)-tetrahydrofuranyl)adenosine; 5'-O-(N-benzylcarbamoyl)-6-((3R)-tetrahydrofuranyl)adenosine; (5'-O-(N-(4-fluorophenylmethylcarbamoyl)-6-((3R)-tetrahydrofuranyl) adenosine; 5'-O-[N-cyclohexylcarbamoyl]-6-((3R)-tetrahydrofuranyl)adenosine; 5'-O-[N-isopropylcarbamoyl]-6-[(3trahydrofuranyl)] adenosine; 5'-O-[N-cyclopropylcarbamoyl]-6-[((3R)-tetrahydrofuranyl)] adenosine; 5'-O-[N-2-(methoxycarbonyl) cyclopenthylcarbamoyl]-6-[((3R)-tetrahydrofuranyl)] adenosine; 5'-O-[N-2-(ethoxycarbonyl)(2S,3R)bicyclo[2.2.1]hept-5-enylcarbamoyl]-6-[(3R)-tetrahydroftiranyl] adenosine; 5'-O-[N-2-(ethoxycarbonyl)(2S,3R)bicyclo[2.2.1]heptylcarbamoyl]-6-[(3R)-tetrahydrofuranyl] adenosine; 5'-O-[N-(2R)-benzyloxy-(1R)-cyclopentylcarbamoyl]-6-[((3 R)-tetrahydrofuranyl] adenosine; 5'-O-[N-(2S)-benzyloxy-(1S)-cyclopentylcarbamoyl]-6-[((3R)tetrahydrofuranyl)] adenosine; 5'-O-[N-cyclobutylcarbamoyl]-6-[((3R)-tetrahydrofuranyl)] adenosine; 5'-O-[N-2-phenyl-1-cyclopropylcarbamoyl]-6-[((3R)tetrahydrofuranyl)] adenosine; 5'-O-[N-alkylcarbamoyl]-6-[((3R)

tetrahydrofuranyl)] adenosine, 5'-O-[N-2-(ethoxycarbonyl)ethylcarbamoyl]-6-[((3R)tetrahydrofuranyl)] adenosine; 5'-O-[N-1-(methoxycarbonyl) methylcarbamoyl]-6-[((3R)tetrahydrofuranyl)] adenosine; 5'-O-[N,N-dimethylcarbamoyl]-6-[((3R) tetrahydrofuranyl)] adenosine; 5'-O-[N-methylthionocarbamoyl]-6-[((3R) tetrahydrofuranyl)] adenosine; 5'-O-[N-ethylthiomocarbamoyl]-6-[((3R)tetrahydrofuranyl)] adenosine; 5'-O-[N-Isopropylthionocarbamoyl]-6-[((3R) tetrahydrofuranyl)] adenosine; 5'-O-[N-butylthionocarbamoyl]-6-((3R)tetrahydrofuranyl) adenosine; 5'-O-[N-propylthionocarbamoyl]-6-((3R)-tetrahydrofuranyl)adenosine; 5'-O-[N-piperidinothionocarbamoyl]-6-((3R) tetrahydrofuranyl) adenosine; 5'-O-[N-cyclopentylthionocarbamoyl]-6-((3R) tetrahydrofuranyl)adenosine; 5'-O-[N-pyrrolidinothionocarbamoyl]-6-((3R)tetrahydrofuranyl) adenosine; 5'-O-[N,N-dimethylthionocarbamoyl]-6-((3R) tetrahydrofuranyl)adenosine; 5'-O-[N-benzylthionocarbamoyl]-6-((3R)tetrahydrofuranyl) adenosine; 5'-O-[N-cyclohexylthionocarbamoyl]-6-((3R) tetrahydrofuranyl)adenosine; 5'-O-[N-(2S)benzyloxy-(1S) cyclopentylthionocarbamoyl]-6-[(3R)-tetrahydrofuranyl] adenosine; 5'-O-[N-(2R)benzyloxy-(1S)]-6-[(3R)-tetrahydrofuranyl] adenosine; 5'-O-[N-cyclobutylthionocarbamoyl]-6-((3R)tetrahydrofuranyl) adenosine; 5'-O-[N-cyclopropylthionocarbamoyl]-6-((3R) tetrahydrofuranyl)adenosine; 5'-O-[N-alkylthionocarbamoyl]-6-((3R)tetrahydrofuranyl) adenosine; 5'-O-[N-(2S)-hydroxy-(1S)-cyclopentylcarbamoyl]-6-[((3R)-tetrahydrofuranyl)] adenosine; 5'-O-[N-(2R)-hydroxy-(1R)-cyclopentylcarbamoyl]-6-((3R)-tetrahydrofuranyl) adenosine; 5'-O-[N-(2R)-hydroxy-(1R)-cyclopentylthionocarbamoyl]-6-((3R)-tetrahydrofuranyl) adenosine; 5'-O-[N-(2S)-hydroxy-(1S)-cyclopentylthionocarbamoyl]-6-((3R)tetrahydrofuranyl) adenosine; 5'-O-[N-2-(hydroxycarbamoyl) cyclopentylcarbamoyl]-6-[((3R)-tetrahydrofuranyl)] adenosine; 5'-O-[N-2-hydroxycarbamoyl] (2S,3R) bicyclo [2.2.1]hept-5-enylcarbamoyl]-6-[((3R)-tetrahydrofuranyl)] adenosine; 5'-O-[N-2-(hydroxycarbonyl)ethylcarbamoyl]-6-[((3R)-tetrahydrofuranyl)] adenosine; 5'-O-[N-1-(hydroxycarbonyl)methylcarbamoyl]-6-[((3R)-tetrahydrofuranyl] adenosine; 2',3'-O-diocetoxy-5'-O-[N-methylcarbamoyl]-6-[((3R)-tetrahydrofuranyl)] adenosine; 2-chloro-6-[((3R)-tetrahydrofuranyl)] adenosine; 2-Chloro-6[(3R)-tetrahydrofuranyl]-2',3'-isopropylidino-adenosine; 2-Chloro-5'[N-methylcarboxamido]-6[(3R)-tetrahydrofuranyl]-2',3'-isopropylidino-adenosine; 2-chloro-5'-O-[N-methylcarbamoyl}-6-[((3R)-tetrahydrofuranyl)] adenosine; 2-chloro-5'-O-[N-cyclopentylcarbamoyl]-6-[((3R)-tetrahydrofuranyl)] adenosine; Nor-5'-hydroxy-5'-(methoxycarbonylamino)-6-[(3R)-tetrahydrofuranyl] adenosine; 5'-deoxy-5'-(cyclopentyloxycarbonylamino)-6-[(3R)-tetrahydrofuranyl] adenosine; 5'-deoxy-(methoxythionocarbamoylamino]-6-[((3R)-tetrahydrofuranyl)] adenosine; 5'-deoxy-5'(cyclopentyloxythionocarbamoyl amino)-6-[((3R)-tetrahydrofuranyl)] adenosine; 5'-deoxy-5'-(methylaminocarbonylthio)-6-[((3R)-tetrahydrofuranyl)] adenosine; 5'-deoxy-5'-(cyclopentylaminocarbonylthio)-6-[((3R)-tetrahydrofuranyl)] adenosine; 5'-deoxy-5'(methylaminothionocarbonylthio)-6-[((3R)-tetrahydrofuranyl)] adenosine; 5'-deoxy-5'-(cyclopentylaminothionocarbonylthio)-6-[(3R)-tetrahydrofuranyl] adenosine; 5'-deoxy-5'-(methylaminocarbonylaza)-6-[((3R)-tetrahydrofuranyl)] adenosine; Nor-5'-deoxy-5'-(cyclopentylaminocarbonylaza)-6-[((3R)-tetrahydrofuranyl)] adenosine; Nor-5'-deoxy-5'-(methylaminothionocarbonylaza)-6-[((3R)-tetrahydrofuranyl)] adenosine; Nor-5'-deoxy-5'-(cyclopentylthiocarbonylaza)-6-[((3R)-tetrahydrofuranyl)] adenosine; Nor-5'-deoxy-5'-(ethylaminocarbonylaza)-6-[((3R)-tetrahydrofuranyl)] adenosine; and Nor-5'-deoxy-5'-(N-1,3-oxazolin-2-onyl)-6-[(3R)-tetrahydrofuranyl)] adenosine.

40. A method for modifying cardiac activity in a mammal experiencing a heart electrical disorder that can be treated by stimulating an $A_1$ adenosine receptor comprising the administration of a therapeutically effective amount of a compound of claim 1 to the mammal.

41. A pharmaceutical composition comprising the compound of claim 1 and one or more pharmaceutically acceptable excipients.

42. The pharmaceutical composition of claim 41 wherein the pharmaceutical composition is in the form of a solution.

43. The pharmaceutical composition of claim 41 wherein the pharmaceutical composition is in the form of a tablet.

* * * * *

UNITED STATES PATENT AND TRADEMARK OFFICE
CERTIFICATE OF CORRECTION

PATENT NO. : 6,258,793 B1
DATED : July 10, 2001
INVENTOR(S) : Palle et al.

It is certified that error appears in the above-identified patent and that said Letters Patent is hereby corrected as shown below:

Column 4,
Line 54, delete "$R^{20}$" and replace with -- $R^{22}$ --.

Column 6,
Line 29, delete "substituen" and replace with -- substituent is --.
Line 40, delete "NR'" and replace with -- $NR^8$ --.
Line 50, delete "substitue" and replace with -- substituent is --.

Column 8,
Line 4, delete "carboxatnide" and replace with -- carboxamide --.

Column 9,
Line 56, delete "nol" and replace with -- no} --.

Column 35,
Line 24, delete "dihaydroxyoxolan" and replace with -- dihydroxyoxolan --.

Column 41,
Line 27, delete "1-yl" and replace with -- 2-yl --.

Column 53,
Line 23, delete "1R, 2R" and replace with -- 1S, 2S --.

Column 55,
Line 65, after 1H), and before (m, 2H) insert -- 3.95- 4.05 --.

Column 56,
Line 30, delete "gom" and replace with -- gum --.

Column 61,
Line 62, after the word tetrahydrofuranyl)] insert the word -- adenosine --.

Column 67,
Line 36, delete "CAP" and replace -- CPA --

UNITED STATES PATENT AND TRADEMARK OFFICE
CERTIFICATE OF CORRECTION

PATENT NO. : 6,258,793 B1
DATED : July 10, 2001
INVENTOR(S) : Palle et al.

It is certified that error appears in the above-identified patent and that said Letters Patent is hereby corrected as shown below:

Column 71,
Line 59, delete "$OCONR_{20}SO_2R^{22}$" and replace with -- $OCONR^{20}SO_2R^{22}$ --.

Column 78,
Line 52, delete "[(3trahydrofuranyl)]" and replace with -- [(3R)-tetrahydrofuranyl)] --.
Line 57, delete "[(3R)-tetrahydroftirayl]" and replace with
-- [(3R)-tetrahydrofuranyl] --.

Signed and Sealed this

Twenty-sixth Day of March, 2002

Attest:

JAMES E. ROGAN
Attesting Officer     Director of the United States Patent and Trademark Office